(12) United States Patent
Romeo et al.

(10) Patent No.: US 8,796,310 B2
(45) Date of Patent: Aug. 5, 2014

(54) AMINO-PYRIDINE-CONTAINING SPLEEN TYROSINE KINASE (SYK) INHIBITORS

(75) Inventors: Eric Thomas Romeo, Allston, MA (US); Michelle R. Machacek, Brookline, MA (US); Benjamin Wesley Trotter, Newton, MA (US); Thomas Allen Miller, Wakefield, MA (US); Brian Michael Andresen, Sharon, MA (US); Neville John Anthony, Northborough, MA (US); Brandon M. Taoka, Hoboken, NJ (US); Yuan Liu, Belmont, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/704,484

(22) PCT Filed: Apr. 30, 2012

(86) PCT No.: PCT/US2012/035725
§ 371 (c)(1),
(2), (4) Date: Dec. 14, 2012

(87) PCT Pub. No.: WO2012/151137
PCT Pub. Date: Nov. 8, 2012

(65) Prior Publication Data
US 2013/0090309 A1   Apr. 11, 2013

Related U.S. Application Data

(60) Provisional application No. 61/482,508, filed on May 4, 2011.

(51) Int. Cl.
*A61K 31/444*  (2006.01)
*C07D 277/04*  (2006.01)

(52) U.S. Cl.
CPC ............ *A61K 31/444* (2013.01); *C07D 277/04* (2013.01)
USPC .......................................... 514/333; 546/256

(58) Field of Classification Search
CPC ............................. A61K 31/444; C07D 277/04
USPC ............................................. 514/333; 546/256
See application file for complete search history.

(56) References Cited

U.S. PATENT DOCUMENTS

| 7,326,699 | B2 | 2/2008 | Capraro et al. |
| 2006/0205731 | A1* | 9/2006 | Kodama et al. .......... 514/252.03 |
| 2007/0021472 | A1 | 1/2007 | Zhu et al. |
| 2011/0245205 | A1 | 10/2011 | Altman et al. |

FOREIGN PATENT DOCUMENTS

| WO | 0119788 A2 | 3/2001 |
| WO | 0164642 A2 | 9/2001 |
| WO | 2004014902 A2 | 2/2004 |
| WO | 2005021529 A1 | 3/2005 |
| WO | 2005077368 A2 | 8/2005 |
| WO | 2006093247 A1 | 9/2006 |
| WO | 2008106202 A1 | 9/2008 |
| WO | 2011075515 A1 | 6/2011 |
| WO | 2011075517 A1 | 6/2011 |
| WO | 2011075560 A1 | 6/2011 |
| WO | 2011086085 A1 | 7/2011 |
| WO | 2011090738 A2 | 7/2011 |
| WO | 2012151137 A1 | 11/2012 |
| WO | 2012154518 A1 | 11/2012 |
| WO | 2012154519 A1 | 11/2012 |
| WO | 2012154520 A1 | 11/2012 |

OTHER PUBLICATIONS

Atwell, et al., "A Novel Mode of Gleevec Binding is Revealed by the Structure of Spleen Tyrosine Kinase," The Journal of Biological Chemistry, 2004, vol. 279, No. 53, pp. 55827-55832.
International Search Report corresponding to International Application No. PCT/US2012/35725, issued Jul. 27, 2012.
Written Opinion issued Jul. 27, 2012 by International Searching Authority in connection with International Application No. PCT/US2012/35725.
International Search Report and Written Opinion corresponding to International Application No. PCT/US2013/68190, issued Mar. 4, 2014.

* cited by examiner

*Primary Examiner* — D M Seaman
(74) *Attorney, Agent, or Firm* — Eric A. Meade; Valerie J. Camara

(57) ABSTRACT

The invention provides certain amino-pyridine-containing compounds of the Formula (I) or pharmaceutically acceptable salts thereof, wherein $R^1$, $R^2$, $R^3$, $R^4$, $R^5$, $R^6$, $R^7$, $R^8$, $R^9$, and n are as defined herein. The invention also provides pharmaceutical compositions comprising such compounds, and methods of using the compounds for treating diseases or conditions mediated by Spleen Tyrosine Kinase (Syk) kinase.

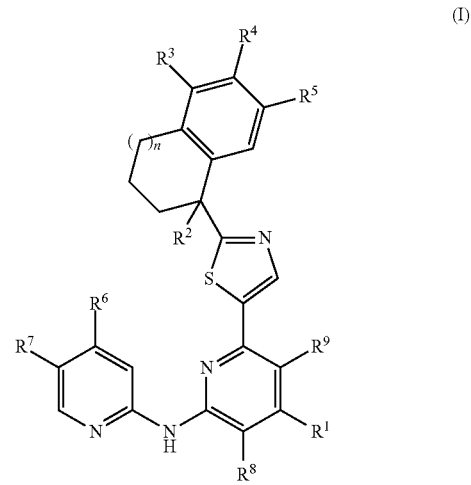

38 Claims, 1 Drawing Sheet

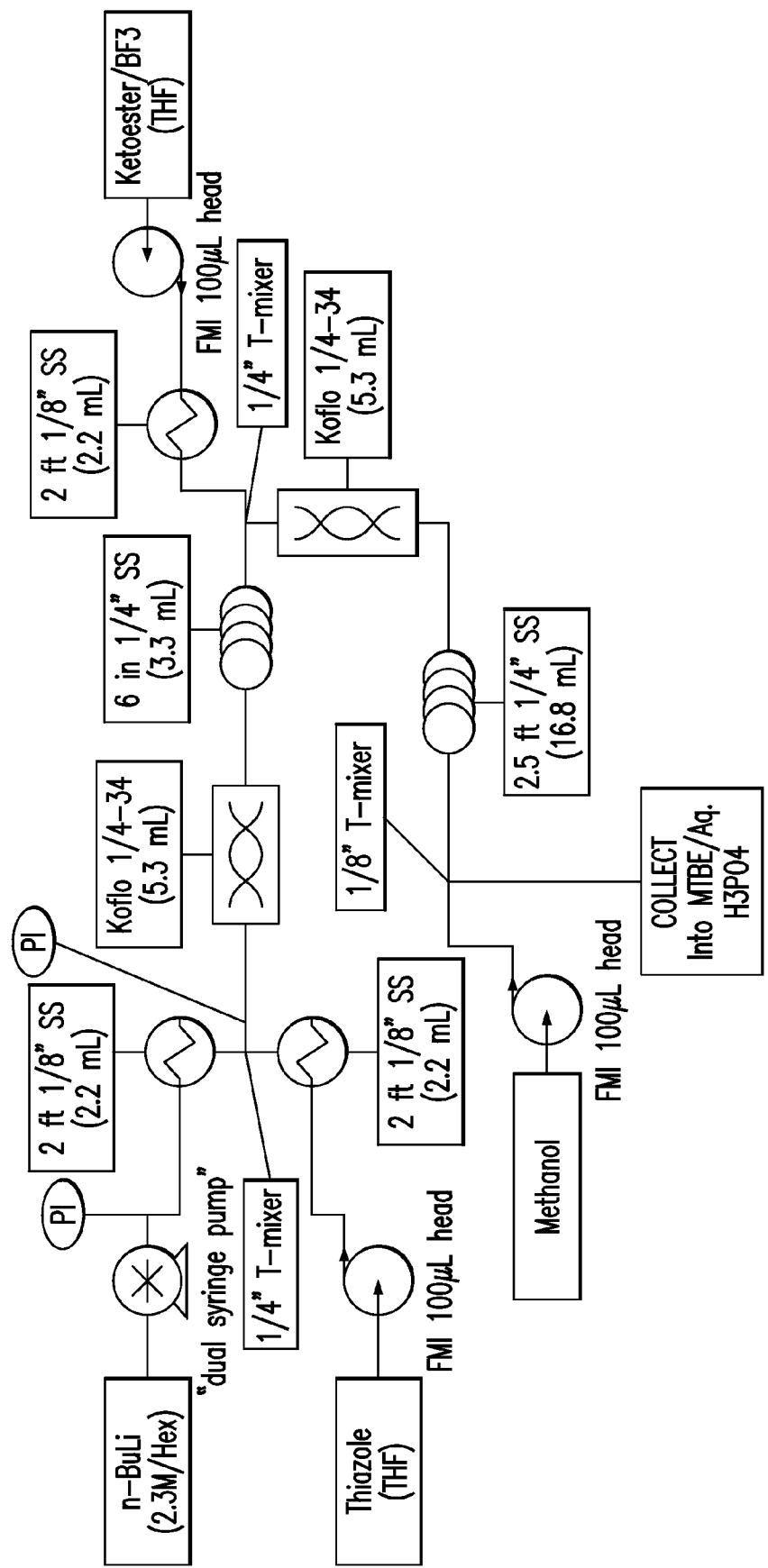

AMINO-PYRIDINE-CONTAINING SPLEEN TYROSINE KINASE (SYK) INHIBITORS

CROSS-REFERENCE TO RELATED APPLICATIONS

This Application is a U.S. National Stage Application under 35 U.S.C. §371 of PCT Application No. PCT/US2012/035725 filed Apr. 30, 2012 which claims priority under 35 U.S.C. §119(e) of U.S. Provisional Application No. 61/482,508 filed May 4, 2011.

FIELD OF THE INVENTION

The present invention relates to certain amino-pyridine-containing compounds of the Formula (I) (also referred to herein as the "compounds of the Formula (I)" or "compounds of Formula (I)") which are inhibitors of Spleen Tyrosine Kinase (Syk) kinase activity. The present invention also provides compositions comprising such compounds, and methods of using such compounds for treating conditions or disorders associated with inappropriate Syk activity, in particular in the treatment and prevention of disease states mediated by Syk. Such disease states may include inflammatory, allergic and autoimmune diseases, for example, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, idiopathic thrombocytopenic purpura (ITP), multiple sclerosis, cancer, HIV and lupus.

BACKGROUND OF THE INVENTION

Spleen Tyrosine Kinase (Syk) is a protein tyrosine kinase which has been described as a key mediator of immunoreceptor signaling in a host of inflammatory cells including mast cells, B-cells, macrophages and neutrophils. These immunoreceptors, including Fc receptors and the B-cell receptor, are important for both allergic diseases and antibody-mediated autoimmune diseases and thus pharmacologically interfering with Syk could conceivably treat these disorders.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE and IgG become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesized lipid mediators including prostaglandins and leukotrienes.

Syk kinase is a non-receptor linked tyrosine kinase which is important in transducing the downstream cellular signals associated with cross-linking $Fc_{epsilon}RI$ and or $Fc_{epsilon}RI$ receptors, and is positioned early in the signaling cascade. In mast cells, for example, the early sequence of $Fc_{epsilon}RI$ signaling following allergen cross-linking of receptor-IgE complexes involves first Lyn (a Src family tyrosine kinase) and then Syk. Inhibitors of Syk activity would therefore be expected to inhibit all downstream signaling cascades thereby alleviating the immediate allergic response and adverse events initiated by the release of pro-inflammatory mediators and spasmogens (Wong et al. 2004, *Expert Opin. Investig. Drugs* (2004) 13 (7) 743-762).

Recently, it has been shown that the Syk kinase inhibitor R112 (Rigel), dosed intranasally in a phase I/II study for the treatment of allergic rhinitis, gave a statistically significant decrease in $PGD_2$, a key immune mediator that is highly correlated with improvements in allergic rhinorrhea, as well as being safe across a range of indicators, thus providing the first evidence for the clinical safety and efficacy of a topical Syk kinase inhibitor. (Meltzer, Eli O.; Berkowitz, Robert B.; Grossbard, Elliott B, *Journal of Allergy and Clinical Immunology* (2005), 115(4), 791-796). In a more recent phase II clinical trial for allergic rhinitis (Clinical Trials.gov Identifier NCT0015089), R112 was shown as having a lack of efficacy versus placebo.

Rheumatoid Arthritis (RA) is an auto-immune disease affecting approximately 1% of the population. It is characterised by inflammation of articular joints leading to debilitating destruction of bone and cartilage. Recent clinical studies with Rituximab, which causes a reversible B cell depletion, (J. C. W. Edwards et al. 2004, *New Eng. J. Med.* 350: 2572-2581) have shown that targeting B cell function is an appropriate therapeutic strategy in auto-immune diseases such as RA. Clinical benefit correlates with a reduction in auto-reactive antibodies (or Rheumatoid Factor) and these studies suggest that B cell function and indeed auto-antibody production are central to the ongoing pathology in the disease.

Studies using cells from mice deficient in the Spleen Tyrosine Kinase (Syk) have demonstrated a non-redundant role of this kinase in B cell function. The deficiency in Syk is characterised by a block in B cell development (M. Turner et al. 1995 *Nature* 379: 298-302 and Cheng et al. 1995, *Nature* 378: 303-306). These studies, along with studies on mature B cells deficient in Syk (Kurasaki et al. 2000, *Immunol. Rev.* 176:19-29), demonstrate that Syk is required for the differentiation and activation of B cells. Hence, inhibition of Syk in RA patients is likely to block B cell function, and thereby reduce Rheumatoid Factor production. In addition to the role of Syk in B cell function, and of further relevance to the treatment of RA, is the requirement for Syk activity in Fc receptor (FcR) signaling. FcR activation by immune complexes in RA has been suggested to contribute to the release of multiple pro-inflammatory mediators.

SUMMARY OF THE INVENTION

The present invention provides novel compounds that are potent inhibitors of Syk as well as pharmaceutical compositions containing them. As Syk inhibitors compounds of Formula (I) are useful in the treatment and prevention of diseases and disorders mediated by the Syk protein; such diseases and disorders include, but are not limited to, asthma, COPD, rheumatoid arthritis, cancer and idiopathic thrombocytopenic purpura.

BRIEF DESCRIPTION OF THE FIGURE

FIG. 1 shows the flow diagram used for an assembly used in preparing the intermediate, methyl 5-hydroxy-5-(thiazol-2-yl)-5,6,7,8-tetrahydronapthalene-2-carboxylate.

DETAILED DESCRIPTION OF THE INVENTION

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "therapeutically effective amount" as used herein, refers to an amount of the compound of Formula (I) and/or an additional therapeutic agent, or a composition thereof that is effective in producing the desired therapeutic, ameliorative, inhibitory or preventative effect when administered to a patient suffering from pain or an inflammatory disease or disorder. In the combination therapies of the present invention, a therapeutically effective amount can refer to each individual agent or to the combination as a whole, wherein the amounts of all agents administered are together effective, but wherein the component agent of the combination may not be present individually in an effective amount.

The term "preventing," as used herein with respect to cancer or an inflammatory disease or disorder, refers to reducing the likelihood of cancer pain or an inflammatory disease or disorder.

The term "alkyl," as used herein, refers to an aliphatic hydrocarbon group having one of its hydrogen atoms replaced with a bond having the specified number of carbon atoms. In different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom.

The term "aryl," as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$ aryl). In another embodiment an aryl group is phenyl. Non-limiting examples of aryl groups include phenyl and naphthyl.

The term "cycloalkyl," as used herein, refers to a saturated ring containing the specified number of ring carbon atoms, and no heteroatom. In a like manner the term "$C_3$-$C_6$ cycloalkyl" refers to a saturated ring having from 3 to 6 ring carbon atoms. Non-limiting examples of monocyclic cycloalkyls include cyclopropyl, cyclobutyl, cyclopentyl, and cyclohexyl.

The term "halo," as used herein, means —F, —Cl, —Br or —I. In one embodiment, a halo group is —F or —Cl. In another embodiment, a halo group is —F.

The term "fluoroalkyl," as used herein, refers to an alkyl group as defined above, wherein one or more of the alkyl group's hydrogen atoms has been replaced with a fluorine. In one embodiment, a fluoroalkyl group has from 1 to 6 carbon atoms. In another embodiment, a fluoroalkyl group has from 1 to 3 carbon atoms. In another embodiment, a fluoroalkyl group is substituted with from 1 to 3 F atoms. Non-limiting examples of fluoroalkyl groups include —$CH_2F$, —$CHF_2$, and —$CF_3$. The term "$C_1$-$C_3$ fluoroalkyl" refers to a fluoroalkyl group having from 1 to 3 carbon atoms.

The term "heteroaryl," as used herein, refers to an aromatic monocyclic or multicyclic ring system comprising about 5 to about 14 ring atoms, wherein from 1 to 3 of the ring atoms is independently N, O, or S and the remaining ring atoms are carbon atoms. In one embodiment, a heteroaryl group has 5 to 10 ring atoms. In another embodiment, a heteroaryl group is monocyclic ring system and has 5 or 6 ring atoms. In another embodiment, a heteroaryl group is a bicyclic ring system. A heteroaryl group is joined via a ring carbon atom. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, and the like. In one embodiment, a heteroaryl group is a 5-membered heteroaryl. In another embodiment, a heteroaryl group is a 6-membered heteroaryl.

The term "substituted" means that one or more hydrogens on the atoms of the designated are replaced with a selection from the indicated group, provided that the atoms' normal valencies under the existing circumstances are not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

When any substituent or variable occurs more than one time in any constituent or the compound of Formula (I), its definition on each occurrence is independent of its definition at every other occurrence, unless otherwise indicated.

The term "in purified form," as used herein, refers to the physical state of a compound after the compound is isolated from a synthetic process (e.g., from a reaction mixture), a natural source, or a combination thereof. The term "in purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula (I) may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention.

All stereoisomers (for example, geometric isomers, optical isomers and the like) of the present compounds (including those of the salts and solvates of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds of Formula (I) in all their isolated forms. For example, the above-identified compounds are intended to encompass all forms of the compounds such as, any solvates, hydrates, stereoisomers, and tautomers thereof.

As used herein, the term "composition" is intended to encompass a product comprising the specified ingredients in the specified amounts, as well as any product which results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) can be prepared without undue experimentation by conventional techniques well known to those skilled in the art or by processes analogous to those described in the Schemes and Examples herein using appropriate isotopically-enriched reagents and/or intermediates.

Compounds of the Invention

The present invention provides compound of Formula (I) or pharmaceutically acceptable salts thereof, wherein $R^1$, $R^2$, $R^3$, $R^4$, $R^5$, $R^6$, $R^7$, $R^8$, $R^9$, and n are as defined below. Described below are embodiments of the compound of Formula (I). The compound of Formula (IA), as is described in detail below, is an embodiment of the compound of Formula (I).

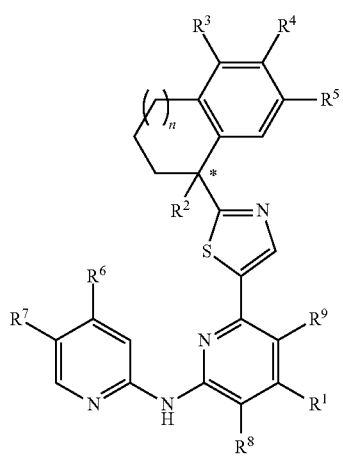
(I)

In embodiment no. 1 the present invention provides a compound of the Formula (I): or a pharmaceutically acceptable salt thereof, wherein
$R^1$ is selected from the group consisting of:
(i) —$C_1$-$C_3$ alkyl;
(ii) fluoroalkyl;
(iii) —$CH_2OR^{1a}$,
wherein $R^{1a}$ is selected from the group consisting of H and $C_1$-$C_6$ alkyl;
(iv) —$N(R^{1b})_2$,
wherein each occurrence of $R^{1b}$ is selected from the group consisting of H and $C_1$-$C_3$ alkyl, or two $R^{1b}$ together with the N atom to which they are attached form a group of the formula

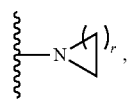

wherein r is 1, 2, 3, or 4;
(v) —O—($C_1$-$C_3$ alkyl);
(vi) —N(H)C(O)—($C_1$-$C_3$ alkyl);
(vii) halo;
(viii) H; and
(ix) morpholinyl;
$R^2$ is —OH, —O—($C_1$-$C_3$ alkyl), —$N(R^{2a})_2$, —$N(R^{2a})C(O)$—$R^{2b}$, or —F;
wherein each occurrence of $R^{2a}$ is selected from the group consisting of H and $C_1$-$C_3$ alkyl; and
$R^{2b}$ is $C_1$-$C_6$ alkyl;
$R^3$ is —$CO_2R^{3a}$, —$CH_2CO_2R^{3a}$, —$CH_2CH_2CO_2R^{3a}$, tetrazole, —$C(O)N(R^{3b})_2$, —$CH_2OH$, H, halo, —OH $C_1$-$C_6$ alkyl, —O—($C_1$-$C_3$ alkyl), —$N(R^{3b})_2$, —CN, —C(O)N(H)S(O)$_2R^{3c}$, —C(O)—N(H)($R^{3d}$), —C(O)N(H)C(O)$R^{3a}$, —P(O)(OR$^{3b}$)$_2$, or —B(OH)$_2$;
wherein $R^{3a}$ is selected from the group consisting of H and $C_1$-$C_6$ alkyl;
wherein each $R^{3b}$ is independently selected from the group consisting of H and $C_1$-$C_3$ alkyl;
wherein $R^{3c}$ is selected from the group consisting of $C_1$-$C_3$ alkyl, $C_1$-$C_3$ fluoroalkyl, $C_3$-$C_6$ cycloalkyl, and phenyl, wherein said phenyl is unsubstituted or substituted with one or two $C_1$-$C_3$ alkyl;
wherein $R^{3d}$ is selected from the group consisting of —CN, —O—($C_1$-$C_3$ alkyl), and tetrazole;
$R^4$ is —$CO_2R^{4a}$, —$CH_2CO_2R^{4a}$, —$CH_2CH_2CO_2R^{4a}$, tetrazole, —$C(O)N(R^{4b})_2$, —$CH_2OH$, H, halo, —OH, $C_1$-$C_6$ alkyl, —O—($C_1$-$C_3$ alkyl), —$N(R^{4b})_2$, —CN, —C(O)N(H)S(O)$_2R^{4c}$, —C(O)—N(H)($R^{4d}$), —C(O)N(H)C(O)$R^{4a}$, —P(O)(OR$^{4b}$)$_2$, or —B(OH)$_2$;
wherein $R^{4a}$ is selected from the group consisting of H and $C_1$-$C_6$ alkyl;
wherein each $R^{4b}$ is independently selected from the group consisting of H and $C_1$-$C_3$ alkyl;
wherein $R^{4c}$ is selected from the group consisting of $C_1$-$C_3$ alkyl, $C_1$-$C_3$ fluoroalkyl, $C_3$-$C_6$ cycloalkyl, and phenyl, wherein said phenyl is unsubstituted or substituted with one or two $C_1$-$C_3$ alkyl;
wherein $R^{4d}$ is selected from the group consisting of —CN, —O—($C_1$-$C_3$ alkyl), and tetrazole;
$R^5$ is —$CO_2R^{5a}$, —$CH_2CO_2R^{5a}$, —$CH_2CH_2CO_2R^{5a}$, tetrazole, —$C(O)N(R^{5b})_2$, —$CH_2OH$, H, halo, —OH, $C_1$-$C_6$ alkyl, —O—($C_1$-$C_3$ alkyl), —$N(R^{5b})_2$, —CN, —C(O)N(H)S(O)$_2R^{5c}$, —C(O)—N(H)($R^{5d}$), —C(O)N(H)C(O)$R^{5a}$, —P(O)(OR$^{5b}$)$_2$, or —B(OH)$_2$;
wherein $R^{5a}$ is selected from the group consisting of H and $C_1$-$C_6$ alkyl;
wherein each $R^{5b}$ is independently selected from the group consisting of H and $C_1$-$C_3$ alkyl;
wherein $R^{5c}$ is selected from the group consisting of $C_1$-$C_3$ alkyl, $C_1$-$C_3$ fluoroalkyl, $C_3$-$C_6$ cycloalkyl, and phenyl, wherein said phenyl is unsubstituted or substituted with one or two $C_1$-$C_3$ alkyl;
wherein $R^{5d}$ is selected from the group consisting of —CN, —O—($C_1$-$C_3$ alkyl), and tetrazole;
$R^6$ is selected from the group consisting of:
(i) $C_1$-$C_6$ alkyl;
(ii) $C_1$-$C_3$ fluoroalkyl;
(iii) —O—($C_1$-$C_6$ alkyl);
(iv) —O—($C_1$-$C_3$ fluoroalkyl);
(v) —$R^{6a}$, wherein $R^{6a}$ is selected from the group consisting of:
(a) $C_3$-$C_6$ cycloalkyl;
(b) a group of the formula

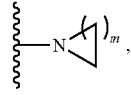

wherein m is 1, 2, 3, or 4;

(c) a group of the formula

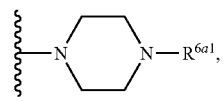

where $R^{6a1}$ is H, $C_1$-$C_3$ alkyl, or —$CH_2CH_2NH_2$; and
(d) a 5- to 6-membered heteroaryl containing 1 to 3 heteroatoms selected from the group consisting of N, O, and S;
wherein $R^{6a}$ is unsubstituted or substituted with 1 to 3 $R^{6a2}$ moieties selected from the group consisting of halo and $C_1$-$C_3$ alkyl;
(vi) —O—$R^{6b}$,
wherein $R^{6b}$ is selected from the group consisting of:
(a) $C_3$-$C_6$ cycloalkyl; and
(b) a group of the formula

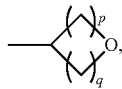

wherein p is 0, 1, or 2, and q is 1, 2, or 3;
wherein $R^{6b}$ is unsubstituted or substituted with 1 to 2 $R^{6b1}$ moieties selected from the group consisting of fluoro and $C_1$-$C_3$ alkyl;
(vii) —N($R^{6c}$)$_2$, wherein each occurrence of $R^{6c}$ is selected from the group consisting of H and $C_1$-$C_3$ alkyl;
(viii) —N(H)C(O)—($C_1$-$C_3$ alkyl);
(ix) —N(H)C(O)O—($C_1$-$C_3$ alkyl);
(x) —NHC(O)—N($R^{6d}$)$_2$, wherein each $R^{6d}$ is H or $C_1$-$C_3$ alkyl;
(xi) halo; and
(xii) H;
$R^7$ is H or halo;
$R^8$ is H or halo;
$R^9$ is H or halo; and
n is 0, 1, or 2.

In embodiment no. 2,
$R^2$ is —OH, —O—($C_1$-$C_3$ alkyl), or —N($R^{2a}$)$_2$;
$R^3$ is —CO$_2R^{3a}$, —CH$_2$CO$_2R^{3a}$, —CH$_2$CH$_2$CO$_2R^{3a}$, tetrazole, —C(O)N($R^{3b}$)$_2$, —CH$_2$OH, H, halo, $C_1$-$C_6$ alkyl, —O—($C_1$-$C_3$ alkyl), or —N($R^{3b}$)$_2$;
$R^4$ is —CO$_2R^{4a}$, —CH$_2$CO$_2R^{4a}$, —CH$_2$CH$_2$CO$_2R^{4a}$, tetrazole, —C(O)N($R^{4b}$)$_2$, —CH$_2$OH, H, halo, $C_1$-$C_6$ alkyl, —O—($C_1$-$C_3$ alkyl), or —N($R^{4b}$)$_2$; and
$R^5$ is —CO$_2R^{5a}$, —CH$_2$CO$_2R^{5a}$, —CH$_2$CH$_2$CO$_2R^{5a}$, tetrazole, —C(O)N($R^{5b}$)$_2$, —CH$_2$OH, H, halo, $C_1$-$C_6$ alkyl, —O—($C_1$-$C_3$ alkyl), and —N($R^{5b}$)$_2$,
$R^6$ is as described in (i)-(viii), (xi), or (xii) in embodiment no. 1;
and the remaining variables are as described in embodiment no. 1.

In the above-illustrated structural formula of the compound of Formula (I), the ring carbon bonded to $R^2$ and the illustrated thiazole ring is denoted in the illustration with the identifier "*" to indicate that this carbon atom is chiral. In embodiment no. 3, the configuration of this carbon atom is R. In embodiment no. 4, the configuration of this carbon atom is S.

In embodiment no. 5,
when $R^3$ is —CO$_2R^{3a}$, —CH$_2$CO$_2R^{3a}$, —CH$_2$CH$_2$CO$_2R^{3a}$, tetrazole, —C(O)N($R^{3b}$)$_2$, or —CH$_2$OH; then $R^4$ is H, halo, $C_1$-$C_6$ alkyl, —O—($C_1$-$C_3$ alkyl), or —N($R^{4b}$)$_2$, and $R^5$ is H or halo; and
when $R^4$ is —CO$_2R^{4a}$, —CH$_2$CO$_2R^{4a}$, —CH$_2$CH$_2$CO$_2R^{4a}$, tetrazole, —C(O)N($R^{4b}$)$_2$, or —CH$_2$OH; then $R^3$ is H, halo, $C_1$-$C_6$ alkyl, —O—($C_1$-$C_3$ alkyl), or —N($R^{3b}$)$_2$, and $R^5$ is H or halo, and
the remaining variables are as described in embodiment no. 1 or 2.

In embodiment no. 6,
when $R^3$ is —CO$_2R^{3a}$, —CH$_2$CO$_2R^{3a}$, —CH$_2$CH$_2$CO$_2R^{3a}$, tetrazole, C(O)N($R^{3b}$)$_2$, or —CH$_2$OH; then $R^4$ is H, and $R^5$ is H; and
when $R^4$ is —CO$_2R^{4a}$, —CH$_2$CO$_2R^{4a}$, —CH$_2$CH$_2$CO$_2R^{4a}$, tetrazole, —C(O)N($R^{4b}$)$_2$, or —CH$_2$OH; then $R^3$ and $R^5$ are H and,
the remaining variables are as described in embodiment no. 1 or 2.

In embodiment no. 7, $R^3$ is —CO$_2R^{3a}$, —CH$_2$CO$_2R^{3a}$, —CH$_2$CH$_2$CO$_2R^{3a}$, tetrazole, —C(O)NH$_2$, or —CH$_2$OH; and $R^4$ and $R^5$ are H, and the remaining variables are as described in embodiment no. 1 or 2.

In embodiment no. 8, $R^3$ is —CO$_2R^{3a}$, —CH$_2$CO$_2R^{3a}$, and —CH$_2$CH$_2$CO$_2R^{3a}$, and $R^4$ and $R^5$ are H, and the remaining variables are as described in embodiment no. 1.

In embodiment no. 9, $R^3$ is —CO$_2R^{3a}$, and $R^4$ and $R^5$ are H, and the remaining variables are as described in embodiment no. 1 or 2.

In embodiment no. 10, $R^3$, $R^4$, and $R^5$ are as described in embodiment no. 8 or 9, and $R^{3a}$ is H, and the remaining variables are as described in embodiment no. 1 or 2.

In embodiment no. 11, $R^5$ is H or fluoro, and the remaining variables are as described in any one embodiment nos. 1-5.

In embodiment no. 12, $R^6$ is selected from the group consisting of:
(i) $C_1$-$C_4$ alkyl;
(ii) $C_1$-$C_3$ fluoroalkyl;
(iii) —O—($C_1$-$C_6$ alkyl);
(iv) —$R^{6a}$, wherein $R^{6a}$ is selected from the group consisting of:
(a) $C_3$-$C_6$ cycloalkyl,
(b) a group of the formula

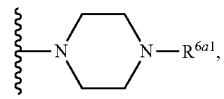

where $R^{6a1}$ is H or —CH$_2$CH$_2$NH$_2$; and
(c) a 5-membered heteroaryl containing 1 to 3 heteroatoms selected from the group consisting of N, O, and S;
wherein $R^{6a}$ is unsubstituted or substituted with 1 to 3 $R^{6a2}$ moieties selected from the group consisting of halo and $C_1$-$C_3$ alkyl;
(v) —O—$R^{6b}$; and
wherein $R^{6b}$ is selected from the group consisting of:
(a) $C_3$-$C_6$ cycloalkyl; and
(b) a group of the formula

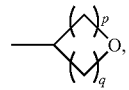

wherein p is 1 or 2, and q is 1 or 2; and
wherein $R^{6b}$ is unsubstituted, and the remaining variables are as described in any one of embodiment nos. 1-11.

In embodiment no. 13, $R^7$ is H or chloro, and the remaining variables are as described in any one of embodiment nos. 1-12.

In embodiment no. 14, one of $R^8$ and $R^9$ is halo and the other is H, and the remaining variables are as described in any one of embodiment nos. 1-13.

In embodiment no. 15, both $R^8$ and $R^9$ are H, and the remaining variables are as described in any one of embodiment nos. 1-13.

In embodiment no. 16, $R^2$ is OH and the remaining variables are as described in any one of embodiment nos. 1-15.

In embodiment no. 17, n is 1, and the remaining variables are as described in any one of embodiment nos. 1-16.

In embodiment no. 18, the compound of the Formula (I) has the Formula (IA)

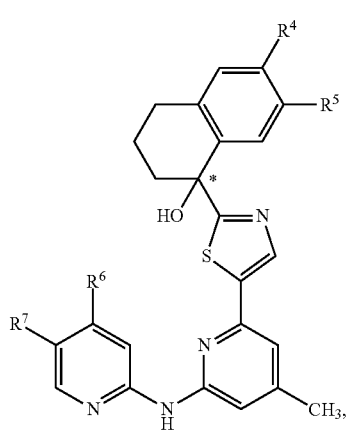

(IA)

wherein
$R^4$ is —CO$_2$R$^{4a}$, —C(O)NH$_2$, or —CH$_2$OH;
wherein $R^{4a}$ is selected from the group consisting of H and CH$_3$;
$R^5$ is H or fluoro;
$R^6$ is selected from the group consisting of:
(i) C$_1$-C$_4$ alkyl;
(ii) C$_1$-C$_3$ fluoroalkyl;
(iii) —O—(C$_1$-C$_6$ alkyl);
(iv) —R$^{6a}$, wherein R$^{6a}$ is selected from the group consisting of:
(a) C$_3$-C$_6$ cycloalkyl,
(b) a group of the formula

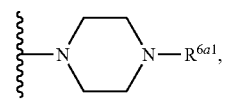

where $R^{6a1}$ is H or —CH$_2$CH$_2$NH$_2$; and
(c) a 5-membered heteroaryl containing 1 to 3 heteroatoms selected from the group consisting of N, O, and S (e.g., pyrazolyl, thienyl, and oxadiazolyl);
wherein $R^{6a}$ is unsubstituted or substituted with 1 to 3 $R^{6a2}$ moieties selected from the group consisting of halo and C$_1$-C$_3$ alkyl (e.g., methyl);

(v) —O—R$^{6b}$; and
wherein $R^{6b}$ is selected from the group consisting of:
(a) C$_3$-C$_6$ cycloalkyl; and
(b) a group of the formula

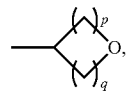

wherein p is 1 or 2, and q is 1 or 2;
wherein $R^{6b}$ is unsubstituted; and
$R^7$ is H or halo.

In embodiment no. 19, the compound has the Formula (IA), $R^4$ is —CO$_2$R$^{4a}$, wherein R$^{4a}$ is selected from the group consisting of H and CH$_3$, and the remaining variables are as described in embodiment no. 18.

In embodiment no. 20, the compound has the Formula (IA), $R^4$ is —CO$_2$H, and the remaining variables are as described in embodiment no. 18.

In embodiment no. 21, the compound has the Formula (IA), $R^6$ is selected from the group consisting of C$_1$-C$_4$ alkyl, —CF$_3$, —C(H)F$_2$, —O—(C$_1$-C$_3$ alkyl), —OCF$_3$, C$_3$-C$_6$ cycloalkyl,

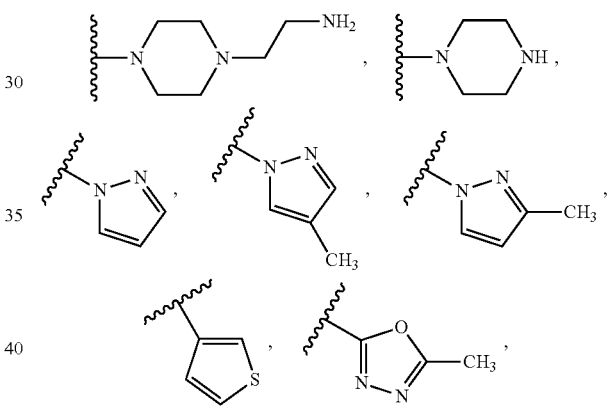

and —O—(C$_4$-C$_6$ cycloalkyl), and the remaining variables are as described in any one of embodiment nos. 18-20.

In embodiment, no. 22, the compound has the Formula (IA), $R^6$ is selected from the group consisting of C$_1$-C$_3$ fluoroalkyl, and the remaining variables are as described in any one of embodiment nos. 18-20.

In embodiment no. 23, the compound has the Formula (IA), $R^7$ is H or chloro, and the remaining variables are as described in any one of embodiment nos. 18-22.

In embodiment no. 24, the compound has the Formula (IA), $R^4$ is —CO$_2$R$^{4a}$, —C(O)NH$_2$, or —CH$_2$OH;
wherein $R^{4a}$ is selected from the group consisting of H and CH$_3$;
$R^5$ is H or fluoro;
$R^6$ is selected from the group consisting of C$_1$-C$_4$ alkyl, —CF$_3$, —C(H)F$_2$, —O—(C$_1$-C$_3$ alkyl), —OCF$_3$, C$_3$-C$_6$ cycloalkyl,

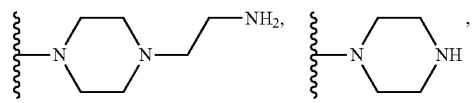

-continued

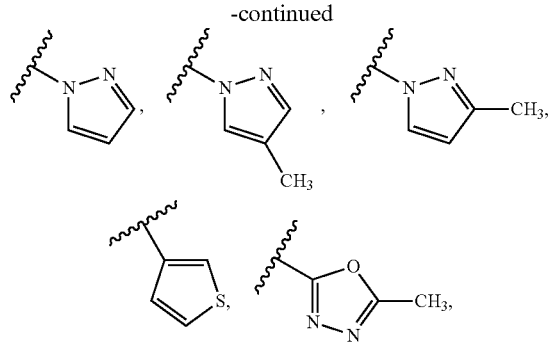

and —O—($C_4$-$C_6$ cycloalkyl); and
$R^7$ is H or chloro.

In embodiment no. 25, the compound has the Formula (IA), $R^4$ is —$CO_2R^{4a}$;
wherein $R^{4a}$ is selected from the group consisting of H and $CH_3$;
$R^5$ is H or fluoro;
$R^6$ is selected from the group consisting of $C_1$-$C_4$ alkyl, —$CF_3$, and —$C(H)F_2$; and
$R^7$ is H or chloro.

In embodiment no. 26, the compound has the Formula (I), $R^1$ is $C_1$-$C_3$ alkyl and the remaining variables are as described in embodiment no. 1.

In embodiment no. 27, the compound has the Formula (I), and one of $R^3$, $R^4$, and $R^5$ is selected from the group consisting of —$CO_2H$, —$C(O)$—CN, —$C(O)$—N(H)O$CH_3$, —P(O)(O$CH_2CH_3$)$_2$, —P(O)(OH)$_2$, tetrazole,

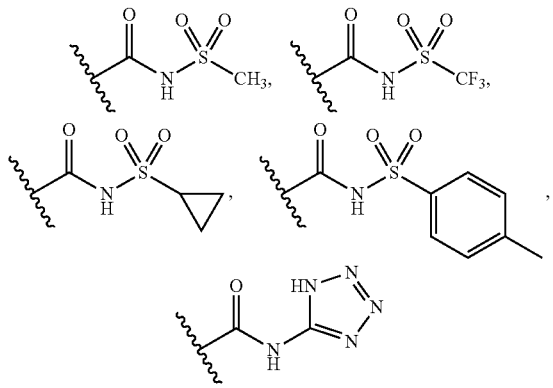

and
—B(OH)$_2$; and the other two of $R^3$, $R^4$, and $R^5$ are each H or halo;
and the remaining variables are as set forth in embodiment no. 1.

In embodiment no. 28, the compound has the Formula (I), wherein
$R^1$ is $C_1$-$C_3$ alkyl;
$R^2$ is —OH;
$R^6$ is $C_1$-$C_3$ fluoroalkyl;
$R^7$, $R^8$, and $R^9$ are each H;
$R^3$, $R^4$, and $R^5$ are as described in embodiment no. 27; and the remaining variables are as described in embodiment no. 1.

In embodiment no. 29, the compound has the Formula (IA), $R^6$ is selected from the group consisting of $C_1$-$C_4$ alkyl, —$CF_3$, —$C(H)F_2$, —O—($C_1$-$C_3$ alkyl), —$OCF_3$, $C_3$-$C_6$ cycloalkyl,

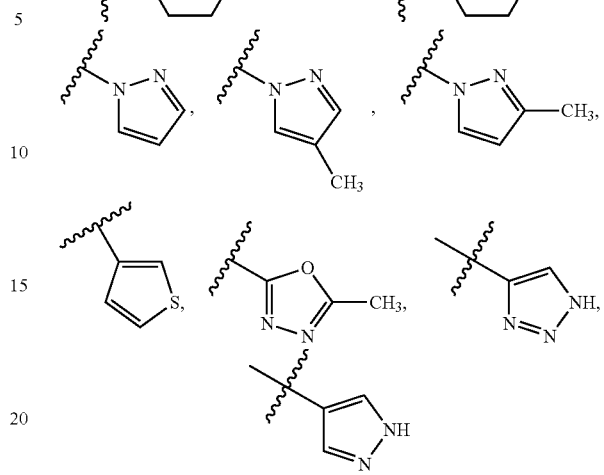

and —O—($C_4$-$C_6$ cycloalkyl), and the remaining variables are as described in any one of embodiment nos. 18-20.

In embodiment no. 30, the compound has the Formula (IA), $R^4$ is —$CO_2R^{4a}$, —$C(O)NH_2$, or —$CH_2OH$;
wherein $R^{4a}$ is selected from the group consisting of H and $CH_3$;
$R^5$ is H or fluoro;
$R^6$ is selected from the group consisting of $C_1$-$C_4$ alkyl, —$CF_3$, —$C(H)F_2$, —O—($C_1$-$C_3$ alkyl), —$OCF_3$, $C_3$-$C_6$ cycloalkyl,

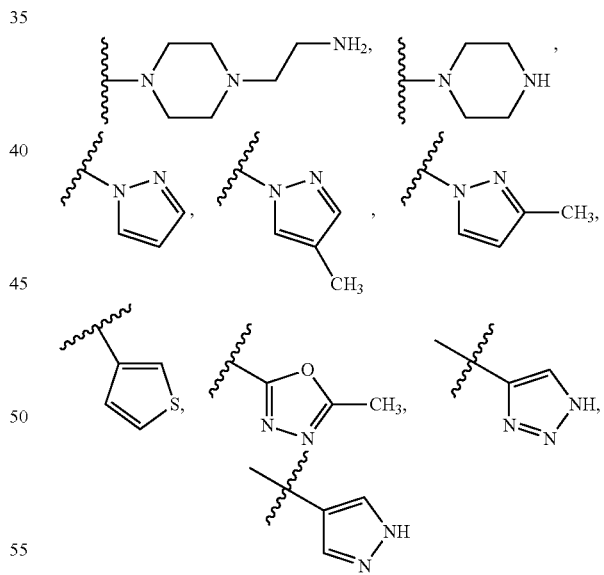

and —O—($C_4$-$C_6$ cycloalkyl); and
$R^7$ is H or chloro.

Representative compounds of the present invention are as follows, as well as pharmaceutically acceptable salts thereof:
5-(5-{6-[(4-tert-butoxypyridin-2-yl)amino]-4-methylpyridin-2-yl}-1,3-thiazol-2-yl)-5-hydroxy-5,6,7,8-tetrahydronaphthalene-2-carboxylic acid;
5-[5-(6-{[4-(difluoromethyl)pyridin-2-yl]amino}-4-methylpyridin-2-yl)-1,3-thiazol-2-yl]-5-hydroxy-5,6,7,8-tetrahydronaphthalene-2-carboxylic acid;

5-[5-(6-{[5-chloro-4-(trifluoromethyl)pyridin-2-yl]amino}-4-methylpyridin-2-yl)-1,3-thiazol-2-yl]-5-hydroxy-5,6,7,8-tetrahydronaphthalene-2-carboxylic acid;

5-{5-[6-({4-[4-(2-aminoethyl)piperazin-1-yl]pyridin-2-yl}amino)-4-methylpyridin-2-yl]-1,3-thiazol-2-yl}-5-hydroxy-5,6,7,8-tetrahydronaphthalene-2-carboxylic acid;

5-hydroxy-5-[5-(4-methyl-6-{[4-(piperazin-1-yl)pyridin-2-yl]amino}pyridin-2-yl)-1,3-thiazol-2-yl]-5,6,7,8-tetrahydronaphthalene-2-carboxylic acid;

5-hydroxy-5-[5-(4-methyl-6-{[4-(4-methyl-1H-pyrazol-1-yl)pyridin-2-yl]amino}pyridin-2-yl)-1,3-thiazol-2-yl]-5,6,7,8-tetrahydronaphthalene-2-carboxylic acid;

5-hydroxy-5-[5-(4-methyl-6-{[4-(1H-pyrazol-1-yl)pyridin-2-yl]amino}pyridin-2-yl)-1,3-thiazol-2-yl]-5,6,7,8-tetrahydronaphthalene-2-carboxylic acid;

5-hydroxy-5-[5-(4-methyl-6-{[4-(thiophen-3-yl)pyridin-2-yl]amino}pyridin-2-yl)-1,3-thiazol-2-yl]-5,6,7,8-tetrahydronaphthalene-2-carboxylic acid;

5-hydroxy-5-(5-{4-methyl-6-[(4-methylpyridin-2-yl)amino]pyridin-2-yl}-1,3-thiazol-2-yl)-5,6,7,8-tetrahydronaphthalene-2-carboxylic acid;

5-[5-(6-{[4-(cyclohexyloxy)pyridin-2-yl]amino}-4-methylpyridin-2-yl)-1,3-thiazol-2-yl]-5-hydroxy-5,6,7,8-tetrahydronaphthalene-2-carboxylic acid;

5-hydroxy-5-[5-(4-methyl-6-{[4-(3-methyl-1H-pyrazol-1-yl)pyridin-2-yl]amino}pyridin-2-yl)-1,3-thiazol-2-yl]-5,6,7,8-tetrahydronaphthalene-2-carboxylic acid;

5-(5-{6-[(4-cyclobutylpyridin-2-yl)amino]-4-methylpyridin-2-yl}-1,3-thiazol-2-yl)-5-hydroxy-5,6,7,8-tetrahydronaphthalene-2-carboxylic acid;

5-[5-(6-{[4-(cyclobutyloxy)pyridin-2-yl]amino}-4-methylpyridin-2-yl)-1,3-thiazol-2-yl]-5-hydroxy-5,6,7,8-tetrahydronaphthalene-2-carboxylic acid;

5-hydroxy-5-(5-{4-methyl-6-[(4-propylpyridin-2-yl)amino]pyridin-2-yl}-1,3-thiazol-2-yl)-5,6,7,8-tetrahydronaphthalene-2-carboxylic acid;

5-(5-{6-[(4-ethoxypyridin-2-yl)amino]-4-methylpyridin-2-yl}-1,3-thiazol-2-yl)-5-hydroxy-5,6,7,8-tetrahydronaphthalene-2-carboxylic acid;

5-[5-(6-{[4-(cyclopentyloxy)pyridin-2-yl]amino}-4-methylpyridin-2-yl)-1,3-thiazol-2-yl]-5-hydroxy-5,6,7,8-tetrahydronaphthalene-2-carboxylic acid;

5-(5-{6-[(4-ethylpyridin-2-yl)amino]-4-methylpyridin-2-yl}-1,3-thiazol-2-yl)-5-hydroxy-5,6,7,8-tetrahydronaphthalene-2-carboxylic acid;

5-(5-{6-[(4-cyclohexylpyridin-2-yl)amino]-4-methylpyridin-2-yl}-1,3-thiazol-2-yl)-5-hydroxy-5,6,7,8-tetrahydronaphthalene-2-carboxylic acid;

5-hydroxy-5-[5-(4-methyl-6-{[4-(propan-2-yloxy)pyridin-2-yl]amino}pyridin-2-yl)-1,3-thiazol-2-yl]-5,6,7,8-tetrahydronaphthalene-2-carboxylic acid;

5-hydroxy-5-[5-(4-methyl-6-{[4-(5-methyl-1,3,4-oxadiazol-2-yl)pyridin-2-yl]amino}pyridin-2-yl)-1,3-thiazol-2-yl]-5,6,7,8-tetrahydronaphthalene-2-carboxylic acid;

5-hydroxy-5-[5-(4-methyl-6-{[4-(tetrahydrofuran-3-yloxy)pyridin-2-yl]amino}pyridin-2-yl)-1,3-thiazol-2-yl]-5,6,7,8-tetrahydronaphthalene-2-carboxylic acid;

5-(5-{6-[(4-cyclopropylpyridin-2-yl)amino]-4-methylpyridin-2-yl}-1,3-thiazol-2-yl)-5-hydroxy-5,6,7,8-tetrahydronaphthalene-2-carboxylic acid;

5-hydroxy-5-[5-(4-methyl-6-{[4-(1-methylethyl)pyridin-2-yl]amino}pyridin-2-yl)-1,3-thiazol-2-yl]-5,6,7,8-tetrahydronaphthalene-2-carboxylic acid;

5-(5-{6-[(4-tert-butylpyridin-2-yl)amino]-4-methylpyridin-2-yl}-1,3-thiazol-2-yl)-5-hydroxy-5,6,7,8-tetrahydronaphthalene-2-carboxylic acid;

5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

methyl 5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

methyl 3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

7-fluoro-6-(hydroxymethyl)-1-[5-(4-methyl-6-{[4-(trifluoromethyl)pyridin-2-yl]amino}pyridin-2-yl)-1,3-thiazol-2-yl]-1,2,3,4-tetrahydronaphthalen-1-ol;

5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

methyl 5-hydroxy-5-[5-(4-methyl-6-{[4-(1H-1,2,3-triazol-4-yl)pyridin-2-yl]amino}pyridin-2-yl)-1,3-thiazol-2-yl]-5,6,7,8-tetrahydronaphthalene-2-carboxylate;

5-hydroxy-5-[5-(4-methyl-6-{[4-(1H-1,2,3-triazol-4-yl)pyridin-2-yl]amino}pyridin-2-yl)-1,3-thiazol-2-yl]-5,6,7,8-tetrahydronaphthalene-2-carboxylic acid;

5-[5-(3-bromo-4-methyl-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

5-[5-(5-bromo-4-methyl-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

5-[5-(3,5-dibromo-4-methyl-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

5-{5-[4-(acetylamino)-6-{[4-(trifluoromethyl)pyridin-2-yl]amino}pyridin-2-yl]-1,3-thiazol-2-yl}-5-hydroxy-5,6,7,8-tetrahydronaphthalene-2-carboxylic acid;

5-[5-(4-amino-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

methyl-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-1-carboxylate;

5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-1-carboxylic acid;

1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-4-carboxylic acid;

9-hydroxy-9-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-2-carboxylic acid;

5-hydroxy-5-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-2-carboxylic acid;

5-hydroxy-5-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-1-carboxylic acid;

3-hydroxy-3-[5-(4-methyl-6-{[4-(trifluoromethyl)pyridin-2-yl]amino}pyridin-2-yl)-1,3-thiazol-2-yl]-2,3-dihydro-1H-indene-5-carboxylic acid;

methyl 1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-5-carboxylate;

1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-5-carboxylic acid;

methyl 1-bromo-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

1-bromo-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

1-cyano-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

5-hydroxy-1-methoxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

6-bromo-1-[5-(4-methyl-6-{[4-(trifluoromethyl)pyridin-2-yl]amino}pyridin-2-yl)-1,3-thiazol-2-yl]-1,2,3,4-tetrahydronaphthalen-1-ol;

5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carbonitrile;

1-[5-(4-methyl-6-{[4-(trifluoromethyl)pyridin-2-yl]amino}pyridin-2-yl)-1,3-thiazol-2-yl]-6-(2H-tetrazol-5-yl)-1,2,3,4-tetrahydronaphthalen-1-ol;

5-hydroxy-N-(methylsulfonyl)-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

N-(cyclopropylsulfonyl)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

5-hydroxy-N-[(4-methylphenyl)sulfonyl]-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

N-cyano-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

5-hydroxy-5-[5-(4-methyl-6-{[4-(trifluoromethyl)pyridin-2-yl]amino}pyridin-2-yl)-1,3-thiazol-2-yl]-N-[(trifluoromethyl)sulfonyl]-5,6,7,8-tetrahydronaphthalene-2-carboxamide;

5-hydroxy-5-[5-(4-methyl-6-{[4-(trifluoromethyl)pyridin-2-yl]amino}pyridin-2-yl)-1,3-thiazol-2-yl]-N-1H-tetrazol-5-yl-5,6,7,8-tetrahydronaphthalene-2-carboxamide;

5-hydroxy-N-methoxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

diethyl {5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalen-2-yl}phosphonate;

{5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalen-2-yl}phosphonic acid;

{5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalen-2-yl}boronic acid;

methyl 5-fluoro-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

5-fluoro-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

5-amino-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

5-(acetylamino)-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

5-hydroxy-5-(5-{6-[(4-methoxypyridin-2-yl)amino]-4-methylpyridin-2-yl}-1,3-thiazol-2-yl)-5,6,7,8-tetrahydronaphthalene-2-carboxylic acid; and 5-hydroxy-5-(5-{4-methyl-6-[(4-propoxypyridin-2-yl)amino]pyridin-2-yl}-1,3-thiazol-2-yl)-5,6,7,8-tetrahydronaphthalene-2-carboxylic acid.

Additional representative compounds of the present invention are as follows, including the pharmaceutically acceptable salts thereof:

(5R)-5-(5-{6-[(4-tert-butoxypyridin-2-yl)amino]-4-methylpyridin-2-yl}-1,3-thiazol-2-yl)-5-hydroxy-5,6,7,8-tetrahydronaphthalene-2-carboxylic acid;

(5R)-5-[5-(6-{[4-(difluoromethyl)pyridin-2-yl]amino}-4-methylpyridin-2-yl)-1,3-thiazol-2-yl]-5-hydroxy-5,6,7,8-tetrahydronaphthalene-2-carboxylic acid;

(5R)-5-[5-(6-{[5-chloro-4-(trifluoromethyl)pyridin-2-yl]amino}-4-methylpyridin-2-yl)-1,3-thiazol-2-yl]-5-hydroxy-5,6,7,8-tetrahydronaphthalene-2-carboxylic acid;

(5R)-5-{5-[6-({4-[4-(2-aminoethyl)piperazin-1-yl]pyridin-2-yl}amino)-4-methylpyridin-2-yl]-1,3-thiazol-2-yl}-5-hydroxy-5,6,7,8-tetrahydronaphthalene-2-carboxylic acid;

(5R)-5-hydroxy-5-[5-(4-methyl-6-{[4-(piperazin-1-yl)pyridin-2-yl]amino}pyridin-2-yl)-1,3-thiazol-2-yl]-5,6,7,8-tetrahydronaphthalene-2-carboxylic acid;

(5R)-5-hydroxy-5-[5-(4-methyl-6-{[4-(4-methyl-1H-pyrazol-1-yl)pyridin-2-yl]amino}pyridin-2-yl)-1,3-thiazol-2-yl]-5,6,7,8-tetrahydronaphthalene-2-carboxylic acid;

(5R)-5-hydroxy-5-[5-(4-methyl-6-{[4-(1H-pyrazol-1-yl)pyridin-2-yl]amino}pyridin-2-yl)-1,3-thiazol-2-yl]-5,6,7,8-tetrahydronaphthalene-2-carboxylic acid;

(5R)-5-hydroxy-5-[5-(4-methyl-6-{[4-(thiophen-3-yl)pyridin-2-yl]amino}pyridin-2-yl)-1,3-thiazol-2-yl]-5,6,7,8-tetrahydronaphthalene-2-carboxylic acid;

(5R)-5-hydroxy-5-(5-{4-methyl-6-[(4-methylpyridin-2-yl)amino]pyridin-2-yl}-1,3-thiazol-2-yl)-5,6,7,8-tetrahydronaphthalene-2-carboxylic acid;

(5R)-5-[5-(6-{[4-(cyclohexyloxy)pyridin-2-yl]amino}-4-methylpyridin-2-yl)-1,3-thiazol-2-yl]-5-hydroxy-5,6,7,8-tetrahydronaphthalene-2-carboxylic acid;

(5R)-5-hydroxy-5-[5-(4-methyl-6-{[4-(3-methyl-1H-pyrazol-1-yl)pyridin-2-yl]amino}pyridin-2-yl)-1,3-thiazol-2-yl]-5,6,7,8-tetrahydronaphthalene-2-carboxylic acid;

(5R)-5-(5-{6-[(4-cyclobutylpyridin-2-yl)amino]-4-methylpyridin-2-yl}-1,3-thiazol-2-yl)-5-hydroxy-5,6,7,8-tetrahydronaphthalene-2-carboxylic acid;

(5R)-5-[5-(6-{[4-(cyclobutyloxy)pyridin-2-yl]amino}-4-methylpyridin-2-yl)-1,3-thiazol-2-yl]-5-hydroxy-5,6,7,8-tetrahydronaphthalene-2-carboxylic acid;

(5R)-5-hydroxy-5-(5-{4-methyl-6-[(4-propylpyridin-2-yl)amino]pyridin-2-yl}-1,3-thiazol-2-yl)-5,6,7,8-tetrahydronaphthalene-2-carboxylic acid;

(5R)-5-(5-{6-[(4-ethoxypyridin-2-yl)amino]-4-methylpyridin-2-yl}-1,3-thiazol-2-yl)-5-hydroxy-5,6,7,8-tetrahydronaphthalene-2-carboxylic acid;

(5R)-5-[5-(6-{[4-(cyclopentyloxy)pyridin-2-yl]amino}-4-methylpyridin-2-yl)-1,3-thiazol-2-yl]-5-hydroxy-5,6,7,8-tetrahydronaphthalene-2-carboxylic acid;

(5R)-5-(5-{6-[(4-ethylpyridin-2-yl)amino]-4-methylpyridin-2-yl}-1,3-thiazol-2-yl)-5-hydroxy-5,6,7,8-tetrahydronaphthalene-2-carboxylic acid;

(5R)-5-(5-{6-[(4-cyclohexylpyridin-2-yl)amino]-4-methylpyridin-2-yl}-1,3-thiazol-2-yl)-5-hydroxy-5,6,7,8-tetrahydronaphthalene-2-carboxylic acid;

(5R)-5-hydroxy-5-[5-(4-methyl-6-{[4-(propan-2-yloxy)pyridin-2-yl]amino}pyridin-2-yl)-1,3-thiazol-2-yl]-5,6,7,8-tetrahydronaphthalene-2-carboxylic acid;

(5R)-5-hydroxy-5-[5-(4-methyl-6-{[4-(5-methyl-1,3,4-oxa-diazol-2-yl)pyridin-2-yl]amino}pyridin-2-yl)-1,3-thiazol-2-yl]-5,6,7,8-tetrahydronaphthalene-2-carboxylic acid;

(5R)-5-hydroxy-5-[5-(4-methyl-6-{[4-(tetrahydrofuran-3-yloxy)pyridin-2-yl]amino}pyridin-2-yl)-1,3-thiazol-2-yl]-5,6,7,8-tetrahydronaphthalene-2-carboxylic acid;

(5R)-5-(5-{6-[(4-cyclopropylpyridin-2-yl)amino]-4-methylpyridin-2-yl}-1,3-thiazol-2-yl)-5-hydroxy-5,6,7,8-tetrahydronaphthalene-2-carboxylic acid;

(5R)-5-hydroxy-5-[5-(4-methyl-6-{[4-(1-methylethyl)pyridin-2-yl]amino}pyridin-2-yl)-1,3-thiazol-2-yl]-5,6,7,8-tetrahydronaphthalene-2-carboxylic acid;

(5R)-5-(5-{6-[(4-tert-butylpyridin-2-yl)amino]-4-methylpyridin-2-yl}-1,3-thiazol-2-yl)-5-hydroxy-5,6,7,8-tetrahydronaphthalene-2-carboxylic acid;

(5R)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(5R)-methyl 5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

(5R)-methyl 3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

(5R)-3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(5R)-7-fluoro-6-(hydroxymethyl)-1-[5-(4-methyl-6-{[4-(trifluoromethyl)pyridin-2-yl]amino}pyridin-2-yl)-1,3-thiazol-2-yl]-1,2,3,4-tetrahydronaphthalen-1-ol;

(5R)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

(5R)-methyl 5-hydroxy-5-[5-(4-methyl-6-{[4-(1H-1,2,3-triazol-4-yl)pyridin-2-yl]amino}pyridin-2-yl)-1,3-thiazol-2-yl]-5,6,7,8-tetrahydronaphthalene-2-carboxylate;

(5R)-5-hydroxy-5-[5-(4-methyl-6-{[4-(1H-1,2,3-triazol-4-yl)pyridin-2-yl]amino}pyridin-2-yl)-1,3-thiazol-2-yl]-5,6,7,8-tetrahydronaphthalene-2-carboxylic acid;

(5R)-5-[5-(3-bromo-4-methyl-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

(5R)-5-[5-(5-bromo-4-methyl-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

(5R)-5-[5-(3,5-dibromo-4-methyl-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

(5R)-5-{5-[4-(acetylamino)-6-{[4-(trifluoromethyl)pyridin-2-yl]amino}pyridin-2-yl]-1,3-thiazol-2-yl}-5-hydroxy-5,6,7,8-tetrahydronaphthalene-2-carboxylic acid;

(5R)-5-[5-(4-amino-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

(5R)-methyl-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-1-carboxylate;

(5R)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-1-carboxylic acid;

(5R)-1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-4-carboxylic acid;

(9R)-9-hydroxy-9-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-2-carboxylic acid;

(5R)-5-hydroxy-5-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-2-carboxylic acid;

(5R)-5-hydroxy-5-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-1-carboxylic acid;

(3R)-3-hydroxy-3-[5-(4-methyl-6-{[4-(trifluoromethyl)pyridin-2-yl]amino}pyridin-2-yl)-1,3-thiazol-2-yl]-2,3-dihydro-1H-indene-5-carboxylic acid;

(1R)-methyl 1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-5-carboxylate;

(1R)-1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-5-carboxylic acid;

(5R)-methyl 1-bromo-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

(5R)-1-bromo-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(5R)-1-cyano-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(5R)-5-hydroxy-1-methoxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(1R)-6-bromo-1-[5-(4-methyl-6-{[4-(trifluoromethyl)pyridin-2-yl]amino}pyridin-2-yl)-1,3-thiazol-2-yl]-1,2,3,4-tetrahydronaphthalen-1-ol;

(5R)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carbonitrile;

(1R)-1-[5-(4-methyl-6-{[4-(trifluoromethyl)pyridin-2-yl]amino}pyridin-2-yl)-1,3-thiazol-2-yl]-6-(2H-tetrazol-5-yl)-1,2,3,4-tetrahydronaphthalen-1-ol;

(5R)-5-hydroxy-N-(methylsulfonyl)-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

(5R)—N-(cyclopropylsulfonyl)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

(5R)-5-hydroxy-N-[(4-methylphenyl)sulfonyl]-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

(5R)—N-cyano-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

(5R)-5-hydroxy-5-[5-(4-methyl-6-{[4-(trifluoromethyl)pyridin-2-yl]amino}pyridin-2-yl)-1,3-thiazol-2-yl]-N-[(trifluoromethyl)sulfonyl]-5,6,7,8-tetrahydronaphthalene-2-carboxamide;

(5R)-5-hydroxy-5-[5-(4-methyl-6-{[4-(trifluoromethyl)pyridin-2-yl]amino}pyridin-2-yl)-1,3-thiazol-2-yl]-N-1H-tetrazol-5-yl-5,6,7,8-tetrahydronaphthalene-2-carboxamide;

(5R)-5-hydroxy-N-methoxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

diethyl {(5R)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalen-2-yl}phosphonate;

{(5R)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalen-2-yl}phosphonic acid;

{(5R)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalen-2-yl}boronic acid;

(5R)-methyl 5-fluoro-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

(5R)-5-fluoro-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(5R)-5-amino-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(5R)-5-(acetylamino)-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(5R)-5-hydroxy-5-(5-{6-[(4-methoxypyridin-2-yl)amino]-4-methylpyridin-2-yl}-1,3-thiazol-2-yl)-5,6,7,8-tetrahydronaphthalene-2-carboxylic acid; and (5R)-5-hydroxy-5-(5-{4-methyl-6-[(4-propoxypyridin-2-yl)amino]pyridin-2-yl}-1,3-thiazol-2-yl)-5,6,7,8-tetrahydronaphthalene-2-carboxylic acid.

Additional representative compounds of the present invention are as follows, including the pharmaceutically acceptable salts thereof:

(5S)-5-(5-{6-[(4-tert-butoxypyridin-2-yl)amino]-4-methylpyridin-2-yl}-1,3-thiazol-2-yl)-5-hydroxy-5,6,7,8-tetrahydronaphthalene-2-carboxylic acid;

(5S)-5-[5-(6-{[4-(difluoromethyl)pyridin-2-yl]amino}-4-methylpyridin-2-yl)-1,3-thiazol-2-yl]-5-hydroxy-5,6,7,8-tetrahydronaphthalene-2-carboxylic acid;

(5S)-5-[5-(6-{[5-chloro-4-(trifluoromethyl)pyridin-2-yl]amino}-4-methylpyridin-2-yl)-1,3-thiazol-2-yl]-5-hydroxy-5,6,7,8-tetrahydronaphthalene-2-carboxylic acid;

(5S)-5-{5-[6-({4-[4-(2-aminoethyl)piperazin-1-yl]pyridin-2-yl}amino)-4-methylpyridin-2-yl]-1,3-thiazol-2-yl}-5-hydroxy-5,6,7,8-tetrahydronaphthalene-2-carboxylic acid;

(5S)-5-hydroxy-5-[5-(4-methyl-6-{[4-(piperazin-1-yl)pyridin-2-yl]amino}pyridin-2-yl)-1,3-thiazol-2-yl]-5,6,7,8-tetrahydronaphthalene-2-carboxylic acid;

(5S)-5-hydroxy-5-[5-(4-methyl-6-{[4-(4-methyl-1H-pyrazol-1-yl)pyridin-2-yl]amino}pyridin-2-yl)-1,3-thiazol-2-yl]-5,6,7,8-tetrahydronaphthalene-2-carboxylic acid;

(5S)-5-hydroxy-5-[5-(4-methyl-6-{[4-(1H-pyrazol-1-yl)pyridin-2-yl]amino}pyridin-2-yl)-1,3-thiazol-2-yl]-5,6,7,8-tetrahydronaphthalene-2-carboxylic acid;

(5S)-5-hydroxy-5-[5-(4-methyl-6-{[4-(thiophen-3-yl)pyridin-2-yl]amino}pyridin-2-yl)-1,3-thiazol-2-yl]-5,6,7,8-tetrahydronaphthalene-2-carboxylic acid;

(5S)-5-hydroxy-5-(5-{4-methyl-6-[(4-methylpyridin-2-yl)amino]pyridin-2-yl}-1,3-thiazol-2-yl)-5,6,7,8-tetrahydronaphthalene-2-carboxylic acid;

(5S)-5-[5-(6-{[4-(cyclohexyloxy)pyridin-2-yl]amino}-4-methylpyridin-2-yl)-1,3-thiazol-2-yl]-5-hydroxy-5,6,7,8-tetrahydronaphthalene-2-carboxylic acid;

(5S)-5-hydroxy-5-[5-(4-methyl-6-{[4-(3-methyl-1H-pyrazol-1-yl)pyridin-2-yl]amino}pyridin-2-yl)-1,3-thiazol-2-yl]-5,6,7,8-tetrahydronaphthalene-2-carboxylic acid;

(5S)-5-(5-{6-[(4-cyclobutylpyridin-2-yl)amino]-4-methylpyridin-2-yl}-1,3-thiazol-2-yl)-5-hydroxy-5,6,7,8-tetrahydronaphthalene-2-carboxylic acid;

(5S)-5-[5-(6-{[4-(cyclobutyloxy)pyridin-2-yl]amino}-4-methylpyridin-2-yl)-1,3-thiazol-2-yl]-5-hydroxy-5,6,7,8-tetrahydronaphthalene-2-carboxylic acid;

(5S)-5-hydroxy-5-(5-{4-methyl-6-[(4-propylpyridin-2-yl)amino]pyridin-2-yl}-1,3-thiazol-2-yl)-5,6,7,8-tetrahydronaphthalene-2-carboxylic acid;

(5S)-5-(5-{6-[(4-ethoxypyridin-2-yl)amino]-4-methylpyridin-2-yl}-1,3-thiazol-2-yl)-5-hydroxy-5,6,7,8-tetrahydronaphthalene-2-carboxylic acid;

(5S)-5-[5-(6-{[4-(cyclopentyloxy)pyridin-2-yl]amino}-4-methylpyridin-2-yl)-1,3-thiazol-2-yl]-5-hydroxy-5,6,7,8-tetrahydronaphthalene-2-carboxylic acid;

(5S)-5-(5-{6-[(4-ethylpyridin-2-yl)amino]-4-methylpyridin-2-yl}-1,3-thiazol-2-yl)-5-hydroxy-5,6,7,8-tetrahydronaphthalene-2-carboxylic acid;

(5S)-5-(5-{6-[(4-cyclohexylpyridin-2-yl)amino]-4-methylpyridin-2-yl}-1,3-thiazol-2-yl)-5-hydroxy-5,6,7,8-tetrahydronaphthalene-2-carboxylic acid;

(5S)-5-hydroxy-5-[5-(4-methyl-6-{[4-(propan-2-yloxy)pyridin-2-yl]amino}pyridin-2-yl)-1,3-thiazol-2-yl]-5,6,7,8-tetrahydronaphthalene-2-carboxylic acid;

(5S)-5-hydroxy-5-[5-(4-methyl-6-{[4-(5-methyl-1,3,4-oxadiazol-2-yl)pyridin-2-yl]amino}pyridin-2-yl)-1,3-thiazol-2-yl]-5,6,7,8-tetrahydronaphthalene-2-carboxylic acid;

(5S)-5-hydroxy-5-[5-(4-methyl-6-{[4-(tetrahydrofuran-3-yloxy)pyridin-2-yl]amino}pyridin-2-yl)-1,3-thiazol-2-yl]-5,6,7,8-tetrahydronaphthalene-2-carboxylic acid;

(5S)-5-(5-{6-[(4-cyclopropylpyridin-2-yl)amino]-4-methylpyridin-2-yl}-1,3-thiazol-2-yl)-5-hydroxy-5,6,7,8-tetrahydronaphthalene-2-carboxylic acid;

(5S)-5-hydroxy-5-[5-(4-methyl-6-{[4-(1-methylethyl)pyridin-2-yl]amino}pyridin-2-yl)-1,3-thiazol-2-yl]-5,6,7,8-tetrahydronaphthalene-2-carboxylic acid;

(5S)-5-(5-{6-[(4-tert-butylpyridin-2-yl)amino]-4-methylpyridin-2-yl}-1,3-thiazol-2-yl)-5-hydroxy-5,6,7,8-tetrahydronaphthalene-2-carboxylic acid;

(5S)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(5S)-methyl 5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

(5S)-methyl 3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

(5S)-3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(5S)-7-fluoro-6-(hydroxymethyl)-1-[5-(4-methyl-6-{[4-(trifluoromethyl)pyridin-2-yl]amino}pyridin-2-yl)-1,3-thiazol-2-yl]-1,2,3,4-tetrahydronaphthalen-1-ol;

(5S)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

(5S)-methyl 5-hydroxy-5-[5-(4-methyl-6-{[4-(1H-1,2,3-triazol-4-yl)pyridin-2-yl]amino}pyridin-2-yl)-1,3-thiazol-2-yl]-5,6,7,8-tetrahydronaphthalene-2-carboxylate;

(5S)-5-hydroxy-5-[5-(4-methyl-6-{[4-(1H-1,2,3-triazol-4-yl)pyridin-2-yl]amino}pyridin-2-yl)-1,3-thiazol-2-yl]-5,6,7,8-tetrahydronaphthalene-2-carboxylic acid;

(5S)-5-[5-(3-bromo-4-methyl-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

(5S)-5-[5-(5-bromo-4-methyl-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

(5S)-5-[5-(3,5-dibromo-4-methyl-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

(5S)-5-{5-[4-(acetylamino)-6-{[4-(trifluoromethyl)pyridin-2-yl]amino}pyridin-2-yl]-1,3-thiazol-2-yl}-5-hydroxy-5,6,7,8-tetrahydronaphthalene-2-carboxylic acid;

(5S)-5-[5-(4-amino-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

(5S)-methyl-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-1-carboxylate;

(5S)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-1-carboxylic acid;

(5S)-1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-4-carboxylic acid;

(9S)-9-hydroxy-9-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-2-carboxylic acid;

(5S)-5-hydroxy-5-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-2-carboxylic acid;

(5S)-5-hydroxy-5-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-1-carboxylic acid;

(3S)-3-hydroxy-3-[5-(4-methyl-6-{[4-(trifluoromethyl)pyridin-2-yl]amino}pyridin-2-yl)-1,3-thiazol-2-yl]-2,3-dihydro-1H-indene-5-carboxylic acid;

(1S)-methyl 1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-5-carboxylate;

(1S)-1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-5-carboxylic acid;

(5S)-methyl 1-bromo-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

(5S)-1-bromo-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(5S)-1-cyano-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(5S)-5-hydroxy-1-methoxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(1S)-6-bromo-1-[5-(4-methyl-6-{[4-(trifluoromethyl)pyridin-2-yl]amino}pyridin-2-yl)-1,3-thiazol-2-yl]-1,2,3,4-tetrahydronaphthalen-1-ol;

(5S)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carbonitrile;

(1S)-1-[5-(4-methyl-6-{[4-(trifluoromethyl)pyridin-2-yl]amino}pyridin-2-yl)-1,3-thiazol-2-yl]-6-(2H-tetrazol-5-yl)-1,2,3,4-tetrahydronaphthalen-1-ol;

(5S)-5-hydroxy-N-(methylsulfonyl)-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

(5S)—N-(cyclopropylsulfonyl)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

(5S)-5-hydroxy-N-[(4-methylphenyl)sulfonyl]-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

(5S)—N-cyano-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

(5S)-5-hydroxy-5-[5-(4-methyl-6-{[4-(trifluoromethyl)pyridin-2-yl]amino}pyridin-2-yl)-1,3-thiazol-2-yl]-N-[(trifluoromethyl)sulfonyl]-5,6,7,8-tetrahydronaphthalene-2-carboxamide;

(5S)-5-hydroxy-5-[5-(4-methyl-6-{[4-(trifluoromethyl)pyridin-2-yl]amino}pyridin-2-yl)-1,3-thiazol-2-yl]-N-1H-tetrazol-5-yl-5,6,7,8-tetrahydronaphthalene-2-carboxamide;

(5S)-5-hydroxy-N-methoxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

diethyl {(5S)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalen-2-yl}phosphonate;

{(5S)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalen-2-yl}phosphonic acid;

{(5S)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalen-2-yl}boronic acid;

(5S)-methyl 5-fluoro-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

(5S)-5-fluoro-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(5S)-5-amino-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(5S)-5-(acetylamino)-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

(5S)-5-hydroxy-5-(5-{6-[(4-methoxypyridin-2-yl)amino]-4-methylpyridin-2-yl}-1,3-thiazol-2-yl)-5,6,7,8-tetrahydronaphthalene-2-carboxylic acid; and (5S)-5-hydroxy-5-(5-{4-methyl-6-[(4-propoxypyridin-2-yl)amino]pyridin-2-yl}-1,3-thiazol-2-yl)-5,6,7,8-tetrahydronaphthalene-2-carboxylic acid.

The invention also provides a compound of Formula (I) or a pharmaceutically acceptable salt thereof in purified form.

Uses of the Compounds

Compounds of Formula (I) or its pharmaceutically acceptable salts and pharmaceutical compositions containing such compounds can be used to treat or prevent a variety of conditions or diseases mediated by Spleen tyrosine kinase (Syk). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g., precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors) myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, vascular spasms, migraine, reperfusion injury, and post-myocardial infarction.

The invention thus provides compounds of Formula (I) and pharmaceutically acceptable salts thereof for use in therapy, and particularly in the treatment of diseases and conditions mediated by inappropriate Syk activity. The inappropriate Syk activity referred to herein is any Syk activity that deviates from the normal Syk activity expected in a particular patient. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk for the prevention and/or treatment of disorders related to unregulated Syk activity.

In a further embodiment, the present invention provides a method of treatment of a patient suffering from a disorder mediated by Syk activity, which comprises administering to said patient an effective amount of a compound of Formula (I) or a pharmaceutically acceptable salt, solvate, or a physiologically functional derivative thereof. In a further embodiment, the present invention provides for the use of a compound of Formula (I), or a pharmaceutically acceptable salt or solvate thereof, or a physiologically functional derivative thereof, in the preparation of a medicament for the treatment of a disorder mediated by Syk activity.

In a further embodiment said disorder mediated by Syk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Syk is known to play a critical role in immunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

Compositions and Administration

While it is possible that, for use in therapy, a compound of Formula (I), as well as pharmaceutically acceptable salts thereof, may be administered as the raw chemical, it is possible to present the active ingredient as a pharmaceutical composition. Accordingly, the invention further provides a pharmaceutical composition, which comprises a compound of Formula (I) and pharmaceutically acceptable salts thereof, and a pharmaceutically acceptable carrier. The compounds of the Formula (I) and pharmaceutically acceptable salts thereof, are as described above. The carriers must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula (I), or a pharmaceutically acceptable salt thereof, with one or more pharmaceutically acceptable carriers.

Pharmaceutical compositions of the present invention may be presented in unit dose forms containing a predetermined amount of active ingredient per unit dose. Such a unit may contain, for example, 5 µg to 1 g, preferably 1 mg to 700 mg, more preferably 5 mg to 100 mg of a compound of the Formula (I), depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, or parenteral (including intravenous and intramuscular) route. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, COPD or ARDS.

In a further embodiment, the present invention provides a pharmaceutical composition adapted for administration by the inhaled route, for treating, for example, asthma or COPD.

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula (I) and pharmaceutically acceptable salts thereof can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula (I) is in a particle-size-reduced form, and more preferably the size-reduced form is obtained or obtainable by micronisation. The preferable particle size of the size-reduced (e.g., micronised) compound or salt or solvate is defined by a D50 value of about 0.5 to about 10 microns (for example as measured using laser diffraction).

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula (I) or salt or solvate thereof (preferably in particle-size-reduced form, e.g., in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula (I) or salt thereof. The lactose is preferably lactose hydrate e.g., lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g., 10-1000 microns e.g., 30-1000 microns) in diameter, and/or 50% or more of the lactose particles being less than 500 microns (e.g., 10-500 microns) in diameter. More preferably, the particle size of the lactose is defined by 90% or more of the lactose particles being less than 300 microns (e.g., 10-300 microns e.g., 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g., about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurised aerosols, nebulizers or insufflators.

For pharmaceutical compositions suitable and/or adapted for intranasal administration, the compound of Formula (I) or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The following are examples of representative pharmaceutical dosage forms for the compounds of this invention:

| Injectable Suspension (I.M.) | mg/mL |
|---|---|
| Compound of Formula (I) | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula (I) | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula (I) | 25 |
| Lactose Powder | 573.5 |
| Magnesium Stearate | 1.5 |
| | 600 |

| Aerosol | Per canister |
|---|---|
| Compound of Formula (I) | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of Formula (I) for the treatment of diseases or conditions associated with inappropriate Syk activity, will generally be in the range of 5 µg to 100 mg/kg body weight of recipient (patient) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula (I) per se.

The compositions of the invention can further comprise one or more additional therapeutic agents, as discussed in further detail below. Accordingly, in one embodiment, the present invention provides compositions comprising: (i) a compound of Formula (I) or a pharmaceutically acceptable salt thereof; (ii) one or more additional therapeutic agents, that are not compounds of Formula (I); and (iii) a pharmaceutically acceptable carrier, wherein the amounts in the composition are together effective to treat one of the disease or conditions discussed above.

Combination Therapy

The compounds of Formula (I) or their pharmaceutically acceptable salts may be used in combination, either in a single formulation or co-administered as separate formulations with at least one additional therapeutic agent to treat or prevent the diseases and conditions described herein. These additional therapeutic agents include, but are not limited to: (1) a DP receptor antagonist, such as S-5751 and laropiprant; (2) a corticosteroid, such as triamcinolone acetonide, budesonide, beclomethasone, fluticasone and mometasone; (3) a β2-adrenergic agonist, such as salmeterol, formoterol, arformoterol, terbutaline, metaproterenol, albuterol and the like; (4) a leukotriene modifier, including a leukotriene receptor antagonist, such as montelukast, zafirlukast, pranlukast, or a lipooxygenase inhibitor including 5-lipooxygenase inhibitors and FLAP (5-lipooxygenase activating protein) inhibitors, such as zileuton; (5) an antihistamine such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (6) a decongestant, including phenylephrine, phenylpropanolamine, pseudophedrine, oxymetazoline, ephinephrine, naphazoline, xylometazoline, propylhexedrine, or levo-desoxyephedrine; (7) an antiitussive, including codeine, hydrocodone, caramiphen, carbetapentane, or dextramethorphan; (8) another prostaglandin ligand, including prostaglandin F agonist such as latanoprost; misoprostol, enprostil, rioprostil, ornoprostol or rosaprostol; (9) a diuretic; (10) non-steroidal antiinflammatory agents (NSAIDs), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors, such as celecoxib and rofecoxib; (12) inhibitors of phosphodiesterase type IV (PDE-IV) e.g., Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents, such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists, such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin D2 mediated diseases comprising: administration to a patient in need of such treatment a nontoxic therapeutically effective amount of a compound of Formula (I), optionally co-administered with one or more of such ingredients as listed immediately above.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

In one embodiment, the compound of Formula (I) is administered during a time when the additional therapeutic agent(s) exert their prophylactic or therapeutic effect, or vice versa.

In another embodiment, the compound of Formula (I) and the additional therapeutic agent(s) are administered in doses commonly employed when such agents are used as monotherapy for treating the disorder.

In another embodiment, the compound of Formula (I) and the additional therapeutic agent(s) are administered in doses lower than the doses commonly employed when such agents are used as monotherapy for treating the disorder.

In one embodiment, the compound of Formula (I) and the additional therapeutic agent(s) are present in the same composition, which is suitable for oral administration.

The compound of Formula (I) and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

The doses and dosage regimen of the additional therapeutic agent(s) used in the combination therapies of the present invention for the treatment or prevention of a disease or disorder can be determined by the attending clinician, taking into consideration the approved doses and dosage regimen in the package insert; the age, sex and general health of the patient; and the type and severity of the viral infection or related disease or disorder.

Another aspect of this invention is a kit comprising a therapeutically effective amount of the compound of Formula (I) or a pharmaceutically acceptable salt of said compound, optionally at least one additional therapeutic agent listed above and a pharmaceutically acceptable carrier, vehicle or diluent.

Methods of Preparing the Compounds of Formula (I)

The compounds of this invention may be made by a variety of methods, including standard chemistry. Any previously defined variable will continue to have the previously defined meaning unless otherwise indicated. Illustrative general synthetic methods are set out below and then specific compounds of the Formula (I) are prepared in the Examples.

Compounds of general Formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of Formula (I). Those skilled in the art will recognize whether a stereocenter exists in compounds of Formula (I). Accordingly, the present invention includes all possible stereoisomers and includes not only mixtures of stereoisomers (such as racemic compounds) but the individual stereoisomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following solvents, reagents, protecting groups, moieties, and other designations may be referred to by their abbreviations in parenthesis:

Me=methyl; Et=ethyl; Pr=propyl; iPr=isopropyl, Bu=butyl; t-Bu=tert-butyl; Ph=phenyl, and Ac=acetyl µl=microliters
AcOH or HOAc=acetic acid
ACN=acetonitrile
Ad=adamantyl
aq=aqueous
Bn=benzyl
Boc or BOC=tert-butoxycarbonyl
Bz=benzoyl
Boc=tert-butoxycarbonyl
Cbz=benyzloxycarbonyl
Dba=dibenzylideneacetone
DBU=1,8-Diaza-7-bicyclo[5.4.0]undecene
DCM=dichloromethane:
DMAP=4-Dimethylaminopyridine
DIBAL=diisobutylaluminum hydride
DIEA or Hünig's Base=N,N-diisopropylethylamine
DMA=1,2-dimethylacetamide
DMF=dimethylformamide
DMSO=dimethyl sulfoxide
DTT=dithiothreitol
EDTA=ethylenediamine tetraacetic acid
EtOAc=ethyl acetate
g=grams
GST=glutathione S-transferase
h=hour
HMDS=1,1,1,3,3,3-hexamethyldisilazane
HATU=N,N,N',N'-tetramethyl-O-(7-azabenzotriazol-1-yl)uronium hexafluorophosphate
HPLC=high-performance liquid chromatography
HOBt=1-hydroxybenzotriazole
LDA=lithium diisopropylamide
LCMS=liquid chromatography mass spectrometry
min=minute
mg=milligrams
mL=milliliters
mmol=millimoles
Me=methyl
MeOH: methanol
MS=mass spectrometry
MTBE=methyl t-butyl ether
NBS=N-bromosuccimide
NMR=nuclear magnetic resonance spectroscopy
PMB=4-methoxy benzyl
rac=racemic mixture
RT or rt=room temperature (ambient, about 25° C.)
sat=saturated
SFC=supercritical fluid chromatography
TBSCl=t-butyldimethylsilyl chloride
TBS=t-butyldimethyl silyl
TEA=triethylamine (Et₃N)
TFA=trifluoroacetic acid
TFAA=trifluoroacetic anhydride
THF=tetrahydrofuran
TLC=thin layer chromatography
TMS=trimethylsilyl
Tris=tris(hydroxymethyl)aminomethane
Xantphos=4,5-Bis(diphenylphosphino)-9,9-dimethylxanthene General Methods As shown in Scheme 1, compounds of Formula (I) can be prepared by Heck coupling between bromo-substituted aminopyridines (S2) and substituted thiazoles (S1). The resulting intermediates, after deprotection, (S3) can then be reacted with substituted bromo- or chloropyridines (S4), and the ester moiety can be hydrolyzed using alkali metal hydroxides to provide the carboxylic acids (S5).

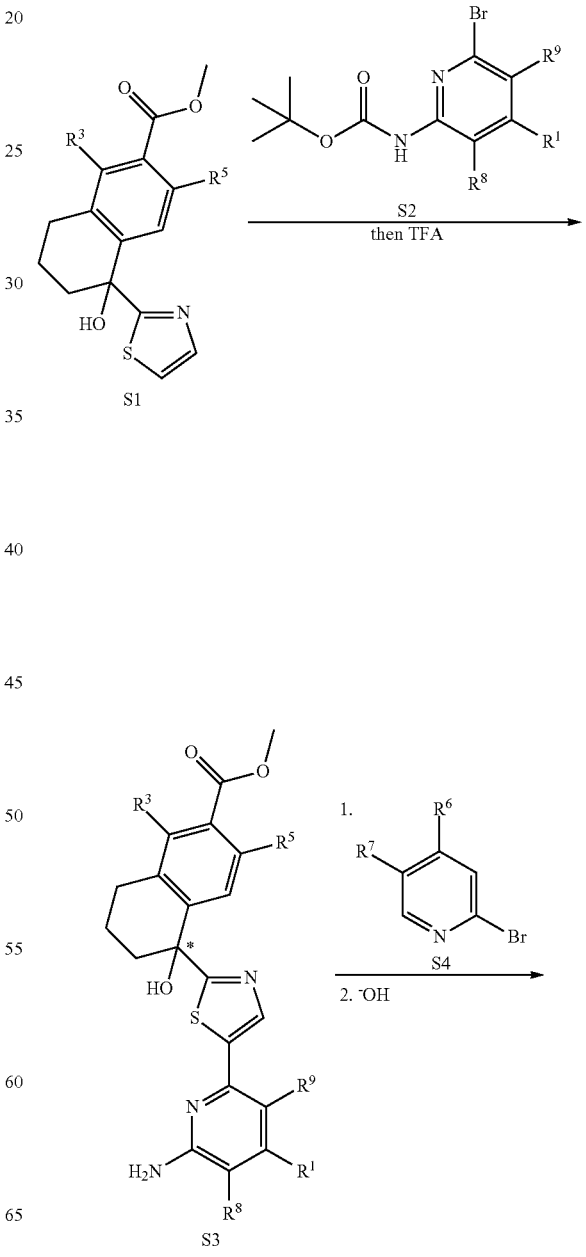

Scheme I

-continued

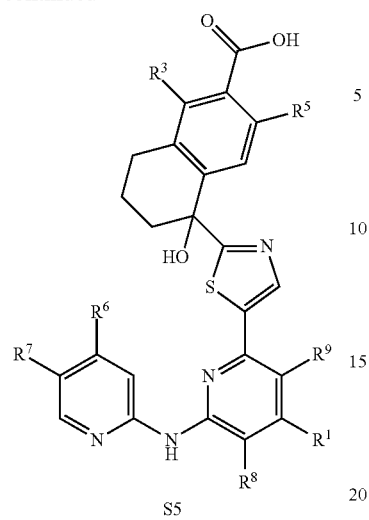

S5

Bromo-substituted aminopyridines (S2) can be prepared by reaction between dibromopyridines (S2a) and tent-butyl carbamate (S2b) as shown in Scheme II.

Scheme II

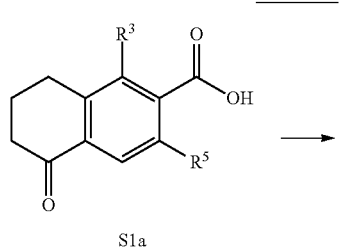

Substituted thiazoles (S1) can be prepared by esterification of 5-oxo tetrahydronaphthalene-2-carboxylic acids (S1a), followed by a Grignard reaction with thiazole as shown in Scheme III. If desired, the substituted thiazoles (S1) may be resolved into purified enantiomers, S1c and S1d, by using, for example, chiral chromatography.

Scheme III

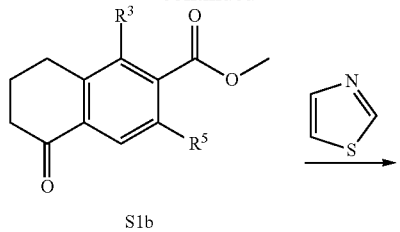

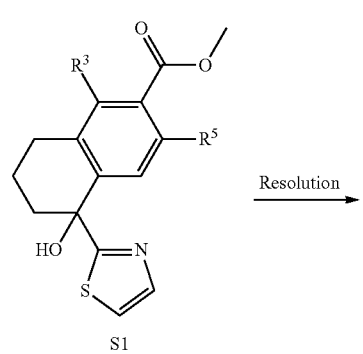

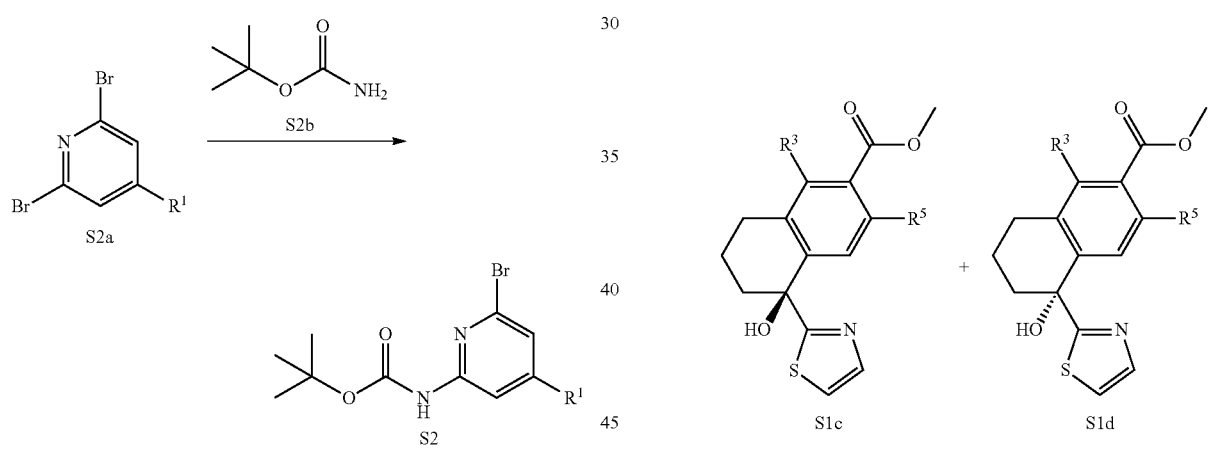

The starting materials and reagents used in preparing compounds described are either available from commercial suppliers or were prepared by literature methods known to those skilled in the art. For instance, 5-oxo-5,6,7,8-tetrahydronaphthalene-2-carboxylic acid, an example of an S1a, is available from Matrix Scientific (Colombia, S.C.). 1-Oxo-2,3-dihydro-1H-indene-5-carboxylic acid is available from DL Chiral Chemicals (Princeton, N.J.). The synthesis of 5-oxo-6,7,8,9-tetrahydro-5H-benzo[7]annulene-2-carboxylic acid is described in *J. Org. Chem,* 1962, 27(1), 70-76. 2,6-Dibromo-4-methylpyridine, an example of S2a, can be purchased from Aces Pharma (Branford, Conn.).

These examples are being provided to further illustrate the present invention. They are for illustrative purposes only; the scope of the invention is not to be considered limited in any way thereby.

Where mass spectral (MS) data are presented in the examples below, analysis was performed using an Agilent Technologies 6120 quadrupole LC/MS. Resolution of enantiomers was typically performed using supercritical fluid chromatography utilizing a Chiral Technologies AD or AD-H

EXAMPLES

Preparative Example 1

6-Bromo-4-methyl-N-[4-(trifluoromethyl)pyridin-2-yl]pyridin-2-amine (PrepEx-1)

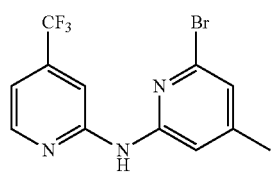

PrepEx-1

N₂ was bubbled through a solution of 4-(trifluoromethyl)pyridin-2-amine (12.0 g, 74.0 mmol) and 2,6-dibromo-4-methylpyridine (18.57 g, 74.0 mmol) in 1,4-dioxane (240 mL) for five minutes. Sodium tert-butoxide (7.83 g, 81 mmol) and 1,1'-bis(di-tert-butylphosphino)ferrocene palladium dichloride (1.204 g, 1.851 mmol) were added and the solution was heated to 75° C.; the mixture was stirred using a magnetic stirrer. Upon completion, the reaction mixture was cooled and then partitioned between EtOAc (200 mL) and 5% aqueous ammonium chloride solution (200 mL). The layers were separated and the aqueous layer was extracted with EtOAc (200 mL). The combined organic layers were washed with water, dried over sodium sulfate, filtered, and concentrated under reduced pressure. The resulting residue was purified by chromatography on silica gel (gradient of 0-40% EtOAc/hexane) to provide 6-bromo-4-methyl-N-[4-(trifluoromethyl)pyridin-2-yl]pyridin-2-amine (22.5 g, 67.7 mmol, 92%). MS ESI calcd for $C_{12}H_9BrF_3N_3$ [M+H]⁺ 332, found 332. ¹H NMR (600 MHz, CDCl₃) δ 8.39 (s, 1H), 7.73 (s, 1H), 7.54 (s, 1H), 7.33 (s, 1H), 7.05 (s, 1H), 6.92 (d, J=2.7 Hz, 1H), 2.31 (d, J=3.6 Hz, 3H) ppm.

Preparative Example 2

4-Methyl-6-(1,3-thiazol-5-yl)-N-[4-(trifluoromethyl)pyridin-2-yl]pyridin-2-amine (PrepEx-2)

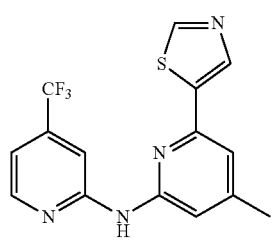

PrepEx-2

In a dry flask, allylpalladium(II) chloride dimer (1.333 g, 3.64 mmol) and butyldiadamantylphosphine (5.23 g, 14.57 mmol) were taken-up in degassed dimethylacetamide (50 mL). The vessel was evacuated and backfilled with argon (3 times), and then stirred at rt for 10 minutes. Additional degassed dimethylacetamide (50 mL), 6-bromo-4-methyl-N-[4-(trifluoromethyl)pyridin-2-yl]pyridin-2-amine (12.1 g, 36.4 mmol), thiazole (10.36 mL, 146 mmol), potassium carbonate (15.11 g, 109 mmol), and pivalic acid (6.34 mL, 54.6 mmol) were added. The vessel was evacuated and backfilled with argon (3 times) and stirred under argon at 130° C. overnight. The reaction mixture was then diluted with EtOAc (500 mL), cooled to rt, filtered through Celite®, and concentrated. Water was added to the crude product mixture and the resulting precipitate was collected via filtration and subjected to silica gel flash chromatography (ethyl acetate-hexanes). Purification yielded 4-methyl-6-(1,3-thiazol-5-yl)-N-[4-(trifluoromethyl)pyridin-2-yl]pyridin-2-amine (5.29 g, 15.72 mmol, 43% yield) as a yellow solid. MS ESI calcd for $C_{15}H_{11}F_3N_4S$ [M+H]⁺ 337, found 337. ¹H NMR (600 MHz, DMSO) δ 10.21 (s, 1H), 9.14 (s, 1H), 8.59 (s, 1H), 8.52 (s, 1H), 8.47 (d, J=5.1 Hz, 1H), 7.43 (s, 1H), 7.20 (d, J=5.1 Hz, 1H), 7.11 (s, 1H), 2.30 (s, 3H) ppm.

Preparative Example 3

Tert-butyl (6-bromo-4-methylpyridin-2-yl)carbamate (PrepEx-3)

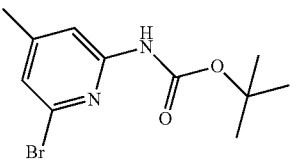

PrepEx-3

Into a flask were added tert-butyl carbamate (5.6 g, 47.8 mmol) and 2,6-dibromo-4-methyl-pyridine (12 g, 47.8 mmol) followed by degassed 2-MeTHF (120 mL). Solid sodium tert-butoxide (4.6 g, 47.8 mmol) was then added followed by tris(dibenzylideneacetone)dipalladium(0) (1.1 g, 1.2 mmol) and 1,1'-bis(di-tert-butylphosphino)ferrocene (1.1 g, 2.4 mmol), and the solution evacuated and refilled with nitrogen 3 times. The solution was heated to 70° C. for 4 h and then cooled to rt. The mixture was treated with water (20 mL) and EtOAc (100 mL) and filtered through Celite®. The organic solution was washed with brine (100 mL) and then concentrated under reduced pressure. The resulting residue was purified via silica gel chromatography to afford tert-butyl (6-bromo-4-methylpyridin-2-yl)carbamate (11.2 g, 82%) as a white solid. MS ESI calcd for $C_{11}H_{15}BrN_2O_2$ [M+H]⁺ 287, found 287. ¹H NMR (600 MHz, CDCl₃) δ 7.70 (s, 1H), 7.13 (s, 1H), 6.95 (s, 1H), 2.29 (s, 3H), 1.49 (s, 9H) ppm.

Preparative Example 4

(R or S)-Methyl 5-hydroxy-5-(thiazol-2-yl)-5,6,7,8-tetrahydronaphthalene-2-carboxylate (PrepEx-4A and PrepEx-4B)

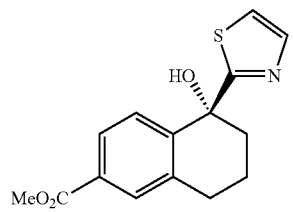

-continued

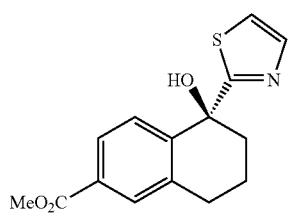

Step 1:

To a solution of 5-oxo-5,6,7,8-tetrahydronaphthalene-2-carboxylic acid (22.0 g, 116 mmol) in methanol (132 mL) was added sulfuric acid (22.7 g, 231 mmol) and the solution was heated to 60° C. for 4 h. Crystallization started when the solution was cooled, and then water (130 mL) was added. The slurry was filtered and the solid dried under vacuum to afford methyl 5-oxo-5,6,7,8-tetrahydronapthalene (20.6 g, 101 mmol, 87%) as an off-white solid. MS ESI calcd for $C_{12}H_{12}O_3$ [M+H]$^+$ 205, found 205.

Step 2:

Thiazole (14.6 g, 172 mmol) was slowly added to a solution of isopropylmagnesium chloride lithium chloride complex (142 mL, 1.3 M in THF, 185 mmol) maintaining a temperature between 0 and 5° C. The resulting slurry was stirred for 1 h and then cooled to −20° C. A solution of methyl 5-oxo-5,6,7,8-tetrahydronapthalene (27.0 g, 132 mmol) in THF (50 mL) was added, maintaining the temperature between 0 to 5° C. and the solution stirred for 2 h. The resulting slurry was quenched with methanol (7.5 mL) and then water (50 mL) and isopropyl acetate (200 mL) were added, followed by 2M aqueous HCl (50 mL). The resulting aqueous layer was extracted with isopropyl acetate (100 mL) and the organic layer was washed with saturated aqueous sodium bicarbonate (100 mL) and brine (100 mL). The resulting material was purified on silica gel to afford methyl 5-hydroxy-5-(1,3-thiazol-2-yl)-5,6,7,8-tetrahydronaphathlene-2-carboxylate (38.3 g, 78 mmol). Chiral chromatography on an AD column with 40% ethanol in $CO_2$ afforded each enantiomer of methyl hydroxy-5-(1,3-thiazol-2-yl)-5,6,7,8-tetrahydronaphathlene-2-carboxylate (18.0 g, 35 mmol, 27% of each isomer). The second-eluting enantiomer (referred to as "enantiomer 2" in Preparative Example 5) was used for subsequent reactions. MS ESI calcd for $C_{15}H_{15}NO_3S$ [M+H]$^+$ 290, found 290. $^1$H NMR (600 MHz, CDCl$_3$) δ 7.82 (s, 1H), 7.75 (dd, 1H, J=8.2, 1.7 Hz), 7.69 (d, 1H, J=3.2 Hz), 7.27 (d, 1H, J=3.2 Hz), 7.24 (s, 1H), 3.87 (s, 3H), 3.74 (s, 1H), 2.93 (dd, 1H, J=6.5, 6.5 Hz), 2.39 (ddd, 1H, J=13.3, 9.9, 3.2 Hz), 2.23 (ddd, 1H, J=13.4, 7.9, 3.1 Hz), 2.06-1.99 (m, 1H), 1.98-1.92 (m, 1H) ppm.

Enantiomer 2 was subsequently determined to have the R configuration.

Preparative Example 5

(R) Methyl 5-[5-(6-amino-4-methylpyridin-2-yl)-1,3-thiazol-2-yl]-5-hydroxy-5,6,7,8-tetrahydronaphthalene-2-carboxylate (PrepEx-5)

PrepEx-5

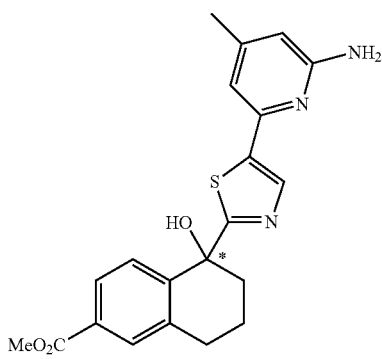

Into a flask were added butyl diadamantyl phosphine (6.1 g, 0.4 mmol) and allyl palladium chloride dimer (1.56 g, 4.2 mmol) followed by nitrogen purged dimethyl acetamide (98 mL). After 10 minutes of stirring, potassium carbonate (17.6 g, 127 mmol), pivalic acid (6.5 g, 63.7 mmol), (R)-methyl hydroxy-5-(1,3-thiazol-2-yl)-5,6,7,8-tetrahydronaphathlene-2-carboxylate (enantiomer 2 from Preparative Example 4, 11.0 g, 38.2 mmol) and tert-butyl 6-bromo-4-methylpyridine-2-ylcarbamate (12.2 g, 42.5 mmol) were added. The slurry was evacuated and refilled with nitrogen three times and then slowly heated to 100° C. and stirred at that temperature for 12 hours. The slurry was cooled to 35° C. and diluted with ethyl acetate (100 mL). The slurry was then filtered through Celite® and washed with 10% aqueous NaCl (3×100 mL). The resulting solution was concentrated under reduced pressure and purified on silica gel. The two products obtained from this (R)-(methyl 5-(5-(6-(tert-butoxycarbonylamino)-4-methylpyridin-2-yl)thiazol-2-yl)-5-hydroxy-5,6,7,8-tetrahydronaphthalene-2-carboxylate and (R)-methyl 5-hydroxy-5-(5-(4-methyl-6-pivalamidopyridin-2-yl)thiazol-2-yl)-5,6,7,8-tetrahydronaphthalene-2-carboxylate) were treated with HCl (20 mL of 6N solution) and heated at 80° C. for 12 h. The solution was cooled to RT and treated with EtOAc (100 mL) and NaHCO$_3$ (50 mL). The aqueous layer was extracted with EtOAc (50 mL) and then after evaporation the residue was purified by chromatography on silica gel to afford (R)-methyl 5-[6-amino-4-methylpyridin-2-yl)-1,3-thiazol-2-yl]-5-hydroxy-5,6,7,8-tetrahydronapthalene-2-carboxylate (2.6 g, 6.57 mmol). MS ESI calcd for $C_{15}H_{11}F_3N_4S$ [M+H]$^+$ 396, found 396. $^1$H NMR (600 MHz, CDCl$_3$) δ 8.03 (s, 1H), 7.83 (s, 1H), 7.77 (d, 1H, J=8.2 Hz), 7.34 (d, 1H, J=8.2 Hz), 6.82 (s, 1H), 6.21 (s, 1H), 4.34 (s, 2H), 3.88 (s, 3H), 3.70 (s, 1H), 2.94 (dd, 2H, J=6.2, 6.2 Hz), 2.41

(ddd, 1H, J=13.1, 9.6, 3.2 Hz), 2.27 (ddd, 1H, J=13.5, 8.2, 3.1 Hz), 2.22 (s, 3H), 2.08-2.01 (m, 1H), 2.00-1.95 (m, 1H) ppm.

Preparative Example 6

6-bromo-N-(4-methoxypyridin-2-yl)-4-methylpyridin-2-amine (PrepEx-6)

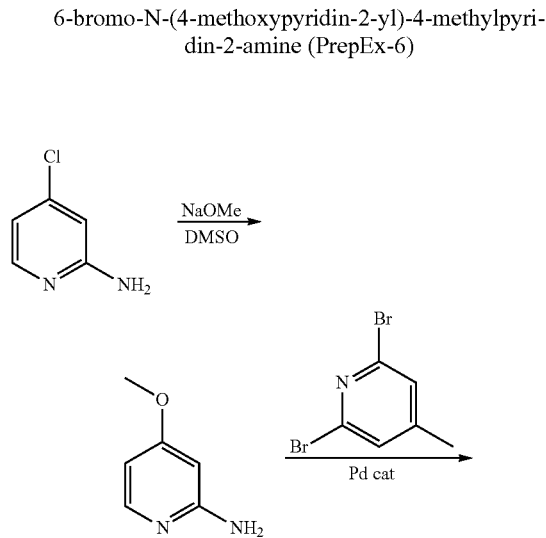

Step 1:

To a solution of 4-chloropyridin-2-amine (3 g, 23.2 mmol) in DMSO (60 mL) was added sodium methoxide (12.6 g, 232 mmol) and the mixture was then stirred at 150° C. for 3 hours then poured into ice-water. The product was extracted with EtOAc (2×100 mL), and the combined organic layers were washed with water (50 mL) and brine (50 mL), dried (Na$_2$SO$_4$) and concentrated. The residue was purified by silica gel chromatography using a solvent system of 50% petroleum ether/EtOAc to give 4-methoxypyridin-2-amine (460 mg, 16%) as a yellow solid MS ESI calcd for C$_6$H$_8$N$_2$O [M+H]$^+$ 125, found 125.

Step 2:

To a solution of 4-methoxypyridin-2-amine (620 mg, 5 mmol) and 2,6-dibromo-4-methylpyridine (1123 mg, 5.25 mmol) in dioxane (18 mL) was added 1,1'-bis(di-tertbutylphosphino)ferrocene palladium dichloride (280 mg, 0.5 mmol) and sodium tert-butoxide (437 mg, 5.25 mmol). Then the mixture stirred under microwave irradiation for 1.5 hours at 80° C. Then the mixture was poured into water (50 mL), and extracted with EtOAc (100 mL). The organic layer was washed with water (50 mL) and brine (50 mL), dried and concentrated. The residue purified by silica gel chromatography using a solvent system of 75% petroleum ether/EtOAc. The product containing fractions were collected and concentrated to give 6-bromo-N-(4-methoxypyridin-2-yl)-4-methylpyridin-2-amine (627 mg, 50%). MS ESI calcd for C$_{12}$H$_{12}$BrN$_3$O [M+H]$^+$ 294, found 294.

The following compound was synthesized in an analogous manner:

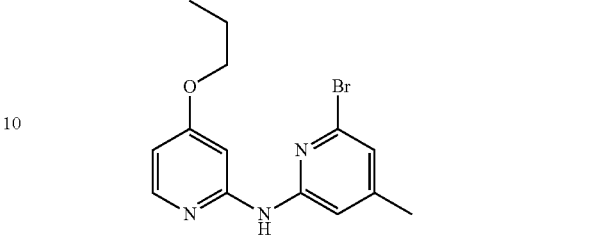

6-bromo-4-methyl-N-(4-propoxypyridin-2-yl)pyridin-2-amine. MS ESI calcd for C$_{14}$H$_{16}$BrN$_3$O [M+H]$^+$ 322, found 322.

Preparative Example 7

N-(2-bromo-6-((4-(trifluoromethyl)pyridin-2-yl)amino)pyridin-4-yl)acetamide (PrepEx-7)

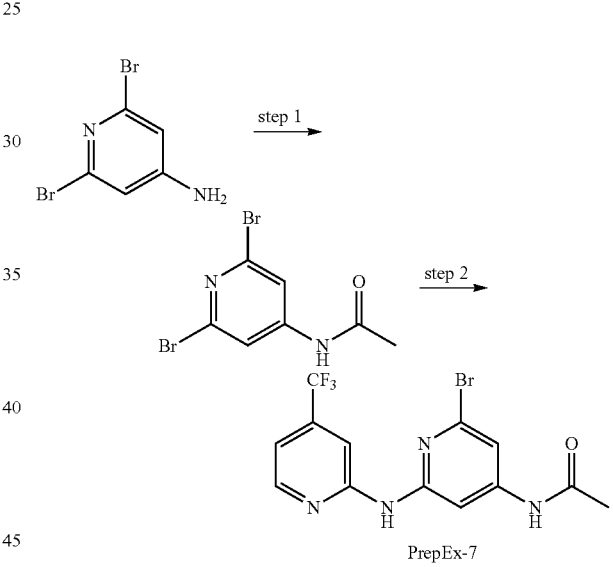

Step 1:

To a solution of 2,6-dibromopyridin-4-amine (1.0 g, 3.97 mmol), DMAP (0.048 g, 0.397 mmol), and pyridine (0.482 mL, 5.95 mmol) in THF (7.94 mL) at rt was slowly added acetic anhydride (0.412 mL, 4.37 mmol), and the mixture was stirred at rt for 16 h, after which time the reaction was heated to 65° C. for a period of 5 days. After cooling to rt, MeOH (5 mL) was added and the reaction was concentrated under reduced pressure. The product was purified by silica gel chromatography using a gradient solvent system of 0-100% EtOAc/Hexanes. The product-containing fractions were collected and concentrated under reduced pressure to give N-(2,6-dibromopyridin-4-yl)acetamide (1.10 g, 94%) as a yellow solid. MS ESI calcd for C$_7$H$_6$Br$_2$N$_2$O [M+H]$^+$ 293, found 293.

Step 2:

A microwave tube was charged with a stir bar, N-(2,6-dibromopyridin-4-yl)acetamide (0.95 g, 3.23 mmol), 2-Amino-4-(trifluoromethyl)pyridine (0.576 g, 3.56 mmol), Pd(OAc)$_2$ (0.073 g, 0.323 mmol), Xantphos (0.281 g, 0.485 mmol), and Cs$_2$CO$_3$ (2.106 g, 6.46 mmol). The mixture was vacuum-purged with argon 3 times, then degassed dioxane (6.46 mL) was added. The reaction was sealed and heated to 100° C. for 3 hours, after which time the reaction was cooled to rt, diluted with MeOH (10 mL) and concentrated under reduced pressure. The product was purified by silica gel chromatography using a gradient solvent system of 0-100% EtOAc/Hexanes. The product containing fractions were collected and concentrated to give N-(2-bromo-6-((4-(trifluoromethyl)pyridin-2-yl)amino)pyridin-4-yl)acetamide (605 mg, 50%) as a white solid. MS ESI calcd for C$_{13}$H$_{10}$BrF$_3$N$_4$O [M+H]$^+$ 375, found 375.

Preparative Example 8

6-Bromo-N-(4-(1-(4-methoxybenzyl)-1H-1,2,3-triazol-4-yl)pyridin-2-yl)-4-methylpyridin-2-amine (PrepEx-8)

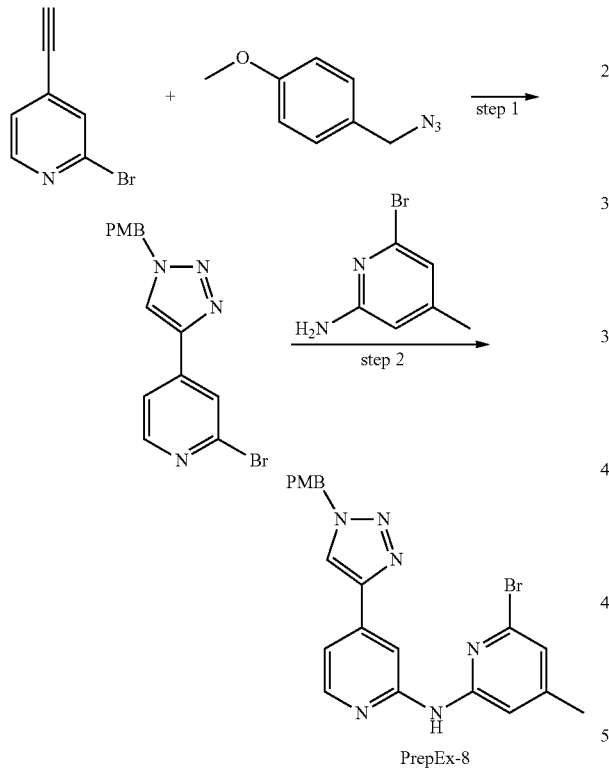

PrepEx-8

Step 1:

To a flask containing 2-bromo-4-ethynylpyridine (1 g, 5.49 mmol) was added 4-methoxybenzyl azide (896 mg, 5.49 mmol), CuSO$_4$(H$_2$O)$_5$ (137 mg, 0.549 mmol), sodium ascorbate (544 mg, 2.75 mmol), water (13.7 mL) and tBuOH (13.7 mL) and the reaction was stirred for 16 h at rt. The reaction was diluted with EtOAc (50 mL) and washed with saturated aqueous NaHCO$_3$ (1×20 mL) and brine (1×20 mL). The organic phase was dried (MgSO$_4$), filtered, and purified by silica gel chromatography using a gradient solvent system of 30-70% EtOAc/Hexanes. Concentration of the product fractions yielded 2-bromo-4-(1-(4-methoxybenzyl)-1H-1,2,3-triazol-4-yl)pyridine (1.46 g, 77%) as a white powder. MS ESI calcd for C$_{15}$H$_{13}$BrN$_4$O [M+H]$^+$ 345, found 345.

Step 2:

To a flask was added 2-bromo-4-(1-(4-methoxybenzyl)-1H-1,2,3-triazol-4-yl)pyridine (329 mg, 0.953 mmol), 2-bromo-4-methyl-6-aminopyridine (178 mg, 0.953 mmol), Pd(OAc)$_2$ (21.4 mg, 0.095 mmol), Xantphos (83 mg, 0.143 mmol), and Cs$_2$CO$_3$ (621 mg, 1.91 mmol), and the mixture was vacuum-purged with argon 3 times. Degassed 1,4-Dioxane (3.8 mL) was added and the reaction was heated to 100° C. for 30 min. after which time the reaction was cooled and diluted with EtOAc (20 mL). The reaction was filtered then dry loaded onto silica and purified by silica gel chromatography using a gradient solvent system of 30-60% EtOAc/Hexanes. Concentration of the product-containing fractions yielded 6-bromo-N-(4-(1-(4-methoxybenzyl)-1H-1,2,3-triazol-4-yl)pyridin-2-yl)-4-methylpyridin-2-amine (255 mg, 59%) as a tan solid. MS ESI calcd for C$_{21}$H$_{19}$BrN$_6$O [M+H]$^+$ 451, found 451.

Preparative Example 9

(R and S)-Methyl 5-hydroxy-5-(thiazol-2-yl)-5,6,7,8-tetrahydronaphthalene-1-carboxylate (PrepEx-9A and 9B)

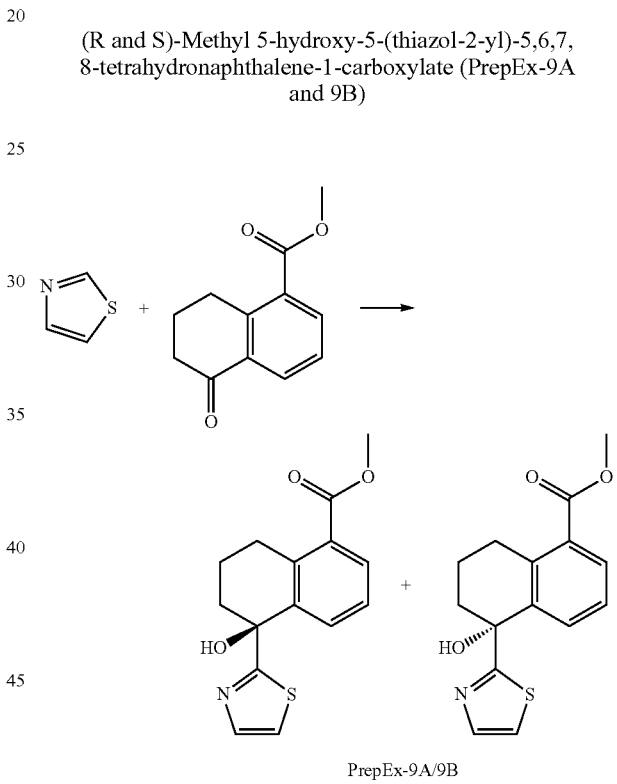

PrepEx-9A/9B

To an oven-dried, N$_2$-purged flask was added isopropyl magnesium chloride lithium chloride complex (7.91 mL, 10.3 mmol) and THF (18.4 mL) and the solution was cooled to 0° C. A solution of thiazole (0.813 g, 9.55 mmol) in THF (9.18 mL) was then added, and the reaction was stirred for 45 min at 0° C., and then cooled to −10° C. A solution of methyl 5-oxo-5,6,7,8-tetrahydronaphthalene-1-carboxylate (1.5 g, 7.34 mmol) in THF (9.18 mL) was then added, after which the reaction was allowed to warm to rt over a period of 4 h. MeOH (5 mL) was then added and the reaction was partitioned between water (50 mL) and EtOAc (50 mL). The aqueous phase was extracted with EtOAc (2×50 mL), then the combined organic phases were dried (MgSO$_4$), filtered and concentrated. The product was purified by silica gel chromatography using a gradient solvent system of 0-70% EtOAc/DCM. The product-containing fractions were collected and concentrated to give racemic methyl 5-hydroxy-5-(thiazol-2- yl)-5,6,7,8-tetrahydronaphthalene-1-carboxylate as a yellow oil. The enantiomers were resolved by chiral SFC using a Chiral Technology AY-H 2.1×25 cm, 5 uM column, eluting with 20%-50% MeOH+0.25% dimethyl ethylamine/CO$_2$. At a flow rate of 70 mL/min, the two enantiomers eluted at 2.38 min and 2.79 min.

PrepEx-9A:

Faster eluting enantiomer: 591 mg (28%). MS ESI calcd for C$_{15}$H$_{15}$NO$_3$S [M+H]$^+$ 290, found 290.

PrepEx-9B:

Slower eluting enantiomer: 592 mg (28%). MS ESI calcd for C$_{15}$H$_{15}$NO$_3$S [M+H]$^+$ 290, found 290.

Preparative Example 10

Methyl 3-oxo-2,3-dihydro-1H-indene-5-carboxylate (PrepEx-10)

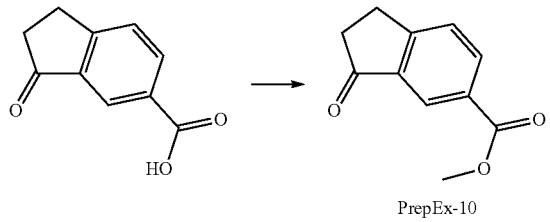

PrepEx-10

To a solution of 3-oxo-2,3-dihydro-1H-indene-5-carboxylic acid (3 g, 17 mmol) in DCM (50 mL) and MeOH (10 mL) was added TMSCHN$_2$ (17 mL, 34 mmol) dropwise and the mixture was stirred at rt for 1 h. The mixture was concentrated under reduced pressure and the residue was purified by silica gel chromatography using a gradient solvent system of 10:1 to 3:1 petroleum ether/EtOAc to give methyl 3-oxo-2,3-dihydro-1H-indene-5-carboxylate (2.0 g, 61%). MS ESI calcd for C$_{11}$H$_{10}$O$_3$ [M+H]$^+$ 191, found 191.

Preparative Example 11

Methyl 1-oxo-2,3-dihydro-1H-indene-4-carboxylate (PrepEx-11)

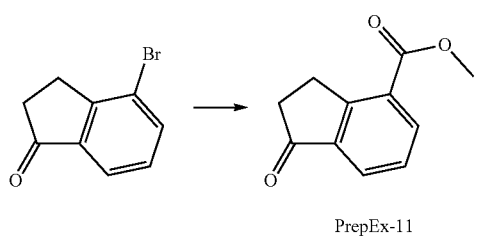

PrepEx-11

To a solution of 4-bromo-2,3-dihydro-1H-inden-1-one (5 g, 24 mmol) in MeOH (120 mL) and Et$_3$N (40 mL) was added Pd(PPh$_3$)$_2$Cl$_2$ (200 mg) and the mixture was stirred under 2.5 MPa of CO for 48 hours. The reaction solution was concentrated under reduced pressure and the residue was purified by silica gel chromatography using 2:1 petroleum ether:EtOAc to afford methyl 1-oxo-2,3-dihydro-1H-indene-4-carboxylate (2.9 g, 64%). MS ESI calcd for C$_{11}$H$_{10}$O$_3$ [M+H]$^+$ 191, found 191.

Preparative Example 12

Methyl 5-oxo-6,7,8,9-tetrahydro-5H-benzo[7]annulene-1-carboxylate (PrepEx-12A) and Methyl 9-oxo-6,7,8,9-tetrahydro-5H-benzo[7]annulene-2-carboxylate (PrepEx-12B)

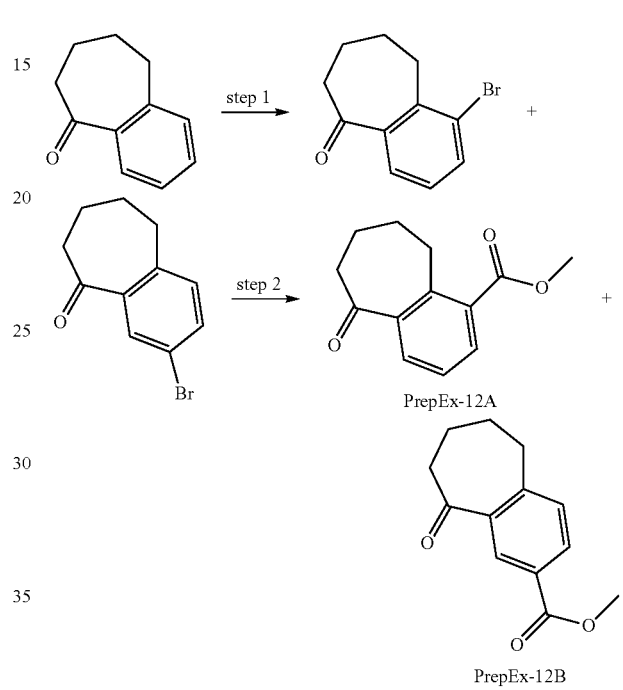

PrepEx-12A

PrepEx-12B

Step 1:

6,7,8,9-tetrahydro-5H-benzo[7]annulen-5-one (8 g, 50 mmol) was added to a flask containing AlCl$_3$ (16.6 g, 125 mmol) dropwise under N$_2$ and the mixture was stirred at r.t. for 30 minutes, and then Br$_2$ (3 mL, 60 mmol) was added dropwise and the mixture was heated to 80° C. for another 5 minutes. Then the mixture was poured into a mixture of conc. HCl (20 mL) and ice (200 g) and stirred for 10 minutes. Then the mixture was extracted with MTBE and the organic layer was washed with aq. NaHCO$_3$ and brine, dried, filtered and concentrated. The residue was purified by silica gel chromatography to give 1-bromo-6,7,8,9-tetrahydro-5H-benzo[7] annulen-5-one (6 g, crude) and 3-bromo-6,7,8,9-tetrahydro-5H-benzo[7]annulen-5-one (4 g, crude), which were used for next step directly.

Step 2a:

To a solution of 1-bromo-6,7,8,9-tetrahydro-5H-benzo[7] annulen-5-one (4 g, crude) in MeOH (30 mL) and Et$_3$N (10 mL) was added Pd(PPh$_3$)$_2$Cl$_2$ (400 mg) and the mixture was stirred under 2 MPa of CO for 48 hours. The mixture was then concentrated and the residue was purified by silica gel chromatography to give methyl 5-oxo-6,7,8,9-tetrahydro-5H-benzo[7]annulene-1-carboxylate (260 mg, 2.4%). MS ESI calcd [M+H]$^+$ 219, found 219.

Step 2b:

To a solution of 3-bromo-6,7,8,9-tetrahydro-5H-benzo[7] annulen-5-one (6 g, crude) in MeOH (30 mL) and Et$_3$N (10 mL) was added Pd(PPh$_3$)$_2$Cl$_2$ (600 mg) and the mixture was stirred under 2 MPa of CO for 48 hours. The mixture was concentrated and the residue was purified by silica gel chromatography to give methyl 9-oxo-6,7,8,9-tetrahydro-5H-benzo[7]annulene-2-carboxylate (1.4 g, 13%). MS ESI calcd [M+H]$^+$ 219, found 219.

Preparative Example 13

5-Oxo-6,7,8,9-tetrahydro-5H-benzocycloheptene-2-carboxylic acid methyl ester (PrepEx-13)

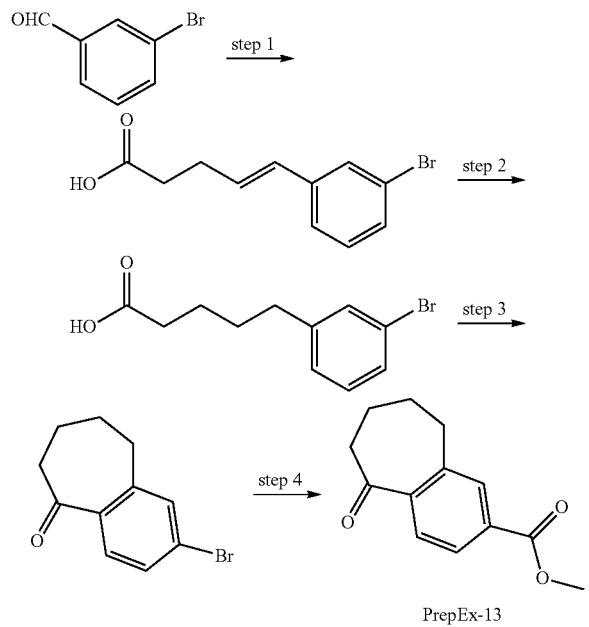

PrepEx-13

Step 1:

To a solution of (3-carboxypropy)triphenylphosphonium bromide (25 g, 58.3 mmol) in DMSO (53 mL) was added t-BuOK (12.4 g, 110.7 mmol). The mixture was stirred at rt for 20 min. Then a solution of 3-Bromo-benzaldehyde (9.3 g, 50.3 mmol) in DMSO (15 mL) was added dropwise. The reaction mixture was stirred at rt for 4 h. The mixture was poured in water and extracted with DCM. The organic layer was dried over anhydrous sodium sulfate, filtered, and then concentrated under reduced pressure. The crude material was purified by silica gel chromatography using a solvent system of 5:1 petroleum ether/EtOAc to give 5-(3-Bromo-phenyl)-pent-4-enoic acid (4.8 g, 38%). $^1$H-NMR (400 MHz, CDCl3) δ ppm 7.45 (s, 1H), 7.2-7.25 (m, 1H), 7.1-7.15 (m, 2H), 6.4-6.45 (m, 1H), 6.23-6.3 (m, 1H), 2.4-2.6 (m, 4H).

Step 2:

To a solution of 5-(3-Bromo-phenyl)-pent-4-enoic acid (4 g, 16 mmol) in EtOAc (150 mL) was added Pd/C (400 mg) and a solution of 40% HBr in AcOH (0.5 mL). The mixture was stirred at rt under 1 atm of hydrogen for 1 h. The reaction mixture was filtered and concentrated under reduced pressure. The crude material was purified by silica gel chromatography using a solvent system of 5:1 petroleum ether/EtOAc to give 5-(3-Bromo-phenyl)-pentanoic acid (3.2 g, 80%). $^1$H-NMR (400 MHz, CDCl3) δ ppm 7.3-7.4 (m, 2H), 7.05-7.15 (m, 2H), 2.55 (s, 2H), 2.35 (s, 2H), 1.7 (m, 4H).

Step 3:

To a solution of 5-(3-Bromo-phenyl)-pentanoic acid (6 g, 23 mmol) in chlorobenzene (300 mL) was added PPA (18 g) and the mixture was heated to reflux for 8 h. The mixture was cooled to rt and filtered. The filtrate was concentrated under reduced pressure then purified by silica gel chromatography using a solvent system of 10:1 petroleum ether/EtOAc to give 2-bromo-6,7,8,9-tetrahydro-benzocyclohepten-5-one (2.4 g, 42.9%). MS ESI calcd for C$_{11}$H$_{11}$BrO [M+H]$^+$ 239, found 239.

Step 4:

To a solution of 2-Bromo-6,7,8,9-tetrahydro-benzocyclohepten-5-one (2.5 g, 10.5 mmol) in MeOH (30 mL) and Et$_3$N (10 mL) was added Pd(PPh$_3$)$_2$Cl$_2$ (250 mg) and the mixture was stirred under 2 MPa of CO for 48 hours. The mixture was then concentrated and the residue was purified by silica gel chromatography using a solvent system of 10:1 petroleum ether/EtOAc to give 5-oxo-6,7,8,9-tetrahydro-5H-benzocycloheptene-2-carboxylic acid methyl ester (1.7 g, 74%). MS ESI calcd for C$_{13}$H$_{14}$O$_3$ [M+H]$^+$ 219, found 219. $^1$H-NMR (400 MHz, CDCl3) δ ppm 7.9-7.94 (m, 1H), 7.85 (d, J=8, 1H), 7.7 (s, 1H), 3.96 (s, 3H), 3.0 (m, 2H), 2.8 (m, 2H), 1.91-1.96 (m, 2H), 1.85-1.9 (m, 2H).

Preparative Example 14

1-Bromo-5-oxo-5,6,7,8-tetrahydronaphthalene-2-carboxylate (PrepEx-14)

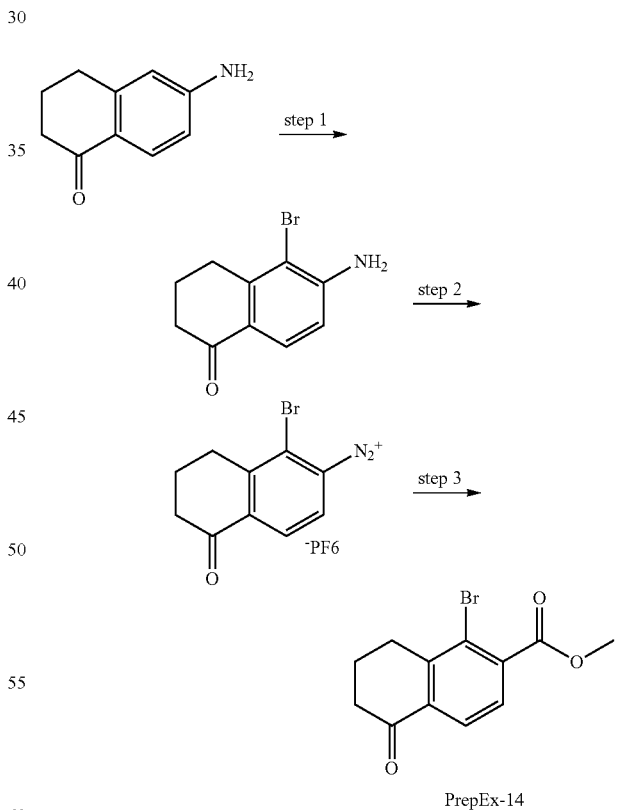

PrepEx-14

Step 1:

To a flask was added 6-amino-3,4-dihydro-1(2H)-naphthalenone (5.30 g, 32.9 mmol) and DCM (329 mL) and the mixture was cooled to 0° C. N-bromosuccinimide (5.85 g, 32.9 mmol) was added portionwise over 1 hour. The mixture then was stirred at 0° C. for 3 hours. The reaction was quenched with aqueous sodium bicarbonate (100 mL) and then extracted with DCM (3×100 mL). The combined organic fractions were dried (Na₂SO₄), filtered and concentrated under reduced pressure. The product was purified by silica gel chromatography using a gradient solvent system of 0-65% EtOAc/Hexanes. Concentration of the product-containing fractions yielded 6-amino-5-bromo-3,4-dihydronaphthalen-1(2H)-one (7.8 g, 87%) as a light tan solid. MS ESI calcd for $C_{10}H_{10}BrNO$ 240 [M+H]⁺. found 240.

Step 2:

To a solution of 6-amino-5-bromo-3,4-dihydronaphthalen-1(2H)-one (7.8 g, 28.6 mmol) in water (20 mL) and tetrafluoroboric acid (78 mL, 429 mmol) at 0° C. was slowly added a solution of sodium nitrite (4.93 g, 71.5 mmol) in water (5 mL). The mixture was then allowed to warm to rt over 30 minutes. The mixture was filtered, then hexafluorophosphoric acid (32.1 mL, 143 mmol) was added, and the resulting precipitate was collected via filtration to give 1-bromo-5-oxo-5,6,7,8-tetrahydronaphthalene-2-diazonium hexafluorophosphate(V) (3.22 g, 28%) as a tan solid. MS ESI calcd for $C_{10}H_8BrN_2O+$ 251 [M]⁺. found 251.

Step 3:

A mixture of 1-bromo-5-oxo-5,6,7,8-tetrahydronaphthalene-2-diazonium hexafluorophosphate(V) (3.0 g, 6.80 mmol) and palladium acetate (0.076 g, 0.340 mmol) in MeOH (30 mL, 742 mmol) at rt was bubbled with carbon monoxide for 1 hour, after which time the reaction was diluted with DCM (50 mL), filtered, and concentrated under reduced pressure. The material was purified by silica gel chromatography using a gradient solvent system of 0-65% EtOAc/Hexanes. The product containing fractions were collected and concentrated under reduced pressure to give methyl 1-bromo-5-oxo-5,6,7,8-tetrahydronaphthalene-2-carboxylate (243 mg, 13%) as an orange solid. MS ESI calcd for $C_{12}H_{11}BrO_3$ [M+H]⁺ 283, found 283.

Preparative Example 15

Alternative Preparation of (Rac)-Methyl 5-hydroxy-5-(thiazol-2-yl)-5,6,7,8-tetrahydronapthalene-2-carboxylate (Racemic Mixture of Prep-Ex. 4A and 4B)

Flow Reactor

A solution of n-butyllithium (2.3 M in hexanes) is pumped (push-pull syringe-pump) to a ⅛" tee with a pressure gauge and 2 feet of ⅛" stainless steel tubing (for pre-cooling). This tubing is connected to a ¼ inch T-mixer. Thiazole (0.5 M in THF) is pumped using a pump, 100 μL head (Fluid Metering, Inc., Syosset, N.Y. USA) to 2 feet of ⅛" stainless steel tubing (for pre-cooling) connected to the same T-mixer. The T-mixer is connected to a static mixer ¼-34 (5.3 mL) (Koflo Corporation, Cary, Ill. USA) connected to a ¼" elbow and ¼" stainless steel tubing of 6 inches in length (3.3 mL). This 6-inch length tubing is connected to another ¼" T-mixer which is also connected to a feed of methyl 5-oxo-5,6,7,8-tetrahydronaphthalene-2-carboxylate and BF₃ (0.5 M in THF, pumped with a FMI pump, 100 μL head), and to a second static mixer Koflo ¼-34 (5.3 mL) followed by a "loop" of ¼" stainless steel (2.5 ft length, 16.8 mL). The reactor has a total volume of 30.7 mL, and is placed into a cold bath at −45° C. (±5° C., dry ice/acetone). The outlet stream is then connected to a ⅛" T-mixer (outside of the cold bath) fed with methanol (FMI pump, 100 μL head) for in situ quenching, and is finally collected into an extractor containing MTBE and aqueous phosphoric acid (1.5 M). A flow diagram of the assembly is shown in FIG. 1.

Process Description and Specifications

The process used was a stepwise process wherein the thiazole anion was preformed, and then quenched with ketoester/BF₃. The reaction product was then quenched in situ with methanol.

−45° C. (±5° C.), −τ₁=0.13 min (8 s), τ₂=0.17 min (10 s) (τ$_{total}$=0.3 min (18 s).

methyl 5-oxo-5,6,7,8-tetrahydronaphthalene-2-carboxylate—0.5 M/THF, 38.50 mL/min contains 1.1 equiv BF₃-Et₂O thiazole—0.5 M/THF, 57.75 mL/min (1.5 equiv)

BuLi—2.3M/Hex, 8.75 mL/min (1.05 equiv)

methanol=7.80 mL/min (10 equiv)

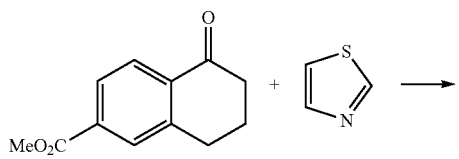

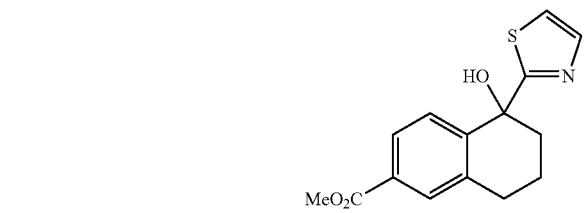

The reactor was placed into a cold bath at −45° C. (±5° C., dry ice/acetone), and all 4 pumps were started (at the flow rate indicated above). Steady state was reached within 1 minute. The temperature of the cold bath was maintained at −45° C.±5° C. throughout the run by adding a handful of dry ice as needed. The outlet stream was collected into a stirred biphasic mixture of MTBE (4 L) and aqueous phosphoric acid (1.5 M, 2.5 L). Pumping lasted 2.1 hour (4.9 L of methyl 5-oxo-5,6,7,8-tetrahydronaphthalene-2-carboxylate solution, 0.5 Kg, 2.45 moles). At the end of the run, the reactor was flushed with THF, and hexane (at the n-BuLi feed) for a few minutes.

The layers of the biphasic mixture were separated, and the organic layer was washed with water (2×4 L). The combined aqueous layers were extracted with MTBE (2 L), then the combined organic layers were concentrated under reduced pressure. The solvent was switched to 2-propanol, during which time the product crystallized to give a white slurry. The volume was adjusted to about. 3 L/Kg (final volume of 1.8 L of 2-propanol). Water was then added slowly at rt (4.2 L, 70/30 water/2-propanol final ratio, 10 L/Kg) over 1 hour. The slurry was aged for an additional 18 h, and then filtered, washing through with 1 L of 70/30 water/2-propanol. After 1 h of suction on a sintered funnel, the wet cake was dried in a vacuum oven under a stream of nitrogen at +50° C. for 48 hours to give 626 g of product as an off-white solid.

Example 1

(R)-5-(5-{6-[(4-Tert-butoxypyridin-2-yl)amino]-4-methylpyridin-2-yl}-1,3-thiazol-2-yl)-5-hydroxy-5,6,7,8-tetrahydronaphthalene-2-carboxylic acid, ammonia salt (1)

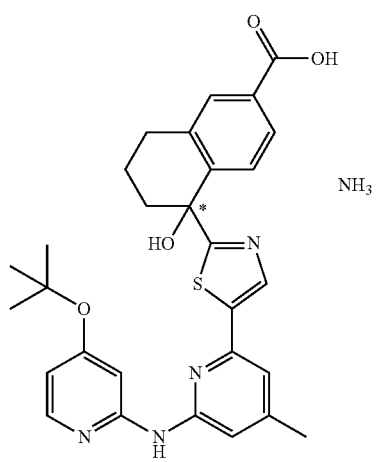

A dry test tube was charged with a stir bar, 2-bromo-4-tert-butoxypyridine (101.2 mg, 0.405 mmol), tris(dibenzylideneacetone)dipalladium(0) (18.52 mg, 0.020 mmol), (9,9-dimethyl-9H-xanthene-4,5-diyl)bis(diphenylphosphine) (29.3 mg, 0.051 mmol), and potassium carbonate (84 mg, 0.607 mmol). The tube was sealed, evacuated and backfilled with argon. (R)-Methyl 5-[5-(6-amino-4-methylpyridin-2-yl)-1,3-thiazol-2-yl]-5-hydroxy-5,6,7,8-tetrahydronaphthalene-2-carboxylate (80 mg, 0.202 mmol) was taken up in fully degassed dioxane (1011 µl) under argon and then added to the reaction mixture, which was sealed and stirred at 100° C. overnight. The tube was cooled to rt, potassium hydroxide (40% in water, 567 µl, 4.05 mmol) was added, and the reaction was allowed to stir as such for 4 hours. The reaction mixture was diluted with DMSO (1 mL), barrier filtered, and purified by reverse-phase HPLC (C18 column, water-acetonitrile, ammonium hydroxide modifier) to furnish (R)-5-(5-{6-[(4-tert-butoxypyridin-2-yl)amino]-4-methylpyridin-2-yl}-1,3-thiazol-2-yl)-5-hydroxy-5,6,7,8-tetrahydronaphthalene-2-carboxylic acid, ammonia salt (47.4 mg, 0.087 mmol, 43% yield) as a white solid. MS ESI calcd for $C_{29}H_{30}N_4O_4S$ $[M+H]^+$ 531, found 531. $^1$H NMR (600 MHz, DMSO) δ 9.46 (s, 1H), 8.15 (s, 1H), 8.04 (d, J=5.6 Hz, 1H), 7.59 (s, 1H), 7.55 (s, 1H), 7.50-7.47 (m, 1H), 7.34 (s, 1H), 7.19 (s, 1H), 7.06-7.01 (m, 1H), 6.50-6.44 (m, 1H), 2.80-2.74 (m, 2H), 2.36-2.30 (m, 1H), 2.25 (s, 3H), 2.07-2.01 (m, 1H), 1.96-1.88 (m, 2H), 1.43 (s, 9H) ppm.

TABLE 1

| Ex. | $R^6$ | $R^7$ | $R^5$ | $R^4$ | * | IUPAC Name | $[M + H]^+$ Calc'd | $[M + H]^+$ Obs'd | Form |
|---|---|---|---|---|---|---|---|---|---|
| 1 | —OC(CH$_3$)$_3$ | H | H | —CO$_2$H | R | 5-(5-{6-[(4-tert-butoxypyridin-2-yl)amino]-4-methylpyridin-2-yl}-1,3-thiazol-2-yl)-5-hydroxy-5,6,7,8-tetrahydronaphthalene-2-carboxylic acid | 531 | 531 | NH$_4^+$ Salt |
| 1A | —C(H)F$_2$ | H | H | —CO$_2$H | R | 5-[5-(6-{[4-(difluoromethyl)pyridin-2-yl]amino}-4-methylpyridin-2-yl)-1,3-thiazol-2-yl]-5-hydroxy-5,6,7,8-tetrahydronaphthalene-2-carboxylic acid | 509.1 | 509 | NH$_4^+$ Salt |

TABLE 1-continued

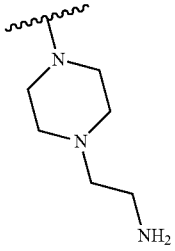 [SMILES: *N1CCN(CCN)CC1]

| Ex. | R⁶ | R⁷ | R⁵ | R⁴ | * | IUPAC Name | [M + H]⁺ Calc'd | [M + H]⁺ Obs'd | Form |
|---|---|---|---|---|---|---|---|---|---|
| 1B | —CF₃ | Cl | H | —CO₂H | R | 5-[5-(6-{[5-chloro-4-(trifluoromethyl)pyridin-2-yl]amino}-4-methylpyridin-2-yl)-1,3-thiazol-2-yl]-5-hydroxy-5,6,7,8-tetrahydronaphthalene-2-carboxylic acid | 561.1 | 561 | NH₄⁺ Salt |
| 1C | 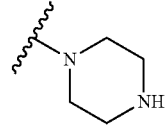 [SMILES: *N1CCNCC1] | H | H | —CO₂H | R | 5-{5-[6-({4-[4-(2-aminoethyl)piperazin-1-yl]pyridin-2-yl}amino)-4-methylpyridin-2-yl]-1,3-thiazol-2-yl}-5-hydroxy-5,6,7,8-tetrahydronaphthalene-2-carboxylic acid | 586.3 | 586 | NH₄⁺ Salt |
| 1D | 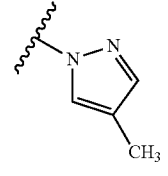 [SMILES: *n1cc(C)cn1] | H | H | —CO₂H | R | 5-hydroxy-5-[5-(4-methyl-6-{[4-(piperazin-1-yl)pyridin-2-yl]amino}pyridin-2-yl)-1,3-thiazol-2-yl]-5,6,7,8-tetrahydronaphthalene-2-carboxylic acid | 543.2 | 543 | NH₄⁺ Salt |
| 1E | 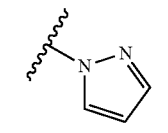 [SMILES: *n1cccn1] | H | H | —CO₂H | R | 5-hydroxy-5-[5-(4-methyl-6-{[4-(4-methyl-1H-pyrazol-1-yl)pyridin-2-yl]amino}pyridin-2-yl)-1,3-thiazol-2-yl]-5,6,7,8-tetrahydronaphthalene-2-carboxylic acid | 539.2 | 539 | NH₄⁺ Salt |
| 1F |  | H | H | —CO₂H | R | 5-hydroxy-5-[5-(4-methyl-6-{[4-(1H-pyrazol-1-yl)pyridin-2-yl]amino}pyridin-2-yl)-1,3-thiazol-2-yl]-5,6,7,8-tetrahydronaphthalene-2-carboxylic acid | 525.2 | 525 | NH₄⁺ Salt |

TABLE 1-continued

| Ex. | R⁶ | R⁷ | R⁵ | R⁴ | * | IUPAC Name | [M + H]⁺ Calc'd | [M + H]⁺ Obs'd | Form |
|---|---|---|---|---|---|---|---|---|---|
| 1G | (thiophen-3-yl) | H | H | —CO₂H | R | 5-hydroxy-5-[5-(4-methyl-6-{[4-(thiophen-3-yl)pyridin-2-yl]amino}pyridin-2-yl)-1,3-thiazol-2-yl]-5,6,7,8-tetrahydronaphthalene-2-carboxylic acid | 541.1 | 541 | NH₄⁺ Salt |
| 1H | —CH₃ | H | H | —CO₂H | R | 5-hydroxy-5-(5-{4-methyl-6-[(4-methylpyridin-2-yl)amino]pyridin-2-yl}-1,3-thiazol-2-yl)-5,6,7,8-tetrahydronaphthalene-2-carboxylic acid | 473.2 | 473 | NH₄⁺ Salt |
| 1i | —O-cyclohexyl | H | H | —CO₂H | R | 5-[5-(6-{[4-(cyclohexyloxy)pyridin-2-yl]amino}-4-methylpyridin-2-yl)-1,3-thiazol-2-yl]-5-hydroxy-5,6,7,8-tetrahydronaphthalene-2-carboxylic acid | 557.2 | 557 | NH₄⁺ Salt |
| 1J | (3-methyl-1H-pyrazol-1-yl) | H | H | —CO₂H | R | 5-hydroxy-5-[5-(4-methyl-6-{[4-(3-methyl-1H-pyrazol-1-yl)pyridin-2-yl]amino}pyridin-2-yl)-1,3-thiazol-2-yl]-5,6,7,8-tetrahydronaphthalene-2-carboxylic acid | 539.2 | 539 | NH₄⁺ Salt |
| 1K | cyclobutyl | H | H | —CO₂H | R | 5-(5-{6-[(4-cyclobutylpyridin-2-yl)amino]-4-methylpyridin-2-yl}-1,3-thiazol-2-yl)-5-hydroxy-5,6,7,8-tetrahydronaphthalene-2-carboxylic acid | 513.2 | 513 | NH₄⁺ Salt |
| 1L | —O-cyclobutyl | H | H | —CO₂H | R | 5-[5-(6-{[4-(cyclobutyloxy)pyridin-2-yl]amino}-4-methylpyridin-2-yl)-1,3-thiazol-2-yl]-5-hydroxy-5,6,7,8-tetrahydronaphthalene-2-carboxylic acid | 529.2 | 529 | NH₄⁺ Salt |

TABLE 1-continued

| Ex. | R⁶ | R⁷ | R⁵ | R⁴ | * | IUPAC Name | [M + H]⁺ Calc'd | [M + H]⁺ Obs'd | Form |
|---|---|---|---|---|---|---|---|---|---|
| 1M | —CH₂CH₂CH₃ | H | H | —CO₂H | R | 5-hydroxy-5-(5-{4-methyl-6-[(4-propylpyridin-2-yl)amino]pyridin-2-yl}-1,3-thiazol-2-yl)-5,6,7,8-tetrahydronaphthalene-2-carboxylic acid | 501.2 | 501 | NH₄⁺ Salt |
| 1N | —OCH₂CH₃ | H | H | —CO₂H | R | 5-(5-{6-[(4-ethoxypyridin-2-yl)amino]-4-methylpyridin-2-yl}-1,3-thiazol-2-yl)-5-hydroxy-5,6,7,8-tetrahydronaphthalene-2-carboxylic acid | 503.2 | 503 | NH₄⁺ Salt |
| 1o | cyclopentyloxy | H | H | —CO₂H | R | 5-[5-(6-{[4-(cyclopentyloxy)pyridin-2-yl]amino}-4-methylpyridin-2-yl)-1,3-thiazol-2-yl]-5-hydroxy-5,6,7,8-tetrahydronaphthalene-2-carboxylic acid | 543.2 | 543 | NH₄⁺ Salt |
| 1P | —CH₂CH₃ | H | H | —CO₂H | R | 5-(5-{6-[(4-ethylpyridin-2-yl)amino]-4-methylpyridin-2-yl}-1,3-thiazol-2-yl)-5-hydroxy-5,6,7,8-tetrahydronaphthalene-2-carboxylic acid | 487.2 | 487 | NH₄⁺ Salt |
| 1Q | cyclohexyl | H | H | —CO₂H | R | 5-(5-{6-[(4-cyclohexylpyridin-2-yl)amino]-4-methylpyridin-2-yl}-1,3-thiazol-2-yl)-5-hydroxy-5,6,7,8-tetrahydronaphthalene-2-carboxylic acid | 541.2 | 541 | NH₄⁺ Salt |
| 1R | —OC(H)(CH₃)₂ | H | H | —CO₂H | R | 5-hydroxy-5-[5-(4-methyl-6-{[4-(propan-2-yloxy)pyridin-2-yl]amino}pyridin-2-yl)-1,3-thiazol-2-yl]-5,6,7,8-tetrahydronaphthalene-2-carboxylic acid | 517.2 | 517 | NH₄⁺ Salt |

TABLE 1-continued

| Ex. | R[6] | R[7] | R[5] | R[4] | * | IUPAC Name | [M + H]+ Calc'd | [M + H]+ Obs'd | Form |
|---|---|---|---|---|---|---|---|---|---|
| 1S | 5-methyl-1,3,4-oxadiazol-2-yl (via C) | H | H | —CO$_2$H | R | 5-hydroxy-5-[5-(4-methyl-6-{[4-(5-methyl-1,3,4-oxadiazol-2-yl)pyridin-2-yl]amino}pyridin-2-yl)-1,3-thiazol-2-yl]-5,6,7,8-tetrahydronaphthalene-2-carboxylic acid | 541.2 | 541 | TFA Salt |
| 1T | tetrahydrofuran-3-yloxy | H | H | —CO$_2$H | R | 5-hydroxy-5-[5-(4-methyl-6-{[4-(tetrahydrofuran-3-yloxy)pyridin-2-yl]amino}pyridin-2-yl)-1,3-thiazol-2-yl]-5,6,7,8-tetrahydronaphthalene-2-carboxylic acid | 545.2 | 545 | TFA Salt |
| 1U | cyclopropyl | H | H | —CO$_2$H | R | 5-(5-{6-[(4-cyclopropylpyridin-2-yl)amino]-4-methylpyridin-2-yl}-1,3-thiazol-2-yl)-5-hydroxy-5,6,7,8-tetrahydronaphthalene-2-carboxylic acid | 499.2 | 499 | TFA Salt |
| 1V | —C(H)(CH$_3$)$_2$ | H | H | —CO$_2$H | R | 5-hydroxy-5-[5-(4-methyl-6-{[4-(1-methylethyl)pyridin-2-yl]amino}pyridin-2-yl)-1,3-thiazol-2-yl]-5,6,7,8-tetrahydronaphthalene-2-carboxylic acid | 501.2 | 501 | TFA Salt |
| 1W | —C(CH$_3$)$_3$ | H | H | —CO$_2$H | R | 5-(5-{6-[(4-tert-butylpyridin-2-yl)amino]-4-methylpyridin-2-yl}-1,3-thiazol-2-yl)-5-hydroxy-5,6,7,8-tetrahydronaphthalene-2-carboxylic acid | 515.2 | 515 | NH$_4^+$ Salt |

Example 2

(R)-5-Hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid (2)

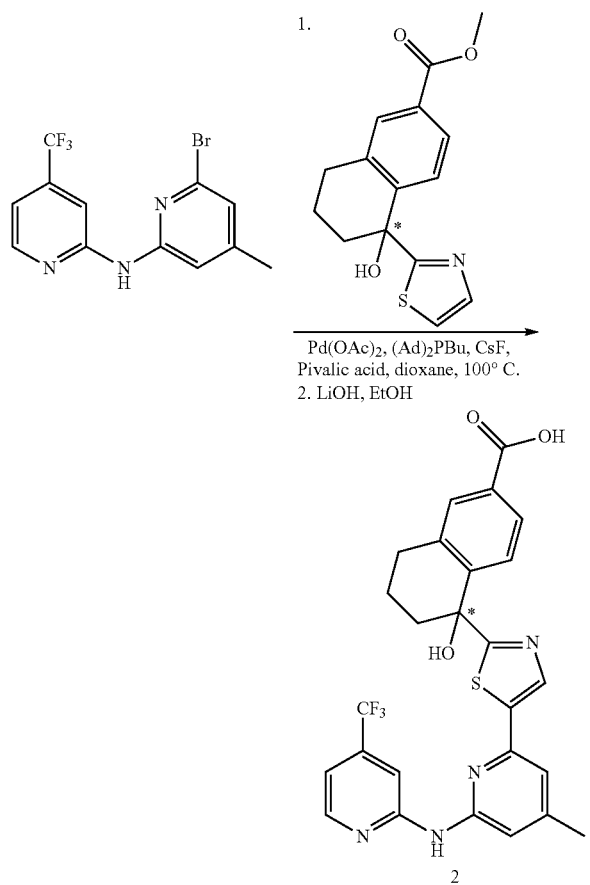

Step 1:

A suspension of butyl di-1-adamantylphosphine (5.95 g, 16.59 mmol) and Pd(OAc)₂ (1.862 g, 8.29 mmol) in 1,4-dioxane (100 mL) was stirred under nitrogen for 10 minutes and a yellow slurry was formed. 6-Bromo-4-methyl-N-(4-(trifluoromethyl)pyridin-2-yl)pyridin-2-amine (17.39 g, 52.4 mmol), (R)-methyl 5-hydroxy-5-(thiazol-2-yl)-5,6,7,8-tetrahydronaphthalene-2-carboxylate (enantiomer 2, 12 g, 41.5 mmol), cesium fluoride (18.90 g, 124 mmol), pivalic acid (7.22 mL, 62.2 mmol) and 1,4-dioxane (50 mL) were then added. The reaction mixture was vacuum purged with nitrogen 3 times and then heated to reflux under nitrogen for 20 hours. The reaction was cooled to rt and filtered through Celite®, washing through with EtOAc. The organic filtrate was washed sequentially with water and brine, dried (Na₂SO₄) and concentrated under reduced pressure. The residue was purified by silica gel column chromatography, eluting with 40% ethyl acetate in hexanes to afford the (R)-methyl 5-hydroxy-5-(5-(4-methyl-6-(4-(trifluoromethyl)pyridin-2-ylamino)pyridin-2-yl)thiazol-2-yl)-5,6,7,8-tetrahydronaphthalene-2-carboxylate as a pale yellow solid (18 g, 80% yield). MS ESI calcd for $C_{27}H_{23}F_3N_4O_3S$ [M+H]⁺ 541, found 541. ¹H NMR (500 MHz, DMSO) δ 10.20 (s, 1H), 8.63 (s, 1H), 8.48 (d, J=5.0 Hz, 1H), 8.23 (s, 1H), 7.74 (s, 1H), 7.69 (d, J=8.2 Hz, 1H), 7.36 (s, 1H), 7.23-7.17 (m, 2H), 7.09 (s, 1H), 6.63 (s, 1H), 3.82 (s, 3H), 2.92-2.85 (m, 2H), 2.33-2.30 (m, 4H), 2.15-2.09 (m, 1H), 2.02-1.88 (m, 2H) ppm.

Step 2:

To a suspension of (R)-methyl 5-hydroxy-5-(5-(4-methyl-6-(4-(trifluoromethyl)pyridin-2-ylamino)pyridin-2-yl)thiazol-2-yl)-5,6,7,8-tetrahydronaphthalene-2-carboxylate (12.8 g, 23.68 mmol) in EtOH (192 mL), was added 1N aqueous LiOH (83 mL, 83 mmol). The white suspension was heated to 45° C. for 4 h, during which time the reaction became bright yellow. The reaction was cooled to rt and acidified with 1N aqueous HCl to pH=4 during which time the product precipitated. Filtration afforded (R) 5-Hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid as an off white solid (11.5 g, 92% yield). MS ESI calcd for $C_{26}H_{21}F_3N_4O_3S$ [M+H]⁺ 527, found 527. ¹H NMR (500 MHz, DMSO) δ 12.85 (s, 1H), 10.20 (s, 1H), 8.64 (s, 1H), 8.48 (d, J=5.1 Hz, 1H), 8.23 (s, 1H), 7.72 (s, 1H), 7.66 (d, J=8.1 Hz, 1H), 7.38-7.31 (m, 2H), 7.21 (d, J=4.9 Hz, 1H), 7.10 (s, 1H), 6.60 (s, 1H), 2.92-2.82 (m, 2H), 2.40-2.33 (m, 1H), 2.30 (s, 3H), 2.15-2.08 (m, 1H), 2.03-1.88 (m, 2H) ppm.

Example 3

(rac)-Methyl-3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate, trifluoroacetate salt (3)

Step 1:

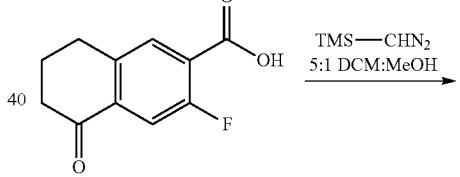

Step 2:

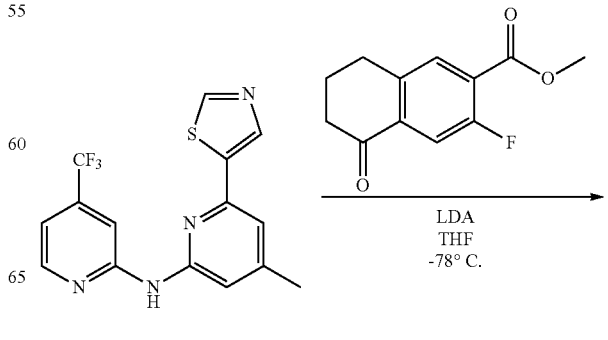

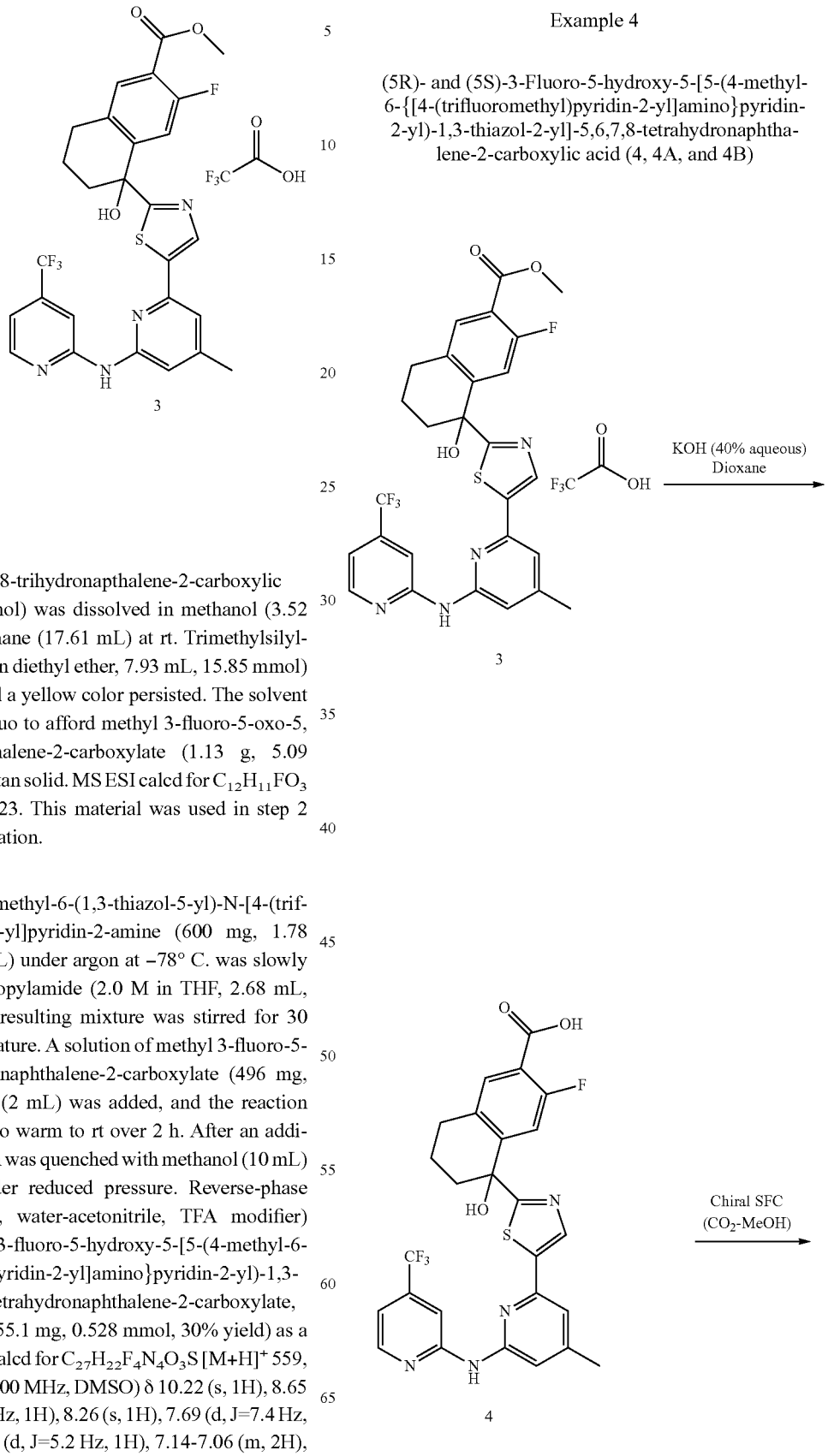

3.82 (s, 3H), 2.89-2.77 (m, 2H), 2.41-2.32 (m, 1H), 2.30 (s, 3H), 2.13-2.06 (m, 1H), 2.00-1.85 (m, 2H) ppm.

Example 4

(5R)- and (5S)-3-Fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid (4, 4A, and 4B)

Step 1:

3-Fluoro-5-oxo-6,7,8-trihydronapthalene-2-carboxylic acid (1.10 g, 5.28 mmol) was dissolved in methanol (3.52 mL) and dichloromethane (17.61 mL) at rt. Trimethylsilyldiazomethane (2.0 M in diethyl ether, 7.93 mL, 15.85 mmol) was added slowly until a yellow color persisted. The solvent was evaporated in vacuo to afford methyl 3-fluoro-5-oxo-5,6,7,8-tetrahydronaphthalene-2-carboxylate (1.13 g, 5.09 mmol, 96% yield) as a tan solid. MS ESI calcd for $C_{12}H_{11}FO_3$ [M+H]$^+$ 223, found 223. This material was used in step 2 without further purification.

Step 2:

To a solution of 4-methyl-6-(1,3-thiazol-5-yl)-N-[4-(trifluoromethyl)pyridin-2-yl]pyridin-2-amine (600 mg, 1.78 mmol) in THF (5.9 mL) under argon at −78° C. was slowly added lithium diisopropylamide (2.0 M in THF, 2.68 mL, 5.35 mmol), and the resulting mixture was stirred for 30 minutes at that temperature. A solution of methyl 3-fluoro-5-oxo-5,6,7,8-tetrahydronaphthalene-2-carboxylate (496 mg, 2.230 mmol) in THF (2 mL) was added, and the reaction mixture was allowed to warm to rt over 2 h. After an additional 12 h, the reaction was quenched with methanol (10 mL) and concentrated under reduced pressure. Reverse-phase HPLC (C18 column, water-acetonitrile, TFA modifier) afforded (rac)-methyl 3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate, trifluoroacetate salt (355.1 mg, 0.528 mmol, 30% yield) as a yellow solid. MS ESI calcd for $C_{27}H_{22}F_4N_4O_3S$ [M+H]$^+$ 559, found 559. $^1$H NMR (500 MHz, DMSO) δ 10.22 (s, 1H), 8.65 (s, 1H), 8.48 (d, J=5.2 Hz, 1H), 8.26 (s, 1H), 7.69 (d, J=7.4 Hz, 1H), 7.37 (s, 1H), 7.21 (d, J=5.2 Hz, 1H), 7.14-7.06 (m, 2H), -continued

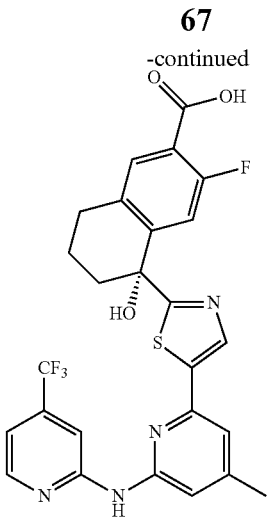

4A/4B

Step 1:

To a solution of methyl 3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate, trifluoroacetate salt (200 mg, 0.297 mmol) in tetrahydrofuran (1.2 mL) under argon was added potassium hydroxide (40% aqueous solution, 834 µl, 5.95 mmol), and the reaction was stirred at rt for 16 h. The pH was adjusted to 5 by the addition of aqueous HCl (2.0 M). The resulting mixture was extracted with ethyl acetate (3 times), and the combined organic phases were dried ($Na_2SO_4$) and concentrated under reduced pressure to afford (rac)-3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid (115.0 mg, 0.211 mmol, 71% yield) as a light yellow solid. MS ESI calcd for $C_{26}H_{20}F_4N_4O_3S$ [M+H]$^+$ 545, found 545.

Step 2:

3-Fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid (100 mg, 0.184 mmol) was purified via chiral supercritical fluid chromatography on an AD-H column eluting with $CO_2$-methanol to yield (5R)- and (5S)-3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid as two white solids.

Isomer 4A (first eluting enantiomer): (38.1 mg, 0.070 mmol, 38% yield) MS ESI calcd for $C_{26}H_{20}F_4N_4O_3S$ [M+H]$^+$ 545, found 545. $^1$H NMR (600 MHz, DMSO) δ 10.19 (s, 1H), 8.63 (s, 1H), 8.46 (d, J=5.1 Hz, 1H), 8.23 (s, 1H), 7.62 (d, J=7.3 Hz, 1H), 7.35 (s, 1H), 7.19 (d, J=4.6 Hz, 1H), 7.07 (s, 1H), 7.03 (d, J=11.8 Hz, 1H), 6.71 (s, 1H), 2.85-2.73 (m, 2H), 2.37-2.31 (m, 1H), 2.28 (s, 3H), 2.10-2.03 (m, 1H), 1.98-1.83 (m, 2H) ppm.

Isomer 4B: (38.9 mg, 0.071 mmol, 39% yield) MS ESI calcd for $C_{26}H_{20}F_4N_4O_3S$ [M+H]$^+$ 545, found 545. $^1$H NMR (600 MHz, DMSO) δ 10.19 (s, 1H), 8.63 (s, 1H), 8.46 (d, J=5.1 Hz, 1H), 8.23 (s, 1H), 7.62 (d, J=7.3 Hz, 1H), 7.35 (s, 1H), 7.19 (d, J=5.0 Hz, 1H), 7.07 (s, 1H), 7.03 (d, J=11.8 Hz, 1H), 6.71 (s, 1H), 2.84-2.74 (m, 2H), 2.38-2.31 (m, 1H), 2.28 (s, 3H), 2.11-2.04 (m, 1H), 1.98-1.85 (m, 2H) ppm.

Example 5

(rac)-7-Fluoro-6-(hydroxymethyl)-1-[5-(4-methyl-6-{[4-(trifluoromethyl)pyridin-2-yl]amino}pyridin-2-yl)-1,3-thiazol-2-yl]-1,2,3,4-tetrahydronaphthalen-1-ol, trifluoroacetate salt (5)

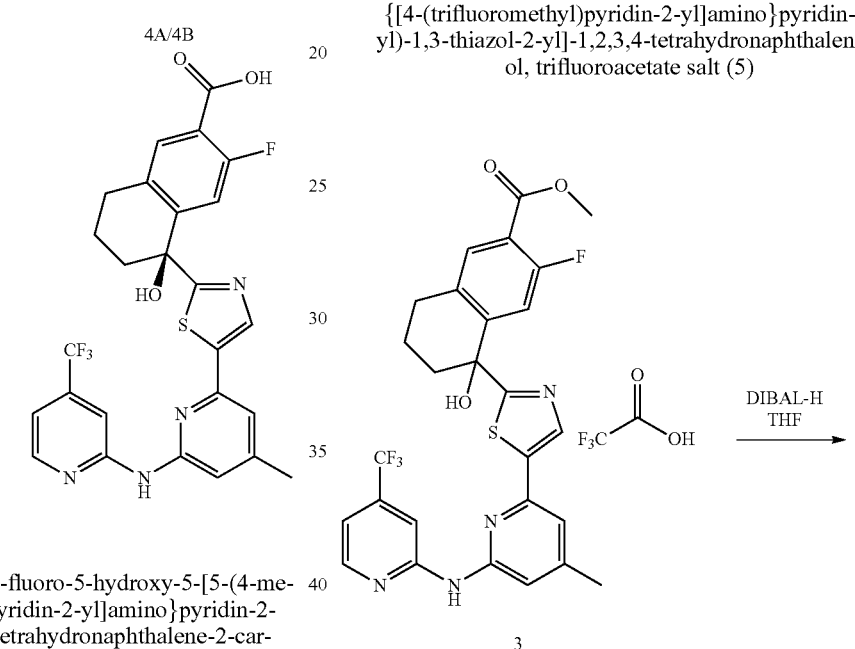

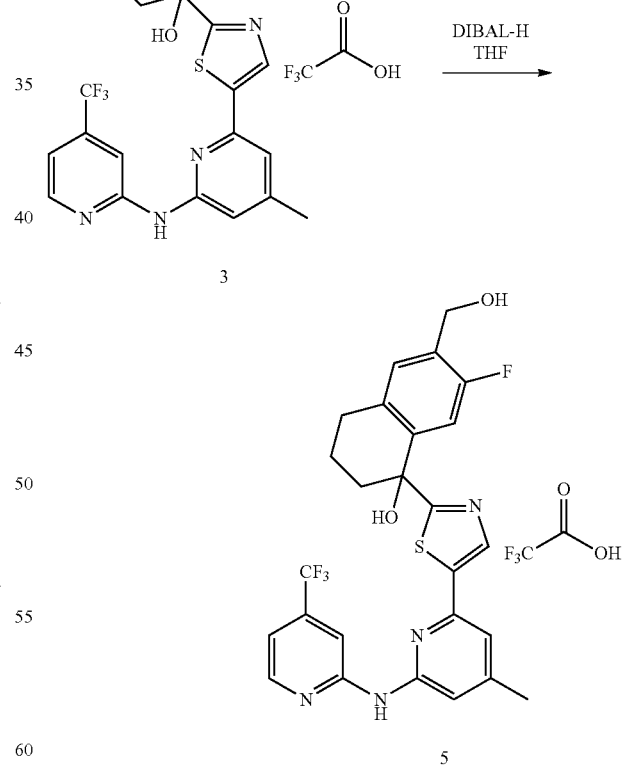

To a solution of methyl 3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate, trifluoroacetate salt (50 mg, 0.074 mmol) in THF (1.5 mL) under argon at rt was added dropwise diisobutylaluminum hydride (1.0 M in THF, 223 µL, 0.223 mmol), and the reaction was stirred at rt for 16 hours. The reaction was quenched with methanol (1.5 mL) and trifluoroacetic acid (0.5 mL), and then diluted with DMSO (1 mL). This mixture was barrier filtered and purified by reverse-phase HPLC (C18 column, water-acetonitrile, TFA modifier) to yield (rac)-7-fluoro-6-(hydroxymethyl)-1-[5-(4-methyl-6-{[4-(trifluoromethyl)pyridin-2-yl]amino}pyridin-2-yl)-1,3-thiazol-2-yl]-1,2,3,4-tetrahydronaphthalen-1-ol, trifluoroacetate salt (6.0 mg, 0.00931 mmol, 13% yield) as a yellow solid. MS ESI calcd for $C_{26}H_{22}F_4N_4O_2S$ [M+H]$^+$ 531, found 531. $^1$H NMR (500 MHz, DMSO) δ 10.21 (s, 1H), 8.65 (s, 1H), 8.48 (d, J=5.1 Hz, 1H), 8.23 (s, 1H), 7.36 (s, 1H), 7.24-7.19 (m, 2H), 7.09 (s, 1H), 6.89 (d, J=11.3 Hz, 1H), 4.47 (d, J=0.6 Hz, 2H), 2.83-2.73 (m, 2H), 2.40-2.33 (m, 1H), 2.30 (s, 3H), 2.11-2.04 (m, 1H), 2.02-1.86 (m, 2H).

Example 6

(rac)-Methyl 5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate (6)

Step 1:

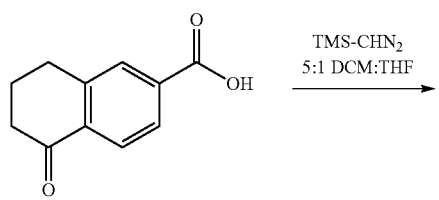

Step 2:

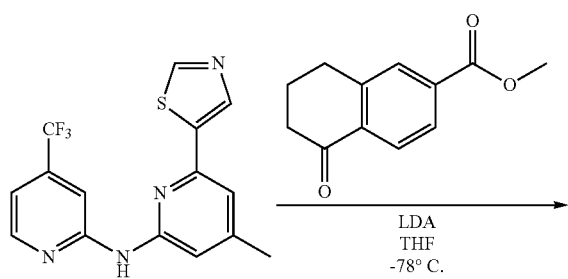

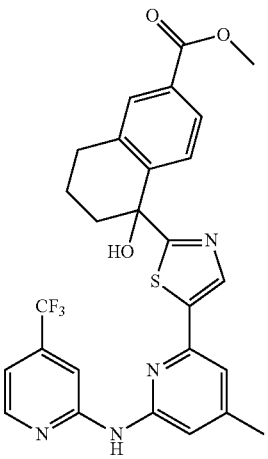

Step 1:

To a solution of 5-oxo-5,6,7,8-tetrahydronaphthalene-2-carboxylic acid (10.0 g, 52.6 mmol) in THF (52.6 mL) and MeOH (10.64 mL, 263 mmol) at rt was added trimethylsilyldiazomethane (2.0 M in diethyl ether, 79 mL, 158 mmol) dropwise until the solution turned yellow and gas evolution ceased. The reaction was then concentrated under reduced pressure to give methyl 5-oxo-5,6,7,8-tetrahydronaphthalene-2-carboxylate (10.72 g, 52.5 mmol, 100% yield) as a brown solid. MS ESI calcd for $C_{12}H_{12}O_3$ [M+H]$^+$ 205, found 205. $^1$H NMR (500 MHz, DMSO) δ 7.94 (d, J=8.1 Hz, 1H), 7.91 (s, 1H), 7.85 (dd, J=8.1, 1.6 Hz, 1H), 3.86 (s, 3H), 2.99 (t, J=6.0 Hz, 2H), 2.66-2.61 (m, 2H), 2.09-2.00 (m, 2H).

Step 2:

To a solution of 4-methyl-6-(1,3-thiazol-5-yl)-N-[4-(trifluoromethyl)pyridin-2-yl]pyridin-2-amine (500 mg, 1.487 mmol) in THF (5.9 mL) under argon at −78° C. was added lithium diisopropylamide (2.0 M in tetrahydrofuran, 2.2 mL, 4.46 mmol), and the resulting mixture was stirred as such for 30 minutes. To this mixture was added a solution of methyl 5-oxo-5,6,7,8-tetrahydronaphthalene-2-carboxylate (379 mg, 1.858 mmol) in THF (2 mL), and the reaction was then allowed to warm to rt over a period of 2 h. After stirring for an additional 14 h, the reaction was quenched with methanol (10 mL) and directly concentrated. Chromatography on silica gel (dichloromethane-methanol) afforded (rac)-methyl 5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate as a light brown solid (718.0 mg, 1.328 mmol, 89% yield). MS ESI calcd for $C_{27}H_{23}F_3N_4O_3S$ [M+H]$^+$ 541, found 541. $^1$H NMR (500 MHz, DMSO) δ 10.20 (s, 1H), 8.63 (s, 1H), 8.48 (d, J=5.0 Hz, 1H), 8.23 (s, 1H), 7.74 (s, 1H), 7.69 (d, J=8.2 Hz, 1H), 7.36 (s, 1H), 7.23-7.17 (m, 2H), 7.09 (s, 1H), 6.63 (s, 1H), 3.82 (s, 3H), 2.92-2.85 (m, 2H), 2.33-2.30 (m, 4H), 2.15-2.09 (m, 1H), 2.02-1.88 (m, 2H) ppm.

1H), 7.36 (s, 1H), 7.33 (d, J=8.2 Hz, 1H), 7.21 (d, J=5.1 Hz, 1H), 7.10 (s, 1H), 2.92-2.83 (m, 2H), 2.41-2.33 (m, 1H), 2.31 (s, 3H), 2.16-2.07 (m, 1H), 2.04-1.90 (m, 2H) ppm.

Example 7

(rac)-5-Hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid, trifluoroacetate salt

Example 8

Isolation of (5S) and (5R) 5-Hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid, trifluoroacetate salt (8 and 2)

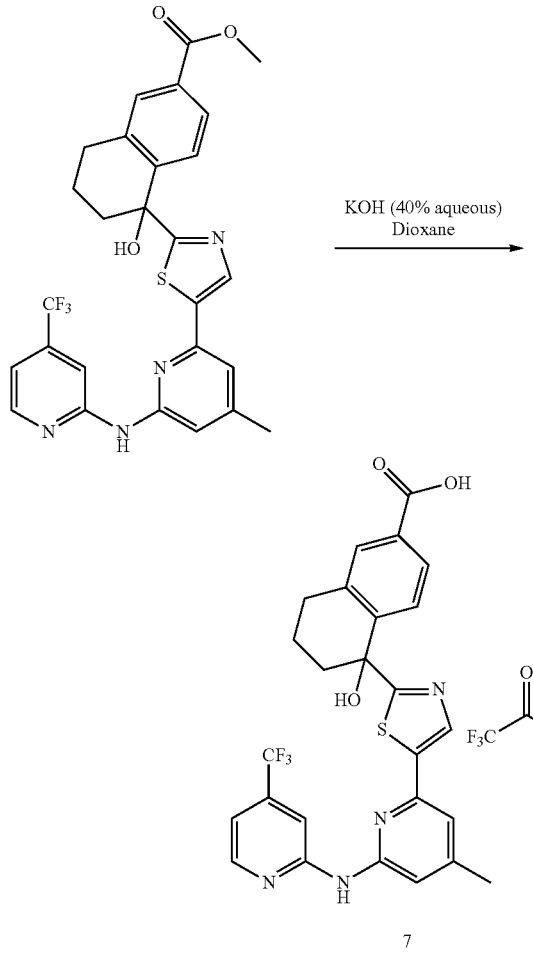

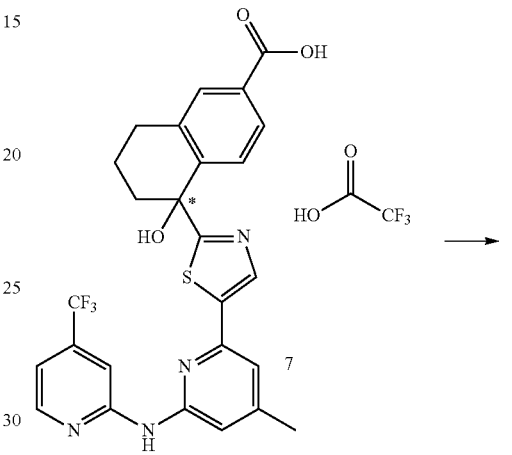

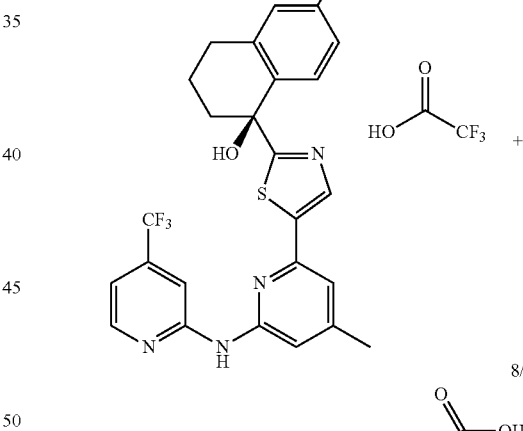

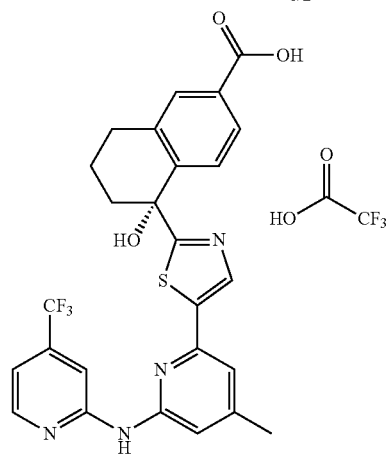

To a solution of (rac)-methyl 5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate (250 mg, 0.462 mmol) in THF (1.9 mL) was added potassium hydroxide (40% solution in water, 1.3 mL, 9.25 mmol), and the reaction was stirred at rt for three days. The reaction was diluted with methanol (2 mL) and DMSO (2 mL), barrier filtered, and purified via reverse-phase HPLC (C18 column, water-acetonitrile, TFA modifier) to yield (rac)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid, trifluoroacetate salt as a light brown solid (133.8 mg, 0.209 mmol, 45% yield). MS ESI calcd for $C_{26}H_{21}F_3N_4O_3S$ [M+H]$^+$ 527, found 527. $^1$H NMR (500 MHz, DMSO) δ 10.21 (s, 1H), 8.63 (s, 1H), 8.48 (d, J=5.1 Hz, 1H), 8.23 (s, 1H), 7.72 (s, 1H), 7.66 (d, J=8.0 Hz, (rac)-5-Hydroxy-5-[5-(4-methyl-6-{[4-(trifluoromethyl) pyridin-2-yl]amino}pyridin-2-yl)-1,3-thiazol-2-yl]-5,6,7,8-tetrahydronaphthalene-2-carboxylic acid, trifluoroacetate salt (70 mg, 0.109 mmol) was purified via chiral supercritical fluid chromatography on an AD-H column eluting with $CO_2$-ethanol to yield (5S)- and (5R)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid, trifluoroacetate salt as two white solids. Isomer 8 (first eluting enantiomer): (33.2 mg, 0.052 mmol, 47% yield) MS ESI calcd for $C_{26}H_{21}F_3N_4O_3S$ [M+H]$^+$ 527, found 527. $^1$H NMR (500 MHz, DMSO) δ 10.20 (s, 1H), 8.64 (s, 1H), 8.48 (s, 1H), 8.23 (s, 1H), 7.69 (s, 1H), 7.65 (d, J=8.2 Hz, 1H), 7.35 (s, 1H), 7.32 (d, J=8.1 Hz, 1H), 7.20 (s, 1H), 7.10 (s, 1H), 6.59 (s, 1H), 2.90-2.83 (m, 2H), 2.41-2.33 (m, 1H), 2.30 (s, 3H), 2.15-2.07 (m, 1H), 2.04-1.89 (m, 2H) ppm.

Isomer which is the same compound as prepared in Example 2 (second eluting enantiomer): (34.1 mg, 0.053 mmol, 49% yield) MS ESI calcd for $C_{26}H_{21}F_3N_4O_3S$ [M+H]$^+$ 527, found 527. $^1$H NMR (500 MHz, DMSO) δ 10.20 (s, 1H), 8.64 (s, 1H), 8.48 (s, 1H), 8.23 (s, 1H), 7.71 (s, 1H), 7.65 (d, J=8.2 Hz, 1H), 7.35 (s, 1H), 7.32 (d, J=8.2 Hz, 1H), 7.21 (s, 1H), 7.10 (s, 1H), 6.59 (s, 1H), 2.90-2.83 (m, 2H), 2.40-2.33 (m, 1H), 2.30 (s, 3H), 2.15-2.08 (m, 1H), 2.04-1.89 (m, 2H) ppm. This isomer was determined to be the R enantiomer.

Example 9

(rac)-5-Hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide, trifluoroacetate salt (9)

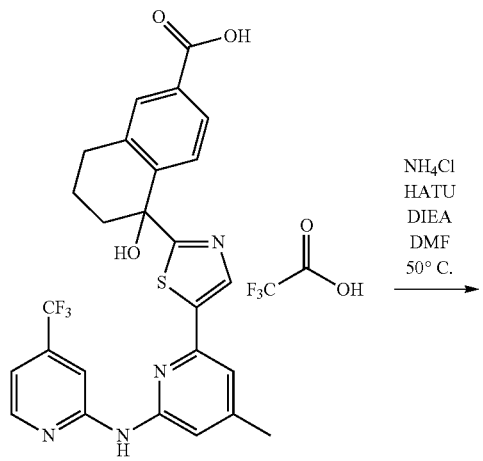

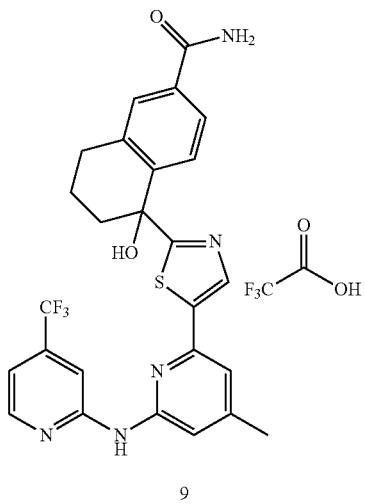

To a solution of (rac)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid, trifluoroacetate salt (50 mg, 0.078 mmol), ammonium chloride (62.6 mg, 1.171 mmol), and O-(7-azabenzotriazol-1-yl)-N,N,N',N'-tetramethyluronium hexafluorophosphate (44.5 mg, 0.117 mmol) in DMF (781 µL) was added diisopropylethylamine (40.9 µl, 0.234 mmol), and the reaction was heated at 50° C. for 16 h. The reaction mixture was then diluted with DMSO (1 mL), barrier filtered, and purified by reverse-phase HPLC (C18 column, water-acetonitrile, TFA modifier) to give (rac)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide, trifluoroacetate salt (27.4 mg, 0.043 mmol, 43% yield) as a yellow solid. MS ESI calcd for $C_{26}H_{22}F_3N_5O_2S$ [M+H]$^+$ 526, found 526. $^1$H NMR (500 MHz, DMSO) δ 10.21 (s, 1H), 8.64 (s, 1H), 8.48 (s, 1H), 8.22 (s, 1H), 7.88 (s, 1H), 7.64 (s, 1H), 7.57 (s, 1H), 7.35 (s, 1H), 7.28 (s, 1H), 7.25 (d, J=8.2 Hz, 1H), 7.21 (d, J=4.5 Hz, 1H), 7.11 (s, 1H), 2.89-2.80 (m, 2H), 2.39-2.32 (m, 1H), 2.30 (s, 3H), 2.15-2.07 (m, 1H), 2.04-1.89 (m, 2H) ppm.

Example 10

(R)-methyl 5-(5-(6-((4-(1H-1,2,3-triazol-4-yl)pyridin-2-yl)amino)-4-methylpyridin-2-yl)thiazol-2-yl)-5-hydroxy-5,6,7,8-tetrahydronaphthalene-2-carboxylate (10)

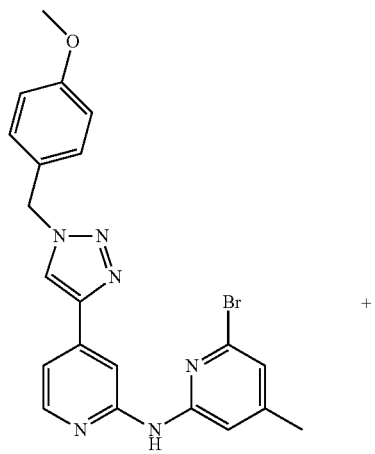

+

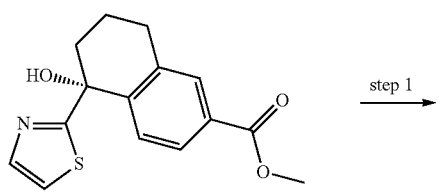

step 1 →

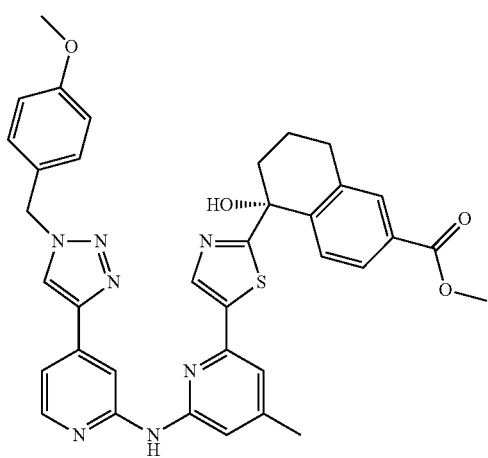

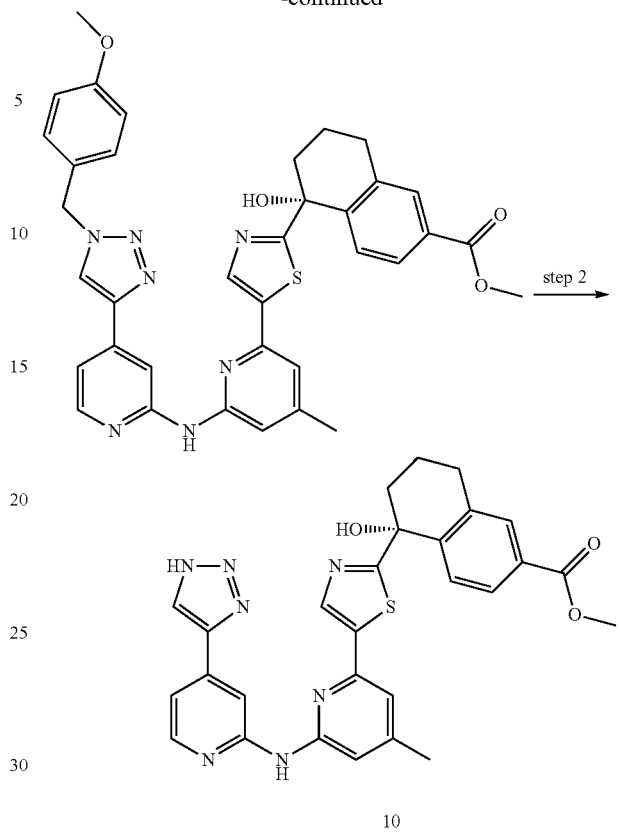

Step 1:

To microwave vial were added 6-bromo-N-(4-(1-(4-methoxybenzyl)-1H-1,2,3-triazol-4-yl)pyridin-2-yl)-4-methylpyridin-2-amine (247 mg, 0.547 mmol), (R)-methyl 5-hydroxy-5-(thiazol-2-yl)-5,6,7,8-tetrahydronaphthalene-2-carboxylate (158 mg, 0.547 mmol), butyldi-1-adamantylphosphine (78 mg, 0.219 mmol), CsF (249 mg, 1.64 mmol), pivalic acid (95 μl, 0.821 mmol), and Pd(OAc)$_2$ (24.6 mg, 0.109 mmol). The reaction was vacuum and purged with argon 3 times, then degassed 1,4-Dioxane (2.0 mL) was added and the reaction was heated to 100° C. for 16 h. The reaction was cooled to rt and diluted with EtOAc (20 mL). The reaction was filtered, concentrated and purified by silica gel chromatography using a gradient solvent system of 30-100% EtOAc/Hexanes. The product-containing fractions were collected and concentrated to give (R)-methyl 5-hydroxy-5-(5-(6-((4-(1-(4-methoxybenzyl)-1H-1,2,3-triazol-4-yl)pyridin-2-yl)amino)-4-methylpyridin-2-yl)thiazol-2-yl)-5,6,7,8-tetrahydronaphthalene-2-carboxylate (121 mg, 34%) as a white foam. MS ESI calcd for $C_{36}H_{33}N_7O_4S$ [M+H]$^+$ 660, found 660.

Step 2:

To a microwave vial were added (R)-methyl 5-hydroxy-5-(5-(6-((4-(1-(4-methoxybenzyl)-1H-1,2,3-triazol-4-yl)pyridin-2-yl)amino)-4-methylpyridin-2-yl)thiazol-2-yl)-5,6,7,8-tetrahydronaphthalene-2-carboxylate (100 mg, 0.152 mmol) and TFA (1.53 mL) and the solution was heated to 30° C. for 2 days at which time the reaction was concentrated and purified by reverse phase HPLC using a C18 column eluting with MeCN/H$_2$O modified with 0.1% TFA. The product containing fractions were lyopholyzed to give the trifluoroacetate salt of (R)-methyl 5-(5-(6-((4-(1H-1,2,3-triazol-4-yl)pyridin-2-yl)amino)-4-methylpyridin-2-yl)thiazol-2-yl)-5-hydroxy-5, 6,7,8-tetrahydronaphthalene-2-carboxylate (7.5 mg, 8%) as a white powder. MS ESI calcd for $C_{28}H_{25}N_7O_3S$ [M+H]+ 540, found 540. $^1$H NMR (600 MHz, dmso) δ 10.36 (br s, 1H), 8.35 (s, 1H), 8.30 (s, 1H), 8.28 (s, 1H), 7.73 (s, 1H), 7.67 (d, J=8.0, 1H), 7.47 (s, 1H), 7.33 (d, J=8.2, 2H), 7.15 (s, 1H), 6.68 (br s, 2H), 3.80 (s, 3H), 2.88 (s, 2H), 2.50 (s, 1H), 2.32 (s, 3H), 2.11-2.10 (m, 1H), 2.04-1.98 (m, 1H), 1.97-1.91 (m, 1H) ppm.

Example 11

(R)-5-(5-(6-((4-(1H-1,2,3-triazol-4-yl)pyridin-2-yl)amino)-4-methylpyridin-2-yl)thiazol-2-yl)-5-hydroxy-5,6,7,8-tetrahydronaphthalene-2-carboxylic acid (11)

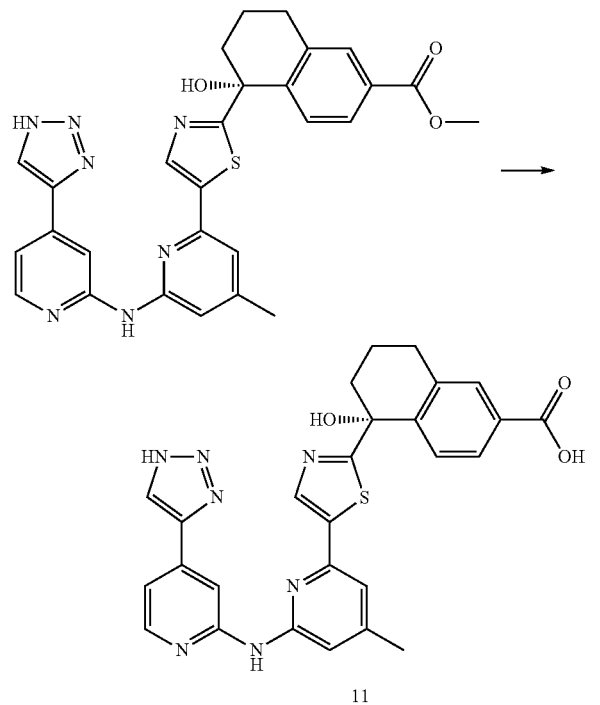

To a flask containing (R)-methyl 5-(5-(6-((4-(1H-1,2,3-triazol-4-yl)pyridin-2-yl)amino)-4-methylpyridin-2-yl)thiazol-2-yl)-5-hydroxy-5,6,7,8-tetrahydronaphthalene-2-carboxylate (5 mg, 7.65 μmol) in THF (695 μl) and ethanol (69.5 μl) was added KOH (6.50 μl, 0.061 mmol) and the mixture was heated to 50° C. for 4 hrs. TFA (5.19 μl, 0.067 mmol) was added and the mixture was concentrated under reduced pressure. The product was purified by reverse phase HPLC using a C18 column and MeCN and water modified with 0.1% TFA as mobile phase. The product-containing fractions were collected and lyophilized to give the trifluoroacetate salt of (R)-5-(5-(6-((4-(1H-1,2,3-triazol-4-yl)pyridin-2-yl)amino)-4-methylpyridin-2-yl)thiazol-2-yl)-5-hydroxy-5,6,7,8-tetrahydronaphthalene-2-carboxylic acid (2.5 mg, 51%) as a white solid. MS ESI calcd for $C_{27}H_{23}N_7O_3S$ [M+H]+ 526, found 526. $^1$H NMR (600 MHz, dmso) δ 12.83 (br s, 1H), 9.96 (br s, 1H), 8.39 (s, 1H), 8.30 (s, 1H), 8.27-8.22 (m, 2H), 7.70 (s, 1H), 7.64 (d, J=8.1, 1H), 7.39 (s, 1H), 7.34-7.26 (m, 2H), 7.23 (s, 1H), 6.61 (s, 1H), 2.87 (br s, 2H), 2.34 (t, J=11.1, 1H), 2.30 (s, 3H), 2.18-2.07 (m, 1H), 2.07-1.97 (m, 1H), 1.97-1.89 (m, 1H) ppm.

Example 12

Compounds of Formula (I) Containing Bromo Substituents at $R^8$ and/or $R^9$ (13A, 13B, and 13C)

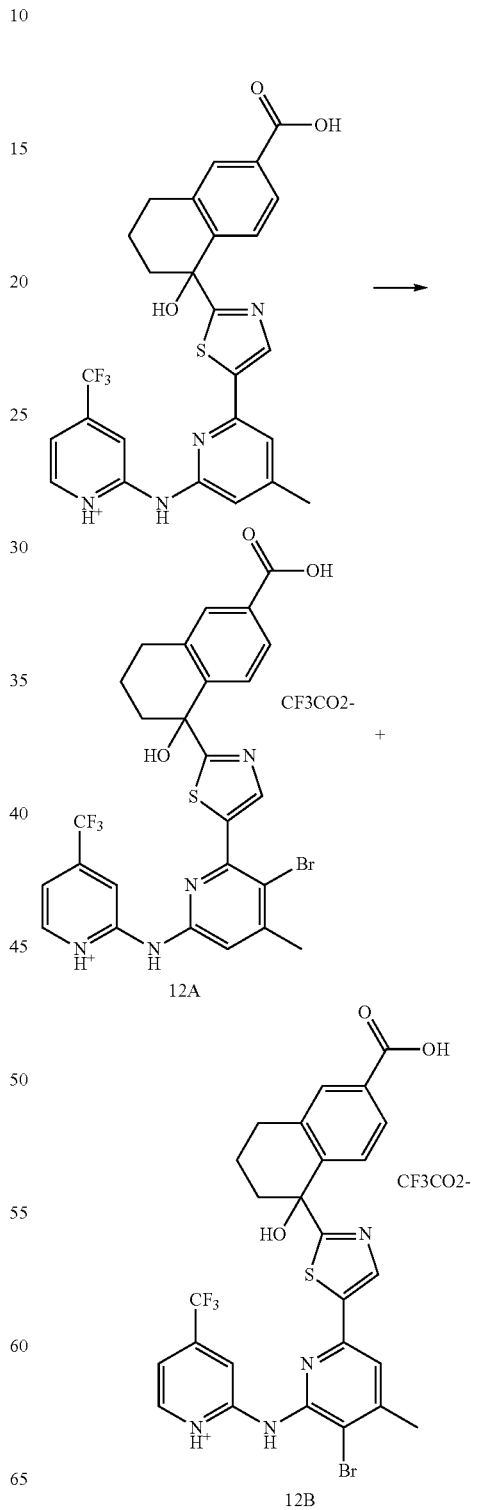

-continued

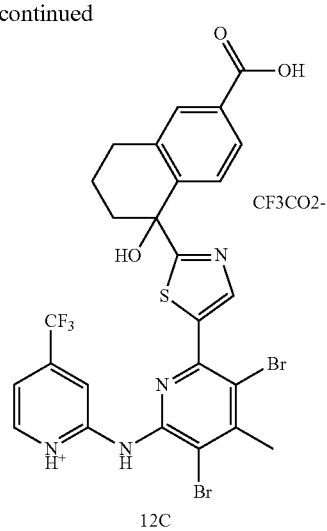

12C

To a solution of (R) 5-Hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid (100 mg, 0.19 mmol) in DMF (1.5 mL) at rt was added N-bromosuccinimide (34 mg, 0.19 mmol) portionwise over 10 minutes. The reaction was then stirred for 16 hr at rt. The mixture of products was purified by reverse phase hplc using a C18 column with a mobile phase of MeCN and water modified with 0.1% TFA to give the following products:

12A:

(R)-2-((5-bromo-6-(2-(6-carboxy-1-hydroxy-1,2,3,4-tetrahydronaphthalen-1-yl)thiazol-5-yl)-4-methylpyridin-2-yl)amino)-4-(trifluoromethyl)pyridin-1-ium trifluoroacetate. MS ESI calcd for $C_{26}H_{21}BrF_3N_4O_3S$ [M+H]$^+$ 605, found 605. $^1$H NMR (600 MHz, DMSO) δ 10.33 (s, 1H), 8.49 (d, J=5.1 Hz, 1H), 8.46 (s, 1H), 8.39 (s, 1H), 7.71 (s, 1H), 7.63 (d, J=8.2 Hz, 1H), 7.35 (s, 1H), 7.29 (d, J=8.2 Hz, 1H), 7.22 (d, J=5.1 Hz, 1H), 2.86 (m, 2H), 2.38 (s, 3H), 2.34 (t, J=9.9 Hz, 1H), 2.15-2.07 (m, 1H), 2.00 (m, 1H), 1.94 (m, 1H) ppm.

12B:

(R)-2-((3-bromo-6-(2-(6-carboxy-1-hydroxy-1,2,3,4-tetrahydronaphthalen-1-yl)thiazol-5-yl)-4-methylpyridin-2-yl)amino)-4-(trifluoromethyl)pyridin-1-ium trifluoroacetate. MS ESI calcd for $C_{26}H_{21}BrF_3N_4O_3S$ [M+H]$^+$ 605, found 605. $^1$H NMR (600 MHz, DMSO) δ 8.60 (1H, s), 8.59 (s, 1H), 8.52 (d, J=5.1 Hz, 1H), 8.27 (s, 1H), 7.70 (s, 1H), 7.63 (d, J=8.2 Hz, 1H), 7.61 (s, 1H), 7.35 (d, J=5.1 Hz, 1H), 7.29 (d, J=8.2 Hz, 1H), 2.85 (m, 2H), 2.40 (s, 3H), 2.32 (m, 1H), 2.09 (m, 1H), 2.05-1.85 (m, 2H) ppm.

12C:

2(R)-2-((3,5-dibromo-6-(2-(6-carboxy-1-hydroxy-1,2,3,4-tetrahydronaphthalen-1-yl)thiazol-5-yl)-4-methylpyridin-2-yl)amino)-4-(trifluoromethyl)pyridin-1-ium trifluoroacetate. MS ESI calcd for $C_{26}H_{20}Br_2F_3N_4O_3S$ [M+H]$^+$ 685, found 685. $^1$H NMR (600 MHz, DMSO) δ 8.78 (s, 1H), 8.53 (d, J=5.1 Hz, 1H), 8.46 (s, 1H), 8.37 (s, 1H), 7.70 (s, 1H), 7.62 (d, J=8.1 Hz, 1H), 7.36 (d, J=5.1 Hz, 1H), 7.27 (d, J=8.2 Hz, 1H), 2.86 (m, 2H), 2.65 (s, 3H), 2.32 (m, 1H), 2.11 (m, 1H), 2.00 (m, 1H), 1.96-1.88 (m, 1H) ppm.

Example 13

(R)-5-(5-(4-acetamido-6-((4-(trifluoromethyl)pyridin-2-yl)amino)pyridin-2-yl)thiazol-2-yl)-5-hydroxy-5,6,7,8-tetrahydronaphthalene-2-carboxylic acid (13A and 13B)

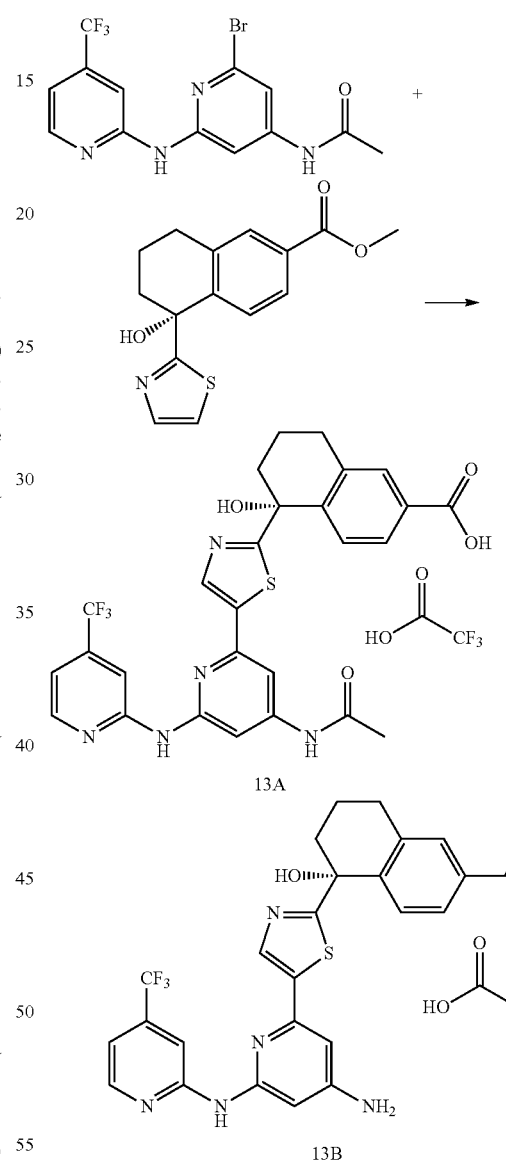

To a microwave vial was added 6-bromo-4-methyl-N-(4-(trifluoromethyl)pyridin-2-yl)pyridin-2-amine (200 mg, 0.533 mmol), (R)-methyl 5-hydroxy-5-(thiazol-2-yl)-5,6,7,8-tetrahydronaphthalene-2-carboxylate (154 mg, 0.533 mmol), Pd(OAc)$_2$ (23.94 mg, 0.107 mmol), butyl-diadamantylphosphine (76 mg, 0.213 mmol), CsF$_2$ (243 mg, 1.599 mmol), and pivalic acid (93 μl, 0.800 mmol) vacuum purged with argon 3 times. Degassed dioxane (1.8 mL) was added to the reaction mixture, which was then sealed and stirred at 100° C. for 16 h. After cooling to rt aqueous potassium hydroxide (567 μl, 5.33 mmol) was added. The mixture was resealed and stirred at rt for 4 hours. The mixture was diluted with MeOH (1 mL) and DMSO (1 mL), filtered, and purified by reverse phase HPLC using a C18 column and a solvent system of MeCN and water modified with 0.1% TFA. The product-containing fractions were collected and concentrated.

13A:

(R)-5-(5-(4-acetamido-6-((4-(trifluoromethyl)pyridin-2-yl)amino)pyridin-2-yl)thiazol-2-yl)-5-hydroxy-5,6,7,8-tetrahydronaphthalene-2-carboxylic acid, trifluoroacetate salt (68 mg, 20%), white solid. MS ESI calcd for $C_{27}H_{22}F_3N_5O_4S$ [M+H]$^+$ 570, found 570. $^1$H NMR (600 MHz, dmso) δ 10.36 (s, 1H), 10.25 (s, 1H), 8.56 (s, 1H), 8.45 (d, J=5.1, 1H), 8.02 (s, 1H), 7.70 (s, 1H), 7.64 (d, J=8.1, 1H), 7.57 (s, 1H), 7.55 (d, J=1.4, 1H), 7.31 (d, J=8.2, 1H), 7.18 (d, J=4.2, 1H), 2.93-2.78 (m, 2H), 2.34 (dd, J=11.5, 7.7, 1H), 2.16-2.08 (m, 1H), 2.06 (s, 3H), 2.04-1.95 (m, 1H), 1.95-1.87 (m, 1H) ppm.

13B:

(R)-5-(5-(4-amino-6-((4-(trifluoromethyl)pyridin-2-yl)amino)pyridin-2-yl)thiazol-2-yl)-5-hydroxy-5,6,7,8-tetrahydronaphthalene-2-carboxylic acid, trifluoroacetate salt (119 mg, 33%), light yellow solid. MS ESI calcd for $C_{25}H_{20}F_3N_5O_3S$ [M+H]$^+$ 528, found 528. $^1$H NMR (600 MHz, dmso) δ 12.92 (br s, 1H), 8.56 (s, 1H), 8.15 (s, 1H), 7.71 (s, 1H), 7.65 (d, J=8.2, 1H), 7.28 (d, J=8.2, 2H), 6.76 (br s, 1), 6.71 (s, 1H), 6.34 (s, 1H), 2.95-2.79 (m, 2H), 2.38-2.26 (m, 1H), 2.19-2.08 (m, 1H), 2.08-1.97 (m, 1H), 1.97-1.88 (m, 1H) ppm.

Example 14

Methyl (R and S) 5-hydroxy-5-(5-(4-methyl-6-((4-(trifluoromethyl)pyridin-2-yl)amino)pyridin-2-yl)thiazol-2-yl)-5,6,7,8-tetrahydronaphthalene-1-carboxylate (14A and 14B)

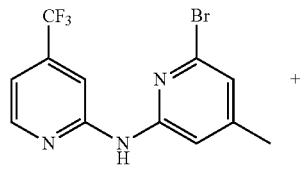

+

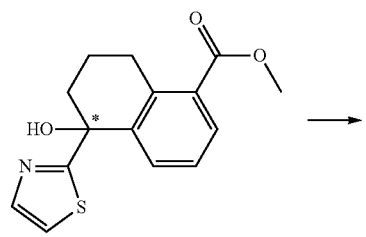

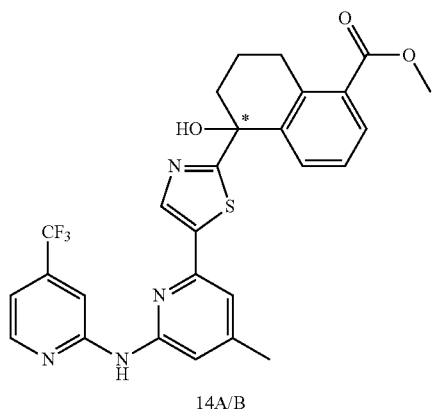

14A/B

To a microwave vial were added (R or S)-methyl 5-hydroxy-5-(thiazol-2-yl)-5,6,7,8-tetrahydronaphthalene-1-carboxylate (0.075 g, 0.259 mmol), 6-bromo-4-methyl-N-(4-(trifluoromethyl)pyridin-2-yl)pyridin-2-amine (0.095 g, 0.285 mmol) from Example 9, CsF (0.118 g, 0.778 mmol), Pd(OAc)$_2$ (0.012 g, 0.052 mmol), catacxium A (0.037 g, 0.104 mmol), pivalic acid (0.045 mL, 0.389 mmol) and degassed dioxane (1.29 mL). The mixture was purged with N$_2$ for 5 min, then heated to 100° C. for 16 h. After cooling to rt, water was added, and the mixture was extracted with EtOAc 3 times. The combined organic phases were dried (MgSO$_4$), filtered, concentrated and purified by silica gel chromatography using a gradient solvent system of 0-100% EtOAc in DCM. The product-containing fractions were combined and concentrated to give methyl (R or S) 5-hydroxy-5-(5-(4-methyl-6-((4-(trifluoromethyl)pyridin-2-yl)amino)pyridin-2-yl)thiazol-2-yl)-5,6,7,8-tetrahydronaphthalene-1-carboxylate as a yellow solid. 92 mg, 66%. The other enantiomer was prepared in the same manner from the opposite enantiomer of methyl 5-hydroxy-5-(thiazol-2-yl)-5,6,7,8-tetrahydronaphthalene-1-carboxylate.

14A:

MS ESI calcd for $C_{27}H_{23}F_3N_4O_3S$ [M+H]$^+$ 541, found 541. $^1$H NMR (600 MHz, dmso) δ 10.17 (s, 1H), 8.62 (s, 1H), 8.46 (d, J=5.2, 1H), 8.19 (s, 1H), 7.65-7.55 (m, 1H), 7.43 (d, J=6.6, 1H), 7.33 (s, 1H), 7.21 (t, J=7.8, 1H), 7.18 (d, J=6.7, 1H), 7.08 (s, 1H), 6.57 (s, 1H), 3.79 (d, J=4.5, 3H), 3.07-2.89 (m, 2H), 2.31 (d, J=9.7, 1H), 2.28 (s, 1H), 2.06 (dd, J=29.6, 16.7, 1H), 1.95 (br s, 1H) ppm.

14B:

MS ESI calcd for $C_{27}H_{23}F_3N_4O_3S$ [M+H]$^+$ 541, found 541. $^1$H NMR (600 MHz, dmso) δ 10.17 (s, 1H), 8.62 (s, 1H), 8.46 (d, J=5.1, 1H), 8.19 (s, 1H), 7.64-7.55 (m, 1H), 7.43 (dd, J=7.9, 1.2, 1H), 7.33 (s, 1H), 7.19 (dt, J=14.4, 7.8, 2H), 7.08 (s, 1H), 6.57 (s, 1H), 3.79 (d, J=4.5 Ha, 3H), 3.09-2.89 (m, 2H), 2.36-2.25 (m, 1H), 2.13-2.04 (m, 1H), 1.90 (ddd, J=18.8, 17.2, 8.4, 1H) ppm.

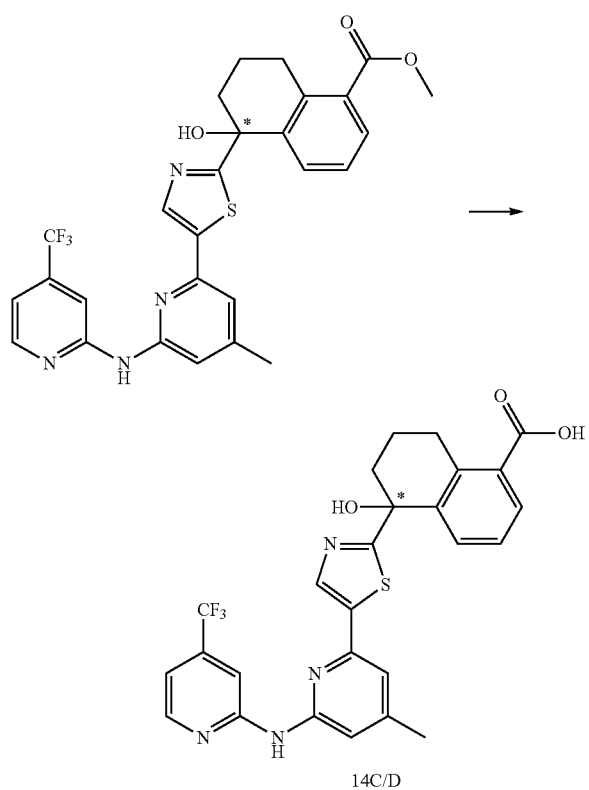

14C/D

Hydrolysis reactions on 14A and 14B were performed using methods analogous to those described in Example 7 to provide the carboxylic acids 14C and 14D.

14C/D (R or S)-5-hydroxy-5-(5-(4-methyl-6-((4-(trifluoromethyl)pyridin-2-yl)amino)pyridin-2-yl)thiazol-2-yl)-5,6,7,8-tetrahydronaphthalene-1-carboxylic acid. MS ESI calcd for $C_{26}H_{21}F_3N_4O_3S$ [M+H]$^+$ 527, found 527.

Example 15

(R or S)-3-hydroxy-3-(5-(4-methyl-6-((4-(trifluoromethyl)pyridin-2-yl)amino)pyridin-2-yl)thiazol-2-yl)-2,3-dihydro-1H-indene-5-carboxylic acid (15A and 15B)

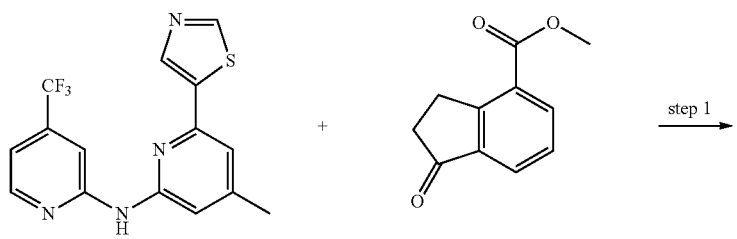

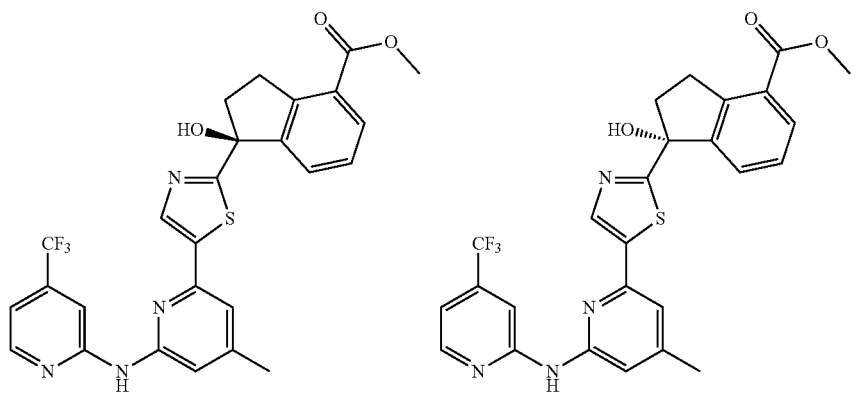

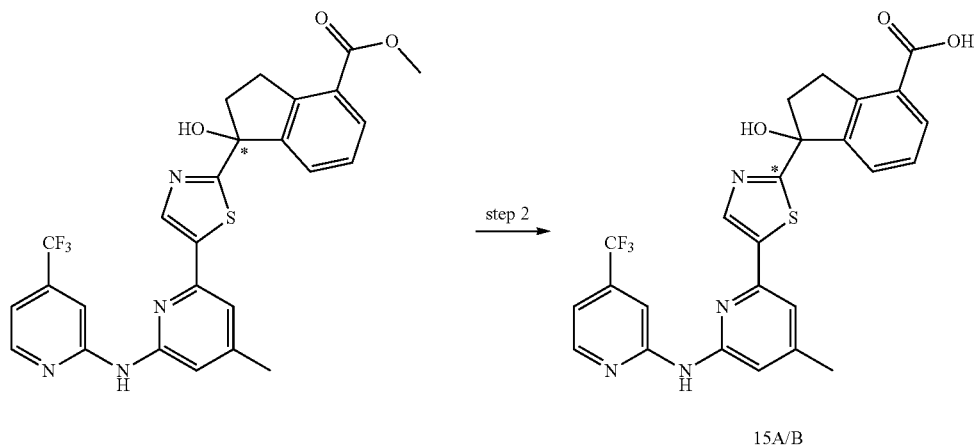

Step 1:

A solution of 4-methyl-6-(thiazol-5-yl)-N-(4-(trifluoromethyl)pyridin-2-yl)pyridin-2-amine (380 mg, 1.13 mmol) in 10 mL THF was cooled to −78° C., then LDA (2.5 mmol, freshly prepared) was added and the resulting mixture was stirred at the same temperature for 30 min. Then a solution of methyl 3-oxo-2,3-dihydro-1H-indene-5-carboxylate (1.13 mmol) in THF (3 mL) was added and the reaction was warmed to rt over a period of 4 h, then stirred for an additional 15 h at rt. The reaction was quenched by addition of saturated aqueous $NH_4Cl$ (10 mL) and the resulting mixture was extracted with EtOAc (2×20 mL). The combined organic phases were dried ($MgSO_4$), filtered and concentrated, and the residue was purified by silica gel chromatography to afford racemic methyl 3-hydroxy-3-(5-(4-methyl-6-((4-(trifluoromethyl)pyridin-2-yl)amino)pyridin-2-yl)thiazol-2-yl)-2,3-dihydro-1H-indene-5-carboxylate, which was resolved by chiral SFC (Column: Chiralcel OD-H 150×4.6 mm I.D., 5 um; Mobile phase: ethanol (0.05% DEA) in $CO_2$ from 5% to 40%; Flow rate: 2.35 mL/min; Wavelength: 220 nm) to give each enantiomer. MS ESI calcd for $C_{26}H_{21}F_3N_4O_3S$ $[M+H]^+$ 527, found 527.

Step 2:

To a solution of (R or S)-methyl 3-hydroxy-3-(5-(4-methyl-6-((4-(trifluoromethyl)pyridin-2-yl)amino)pyridin-2-yl)thiazol-2-yl)-2,3-dihydro-1H-indene-5-carboxylate (fast or slow eluting enantiomer, 105 mg, 0.2 mmol) in methanol (6 mL) was added sodium hydroxide (2 mL, 0.3 M, 0.6 mmol) and the mixture was heated to reflux for 1 h. The organic solvent was removed under reduced pressure and the residue was diluted with water (10 mL). The pH was adjusted to 6 with 1 M HCl, which resulted in formation of a white precipitate. The precipitate was collected by filtration, washed with water and dried to afford (R or S)-3-hydroxy-3-(5-(4-methyl-6-((4-(trifluoromethyl)pyridin-2-yl)amino)pyridin-2-yl)thiazol-2-yl)-2,3-dihydro-1H-indene-5-carboxylic acid (mass yield, percent) as a white powder.

15A (hydrolyzed from first eluting enantiomer): The resulting white powder was additionally purified by prep-TLC using a solvent system of 1:1 petroleum ether/EtOAc modified with 0.3% AcOH. The product-containing fractions were collected and concentrated under reduced pressure to give the acetate salt of (R or S)-3-hydroxy-3-(5-(4-methyl-6-((4-(trifluoromethyl)pyridin-2-yl)amino)pyridin-2-yl)thiazol-2-yl)-2,3-dihydro-1H-indene-5-carboxylic acid (22 mg, yield 21%) MS ESI calcd for $C_{25}H_{19}F_3N_4O_3S$ $[M+H]^+$ 513, found 513. $^1$H-NMR (MeOD, 400 MHz) δ 8.67 (s, 1H), 8.44 (d, J=4.7 Hz, 1H), 8.19 (s, 1H), 7.78 (d, J=6.5 Hz, 1H), 7.20-7.34 (m, 3H), 7.03-7.19 (m, 2H), 3.41-3.58 (m, 2H), 2.88-3.00 (m, 1H), 2.44-2.54 (m, 1H), 2.39 (s, 3H).

15B (hydrolyzed from second eluting enantiomer): (free base) (R or S)-3-hydroxy-3-(5-(4-methyl-6-((4-(trifluoromethyl)pyridin-2-yl)amino)pyridin-2-yl)thiazol-2-yl)-2,3-dihydro-1H-indene-5-carboxylic acid (86 mg, yield 84%) MS ESI calcd for $C_{25}H_{19}F_3N_4O_3S$ $[M+H]^+$ 513, found 513. $^1$H-NMR (400 MHz, MeOD) δ 8.60 (s, 1H), 8.30 (s, 1H), 8.06 (s, 1H), 7.95 (s, 1H), 7.45 (t, J=13.6 Hz, 2H), 7.35 (d, J=8 Hz, 2H), 7.02 (s, 1H), 3.55 (m, 2H), 2.93 (m, 1H), 2.45-2.55 (m, 1H), 2.42 (s, 3H).

The following compounds were prepared in an analogous manner using building blocks that are described above:

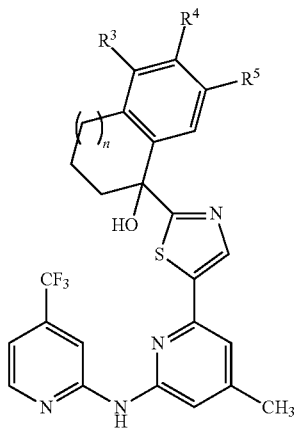

| Ex. | R³/R⁴/R⁵ | n | Name | [M + H]⁺ Calc'd | [M + H]⁺ Obs'd | Form |
|---|---|---|---|---|---|---|
| 15C | R³ = R⁴ = H<br>R⁵ = —CO₂H<br>Enantiomer 1 | 2 | (R or S)-9-hydroxy-9-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-2-carboxylic acid | 541 | 541 | Free Base |
| 15D | R³ = R⁴ = H<br>R⁵ = —CO₂H<br>Enantiomer 2 | 2 | (R or S)-9-hydroxy-9-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-2-carboxylic acid | 541 | 541 | Free Base |
| 15E | R³ = R⁵ = H<br>R⁴ = —CO₂H<br>Enantiomer 1 | 2 | (R or S)-5-hydroxy-5-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-2-carboxylic acid | 541 | 541 | Free Base |
| 15F | R³ = R⁵ = H<br>R⁴ = —CO₂H<br>Enantiomer 2 | 2 | (R or S)-5-hydroxy-5-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-2-carboxylic acid | 541 | 541 | Free Base |
| 15G | R³ = —CO₂H<br>R⁴ = R⁵ = H<br>Enantiomer 1 | 2 | (R or S)-5-hydroxy-5-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-1-carboxylic acid | 541 | 541 | Free Base |
| 15H | R³ = —CO₂H<br>R⁴ = R⁵ = H<br>Enantiomer 2 | 2 | (R or S)-5-hydroxy-5-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-1-carboxylic acid | 541 | 541 | Free Base |
| 15i | R³ = R⁴ = H<br>R⁵ = —CO₂H<br>Enantiomer 1 | 0 | (R or S)-3-hydroxy-3-[5-(4-methyl-6-{[4-(trifluoromethyl)pyridin-2-yl]amino}pyridin-2-yl)-1,3-thiazol-2-yl]-2,3-dihydro-1H-indene-5-carboxylic acid | 513 | 513 | Free Base |
| 15J | R³ = R⁴ = H<br>R⁵ = —CO₂H<br>Enantiomer 2 | 0 | (R or S)-3-hydroxy-3-[5-(4-methyl-6-{[4-(trifluoromethyl)pyridin-2-yl]amino}pyridin-2-yl)-1,3-thiazol-2-yl]-2,3-dihydro-1H-indene-5-carboxylic acid | 513 | 513 | Free Base |

Example 16

(R or S)-1-Hydroxy-1-(5-(4-methyl-6-((4-(trifluoromethyl)pyridin-2-yl)amino)pyridin-2-yl)thiazol-2-yl)-2,3-dihydro-1H-indene-5-carboxylic acid (16A and 16B)

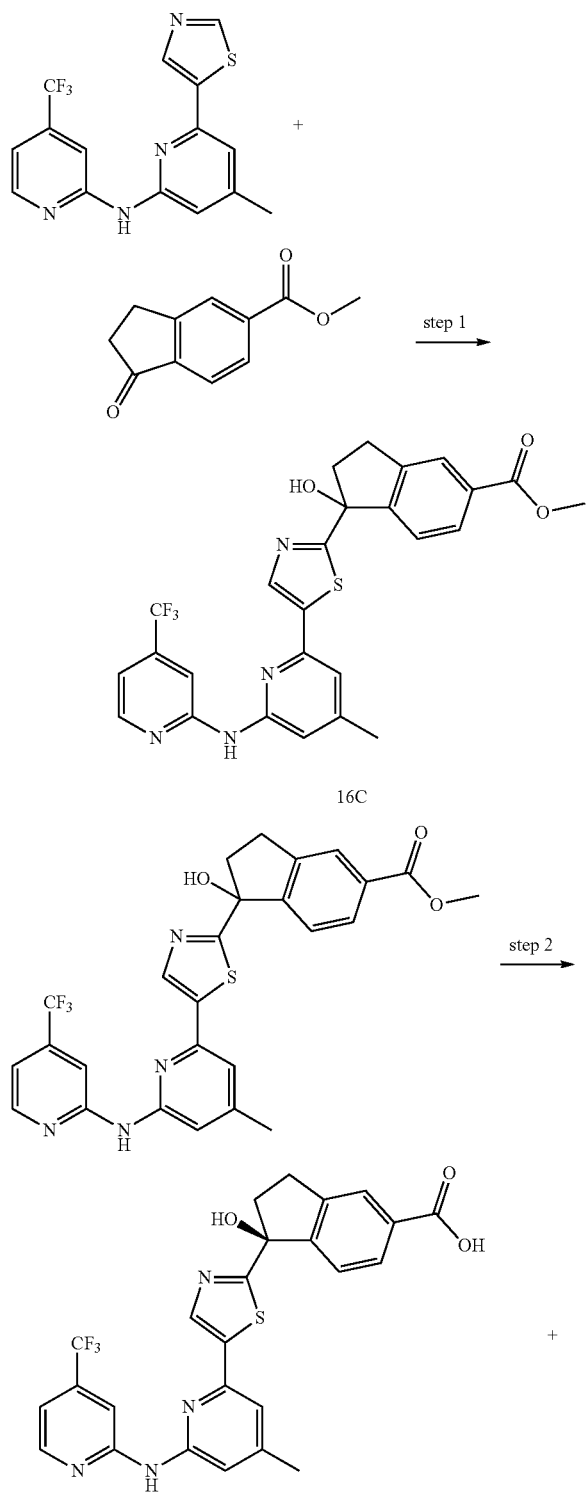

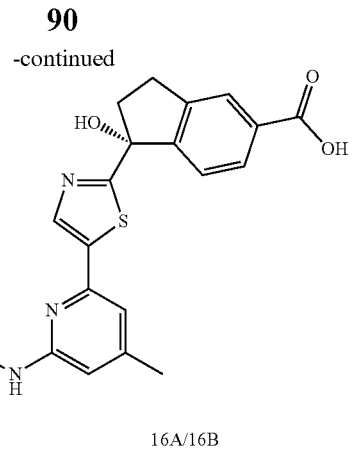

16A/16B

Step 1:

A solution of 4-methyl-6-(thiazol-5-yl)-N-(4-(trifluoromethyl)pyridin-2-yl)pyridin-2-amine (1.5 g, 4.46 mmol) in THF (35.7 mL) was cooled to −78° C. LDA (2M, 6.69 mL, 13.38 mmol) solution was slowly added, and the resulting mixture was stirred as at −78° C. for 30 minutes. In a separate dry flask, methyl 1-oxo-2,3-dihydro-1H-indene-5-carboxylate (1.06 g, 5.57 mmol) was dissolved in THF (5 mL), then this solution was added to the reaction mixture, which was then allowed to warm to rt over a period of 3 hrs, then stirred at rt for an additional 13 h. The reaction was quenched by addition of 2 mL MeOH and then loaded directly onto a silica gel chromatography column and purified with a gradient solvent system of 0-100% EtOAc/hexanes. The product-containing fractions were evaporated to give methyl 1-hydroxy-1-(5-(4-methyl-6-((4-(trifluoromethyl)pyridin-2-yl)amino)pyridin-2-yl)thiazol-2-yl)-2,3-dihydro-1H-indene-5-carboxylate 16C (912 mg, 39%) as a light yellow solid. MS ESI calcd for $C_{26}H_{21}F_3N_4O_3S$ [M+H]$^+$ 527, found 527.

Step 2:

To a solution of methyl 1-hydroxy-1-(5-(4-methyl-6-((4-(trifluoromethyl)pyridin-2-yl)amino)pyridin-2-yl)thiazol-2-yl)-2,3-dihydro-1H-indene-5-carboxylate (900 mg, 1.709 mmol) in THF (8.6 mL) was added aqueous potassium hydroxide (1.82 mL, 17.09 mmol) and the mixture was stirred at rt overnight. The reaction was diluted with MeOH (10 mL) and water (10 mL) and the organic solvents were removed under reduced pressure. The pH was adjusted to ~3 by addition of 1 M HCl, during which time the product precipitated. Collection of the precipitate by filtration furnished racemic 1-hydroxy-1-(5-(4-methyl-6-((4-(trifluoromethyl)pyridin-2-yl)amino)pyridin-2-yl)thiazol-2-yl)-2,3-dihydro-1H-indene-5-carboxylic acid (749 mg, 85%) as a white solid. The racemic mixture was resolved by chiral SFC using a Chiral Technologies IA-H 3.0×25 cm, 5 uM column and a solvent system of 50% MeOH/CO2, running at 70 mL/min. Under these conditions, the two enantiomers eluted at 5.5 min and 10.5 min.

16A:

Faster eluting enantiomer: (R or S)-1-hydroxy-1-(5-(4-methyl-6-((4-(trifluoromethyl)pyridin-2-yl)amino)pyridin-2-yl)thiazol-2-yl)-2,3-dihydro-1H-indene-5-carboxylic acid (185 mg, 25%), yellow solid. MS ESI calcd for $C_{25}H_{19}F_3N_4O_3S$ [M+H]$^+$ 513, found 513. $^1$H NMR (600 MHz, dmso) δ 12.85 (br s, 1H), 10.18 (s, 1H), 8.64 (s, 1H), 8.47 (d, J=5.1, 1H), 8.21 (s, 1H), 7.83 (s, 1H), 7.75 (d, J=8.0, 1H), 7.34 (s, 1H), 7.24 (d, J=8.0, 1H), 7.20 (d, J=5.0, 1H), 7.07 (s, 1H), 6.70 (s, 1H), 3.15-3.01 (m, 2H), 2.90-2.81 (m, 1H), 2.42-2.32 (m, 1H), 2.28 (s, 3H) ppm.

16B:

Slower eluting enantiomer: (R or S)-1-hydroxy-1-(5-(4-methyl-6-((4-(trifluoromethyl)pyridin-2-yl)amino)pyridin-2-yl)thiazol-2-yl)-2,3-dihydro-1H-indene-5-carboxylic acid (185 mg, 25%), yellow solid. MS ESI calcd for $C_{25}H_{19}F_3N_4O_3S$ [M+H]$^+$ 513, found 513. $^1$H NMR (600 MHz, dmso) δ 12.89 (br s, 1H), 10.18 (s, 1H), 8.64 (s, 1H), 8.47 (d, J=5.1, 1H), 8.21 (s, 1H), 7.83 (s, 1H), 7.75 (d, J=8.1, 1H), 7.34 (s, 1H), 7.24 (d, J=8.0, 1H), 7.20 (d, J=5.0, 1H), 7.07 (s, 1H), 6.70 (s, 1H), 3.14-3.03 (m, 2H), 2.90-2.80 (m, 1H), 2.43-2.33 (m, 1H), 2.28 (s, 3H) ppm.

Example 17

1-Bromo-5-hydroxy-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid (17)

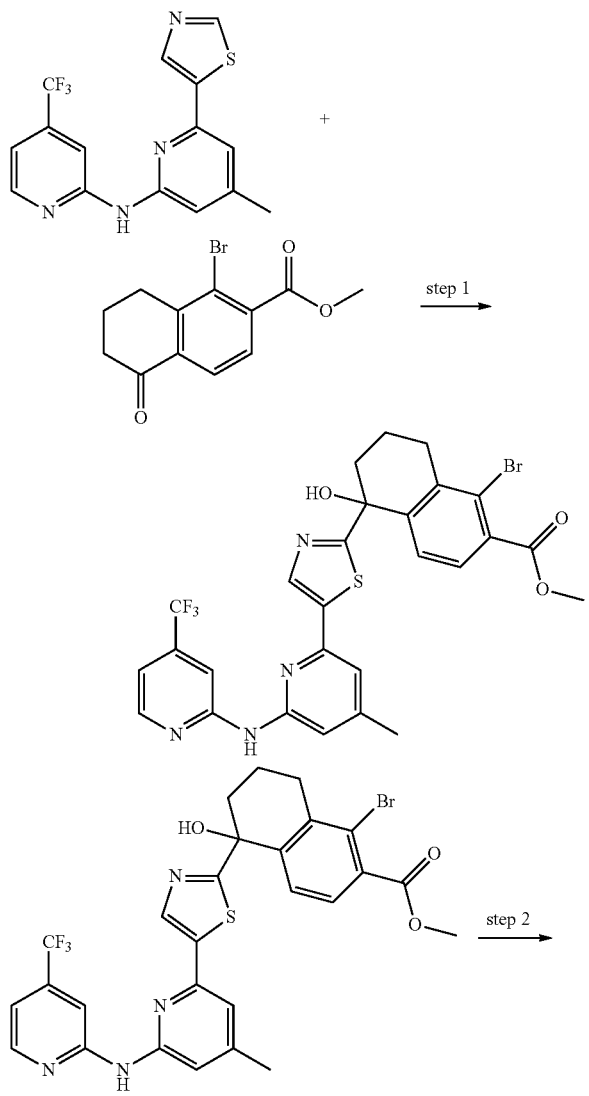

17A

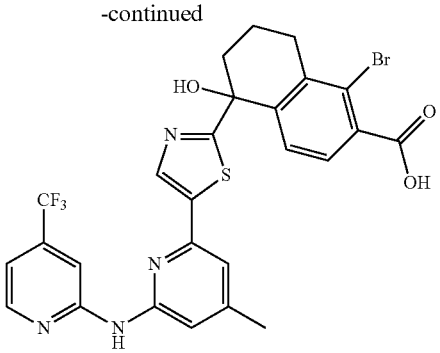

17

Step 1:

To an oven-dried flask was added 4-methyl-6-(thiazol-5-yl)-N-(4-(trifluoromethyl)pyridin-2-yl)pyridin-2-amine (300 mg, 0.892 mmol) and THF (7.1 mL) and the solution was cooled to −78° C. LDA (1.34 mL, 2.68 mmol) was slowly added, and the resulting mixture was stirred for 30 minutes at −78° C. In a separate oven-dried flask, methyl 1-bromo-5-oxo-5,6,7,8-tetrahydronaphthalene-2-carboxylate (316 mg, 1.12 mmol) was then dissolved in THF (5 mL), and this solution was added to the reaction mixture, which was then allowed to warm to rt. over a period of 3 hours. The reaction was then quenched with MeOH (5 mL) and concentrated. Purification by chromatography on silica gel furnished methyl 1-bromo-5-hydroxy-5-(5-(4-methyl-6-((4-(trifluoromethyl)pyridin-2-yl)amino)pyridin-2-yl)thiazol-2-yl)-5,6,7,8-tetrahydronaphthalene-2-carboxylate 17A (210 mg, 38%) as a light yellow solid. MS ESI calcd for $C_{27}H_{22}BrF_3N_4O_3S$ [M+H]$^+$ 619, found 619.

Step 2:

To a solution of methyl 1-bromo-5-hydroxy-5-(5-(4-methyl-6-((4-(trifluoromethyl)pyridin-2-yl)amino)pyridin-2-yl)thiazol-2-yl)-5,6,7,8-tetrahydronaphthalene-2-carboxylate (50 mg, 0.081 mmol) in THF (1.6 mL) was added aqueous potassium hydroxide (172 μl, 1.61 mmol), and the mixture was stirred for 16 h at rt, after which time the reaction mixture was diluted with MeOH (2 mL), filtered, and purified by reverse phase HPLC using a C18 column and a mixture of MeCN and water modified with 0.1% TFA. The product-containing fractions were partitioned between pH 4 buffer (20 mL) and EtOAc (20 mL) and the layers were separated. The aqueous phase was extracted with EtOAc (1×20 mL)), then the combined organic phases were washed with brine (20 mL), dried, and concentrated to yield 1-bromo-5-hydroxy-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid (25 mg, 52%) as a white solid. MS ESI calcd for $C_{26}H_{20}BrF_3N_4O_3S$ [M+H]$^+$ 605, found 605. $^1$H NMR (600 MHz, dmso) δ 10.17 (s, 1H), 8.62 (s, 1H), 8.46 (d, J=5.0, 1H), 8.20 (s, 1H), 7.35-7.29 (m, 3H), 7.19 (s, 1H), 7.08 (s, 1H), 6.68 (s, 1H), 2.79 (s, 3H), 2.32-2.2.24 (m, 4H), 2.06 (br s, 1H), 1.96 (br s, 2H) ppm.

Example 18

1-Cyano-5-hydroxy-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid, trifluoroacetate salt (18)

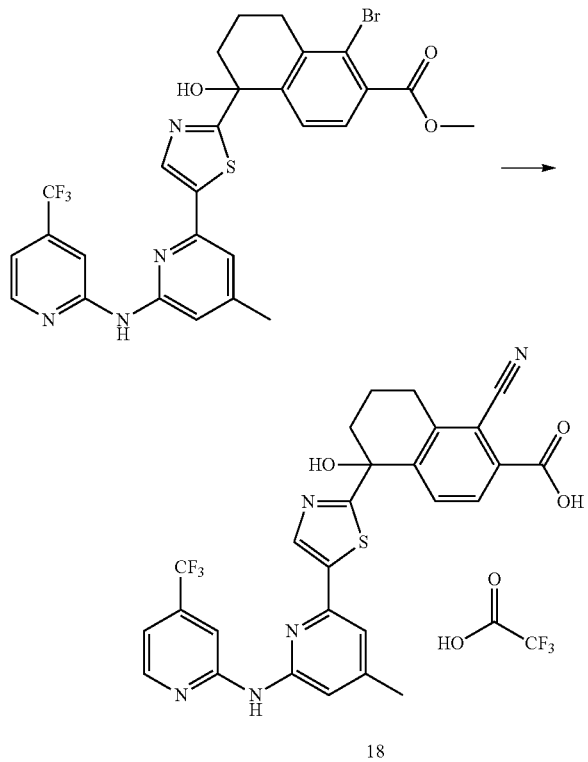

18

To a microwave vial charged allylpalladium chloride (1.48 mg, 4.04 µmol) and x-phos (2-Dicyclohexylphosphino-2',4',6'-triisopropylbiphenyl) (6.73 mg, 0.014 mmol) and DMA (807 µL). The vessel was vacuum-purged with argon 3 times, then heated 65° C. and stirred for 30 minutes. Methyl 1-bromo-5-hydroxy-5-(5-(4-methyl-6-((4-(trifluoromethyl)pyridin-2-yl)amino)pyridin-2-yl)thiazol-2-yl)-5,6,7,8-tetrahydronaphthalene-2-carboxylate (50 mg, 0.081 mmol) and Zinc(II) Cyanide (12.32 mg, 0.105 mmol) were then sequentially added. The vessel was vacuum-purged with argon 3 times, then heated to 100° C. for 16 h. The reaction was cooled to rt, then aqueous lithium hydroxide (404 µl, 0.404 mmol) was added. The resulting mixture was stirred at rt for 16 h, after which time TFA was added until pH was ~4, and the mixture was diluted with DMSO (1 mL) and MeCN (1 mL). The resulting mixture was filtered then purified by reverse phase HPLC using a C18 column and a solvent system of MeCN and water modified with 0.1% TFA. The product-containing fraction were concentrated to give the trifluoroacetate salt of 1-cyano-5-hydroxy-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid (29 mg, 54%) as a white solid. MS ESI calcd for $C_{27}H_{20}F_3N_5O_3S$ [M+H]$^+$ 552, found 552. $^1$H NMR (600 MHz, dmso) δ 10.18

(s, 1H), 8.61 (s, 1H), 8.46 (d, J=5.1, 1H), 8.23 (s, 1H), 7.84 (d, J=8.3, 1H), 7.65 (d, J=8.3, 1H), 7.35 (s, 1H), 7.18 (d, J=4.9, 1H), 7.06 (s, 1H), 2.99 (d, J=5.4, 2H), 2.38-2.25 (m, 3H), 2.18-2.06 (m, 1H), 1.99 (d, J=6.3, 2H). ppm.

Example 19

5-Hydroxy-1-methoxy-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid (19)

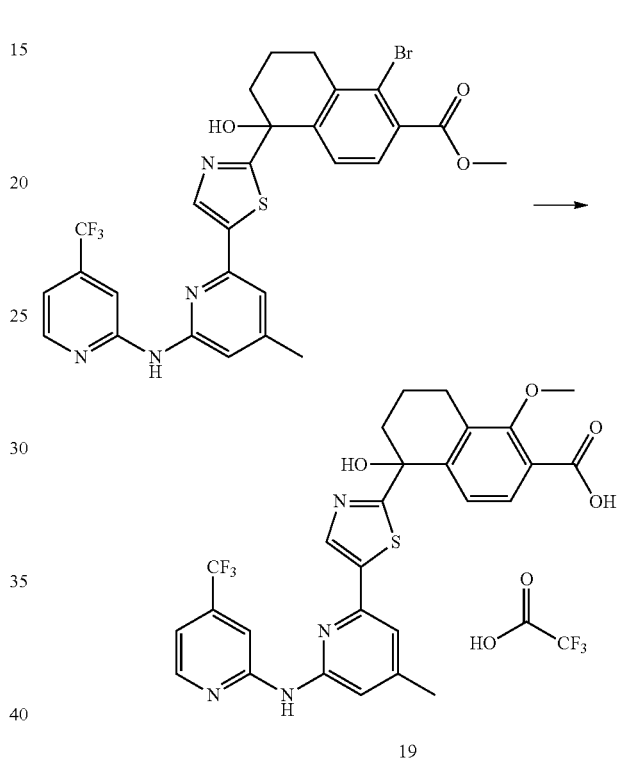

19

A microwave vial was charged with methyl 1-bromo-5-hydroxy-5-(5-(4-methyl-6-((4-(trifluoromethyl)pyridin-2-yl)amino)pyridin-2-yl)thiazol-2-yl)-5,6,7,8-tetrahydronaphthalene-2-carboxylate (50 mg, 0.081 mmol), MeOH (33 mL, 0.81 mmol), Pd$_2$(dba)$_3$ (7.39 mg, 8.07 µmol), BrettPhos (10.83 mg, 0.020 mmol), and Cs$_2$CO$_3$ (105 mg, 0.323 mmol). The vessel was vacuum-purged with argon 3 times, then degassed dioxane (807 µl) was added to the reaction mixture, which was sealed and heated at 100° C. overnight. The reaction was then cooled to rt and aqueous lithium hydroxide (404 µl, 0.404 mmol) was added. The resulting mixture was stirred at rt for 5 hours. The reaction was acidified with TFA, diluted with DMSO (1 mL) and MeCN (1 mL), filtered and purified by reverse phase HPLC using a C18 column with MeCN and water modified with 0.1% TFA as the solvent system. Concentration of the product-containing fraction yielded the trifluoroacetate salt of 5-hydroxy-1-methoxy-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid (54 mg, 22%) as a white solid. MS ESI calcd for $C_{27}H_{23}F_3N_4O_4S$ [M+H]$^+$ 557, found 557. $^1$H NMR (600 MHz, dmso) δ 10.16 (s, 1H), 8.61 (s, 1H), 8.46 (d, J=5.0, 1H), 8.20 (s, 1H), 7.42 (d, J=8.1, 1H), 7.33 (s, 1H), 7.18 (d, J=5.3, 1H), 7.07 (s, 1H), 7.03 (d, J=8.3, 1H), 3.72 (s, 3H), 2.86-2.78

(m, 1H), 2.76-2.68 (m, 1H), 2.34-2.30 (m, 1H), 2.28 (s, 3H), 2.10-2.04 (m, 1H), 2.01-1.83 (m, 2H) ppm.

Example 20

5-Hydroxy-5-(5-(4-methyl-6-((4-(trifluoromethyl) pyridin-2-yl)amino)pyridin-2-yl)thiazol-2-yl)-5,6,7, 8-tetrahydronaphthalene-2-carbonitrile (20B)

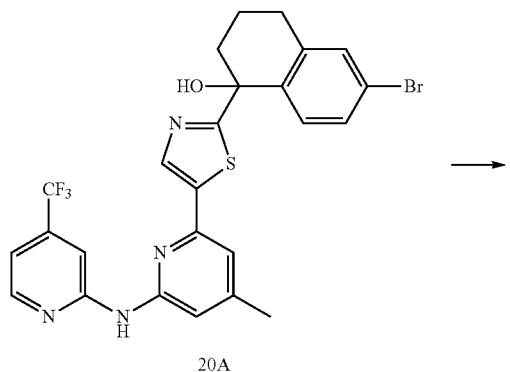

To a microwave vial was added 6-bromo-1-(5-(4-methyl-6-((4-(trifluoromethyl)pyridin-2-yl)amino)pyridin-2-yl) thiazol-2-yl)-1,2,3,4-tetrahydronaphthalen-1-ol 20A (650 mg, 1.158 mmol), zinc(II) cyanide (150 mg, 1.274 mmol), and tetrakis(triphenylphosphine)palladium (134 mg, 0.116 mmol). The vial was vacuum purged with argon 3 times, then degassed DMF (2316 μl) was added and the reaction was heated at 100° C. for 16 h. After cooling to rt, the reaction was diluted with MeOH (20 mL) and MeCN (20 mL), filtered through Celite®, and concentrated under reduced pressure. The resulting crude material was purified by silica gel chromatography using a gradient solvent system of 0-100% EtOAc/hexanes. Evaporation of the product-containing fractions yielded 5-hydroxy-5-(5-(4-methyl-6-((4-(trifluoromethyl)pyridin-2-yl)amino)pyridin-2-yl)thiazol-2-yl)-5,6,7,8-tetrahydronaphthalene-2-carbonitrile 20B (533 mg, 91%) as a light yellow solid. MS ESI calcd for $C_{26}H_{20}F_3N_5OS$ [M+H]$^+$ 507, found 507. $^1$H NMR (600 MHz, dmso) δ 10.18 (s, 1H), 8.62 (s, 1H), 8.46 (d, J=5.1, 1H), 8.22 (s, 1H), 7.62 (s, 1H), 7.53 (dd, J=8.2, 1.6, 1H), 7.38 (d, J=8.2, 1H), 7.34 (s, 1H), 7.19 (d, J=5.9, 1H), 7.06 (s, 1H), 6.70 (s, 1H), 2.83 (d, J=5.8, 2H), 2.38-2.29 (m, 1H), 2.28 (s, 3H), 2.15-2.05 (m, 1H), 2.01-1.80 (m, 2H) ppm.

Example 21

1-(5-(4-Methyl-6-((4-(trifluoromethyl)pyridin-2-yl) amino)pyridin-2-yl)thiazol-2-yl)-6-(2H-tetrazol-5-yl)-1,2,3,4-tetrahydronaphthalen-1-ol (21)

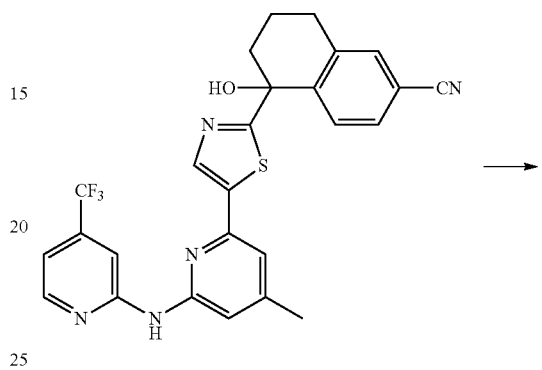

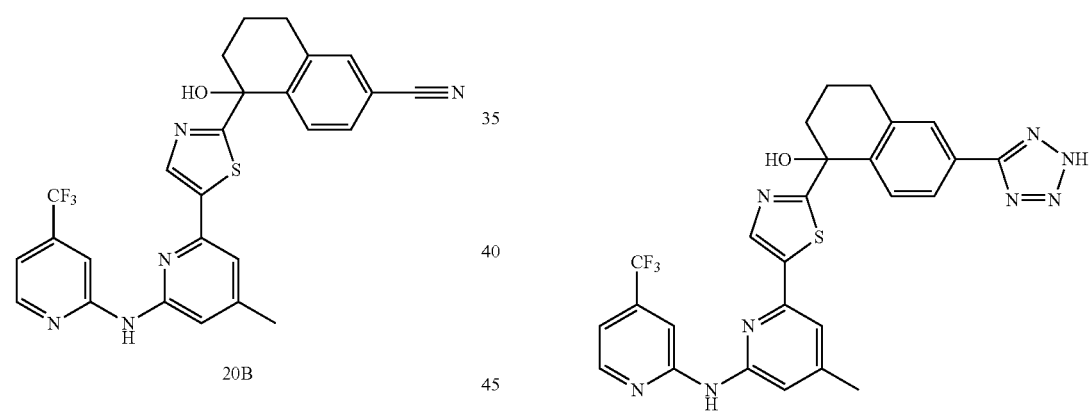

To a microwave vial was added 5-hydroxy-5-(5-(4-methyl-6-((4-(trifluoromethyl)pyridin-2-yl)amino)pyridin-2-yl) thiazol-2-yl)-5,6,7,8-tetrahydronaphthalene-2-carbonitrile (250 mg, 0.493 mmol), sodium azide (32.0 mg, 0.493 mmol), zinc bromide (111 mg, 0.493 mmol) and DMF (2463 μl). The tube was sealed and heated to 125° C. for 16 h. The reaction was cooled to rt and filtered, then purified by reverse phase HPLC using a C18 column with a solvent system containing MeCN and H$_2$O modified with 0.1% TFA. Product containing fractions were lyophilyzed to give 1-(5-(4-methyl-6-((4-(trifluoromethyl)pyridin-2-yl)amino)pyridin-2-yl)thiazol-2-yl)-6-(2H-tetrazol-5-yl)-1,2,3,4-tetrahydronaphthalen-1-ol (35 mg, 13%) as a white powder. MS ESI calcd for $C_{26}H_{21}F_3N_8OS$ [M+H]$^+$ 551, found 551. $^1$H NMR (600 MHz, dmso) δ 10.17 (s, 1H), 8.63 (s, 1H), 8.46 (d, J=4.8, 1H), 8.22 (s, 1H), 7.81 (s, 1H), 7.75 (d, J=7.8, 1H), 7.41 (d, J=8.1, 1H), 7.34 (s, 1H), 7.18 (d, J=4.0, 1H), 7.07 (s, 1H), 6.62 (s, 1H), 2.90 (d, J=4.3, 2H), 2.42-2.33 (m, 1H), 2.28 (s, 3H), 2.19-2.07 (m, 1H), 2.07-1.90 (m, 2H) ppm.

Example 22

(R)-5-hydroxy-5-(5-(4-methyl-6-((4-(trifluoromethyl)pyridin-2-yl)amino)pyridin-2-yl)thiazol-2-yl)-N-(methylsulfonyl)-5,6,7,8-tetrahydronaphthalene-2-carboxamide (22)

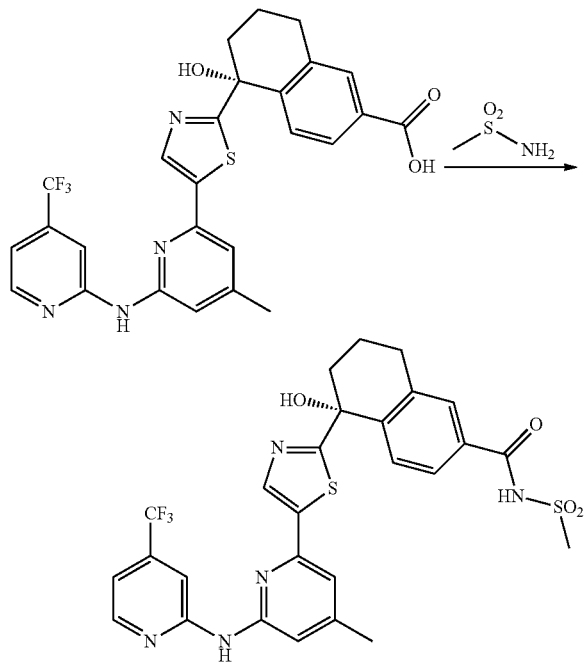

To a suspension of (R)-5-hydroxy-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid (20 mg, 0.038 mmol) and methanesulfonamide (4.34 mg, 0.046 mmol) in DCM (2 mL) at rt was added HATU (28.9 mg, 0.076 mmol) followed by Hunig's base (0.040 mL, 0.228 mmol) and the mixture was stirred at rt for 16 h. The solvent was removed under reduced pressure, and the residue was purified by reverse phase HPLC using a C18 column and a solvent system of MeCN and water modified with 0.1% TFA. The product-containing fractions were collected and lyophilized to give (R)-5-hydroxy-5-(5-(4-methyl-6-((4-(trifluoromethyl)pyridin-2-yl)amino)pyridin-2-yl)thiazol-2-yl)-N-(methylsulfonyl)-5,6,7,8-tetrahydronaphthalene-2-carboxamide (22.4 mg, 82%) as light yellow solid. MS ESI calcd for $C_{27}H_{24}F_3N_5O_4S_2$ [M+H]$^+$ 604, found 604. $^1$H NMR (500 MHz, dmso) δ 10.21 (s, 1H), 8.65 (s, 1H), 8.48 (s, 1H), 8.22 (d, J=3.9, 1H), 7.74 (s, 1H), 7.69-7.61 (m, 1H), 7.39-7.29 (m, 2H), 7.26-7.17 (m, 1H), 7.10 (s, 1H), 3.34 (s, 3H), 2.87 (m, 2H), 2.40-2.32 (m, 2H), 2.30 (s, 3H), 2.17-2.06 (m, 1H), 2.05-1.88 (m, 1H) ppm.

The following compounds were synthesized using similar methodology.

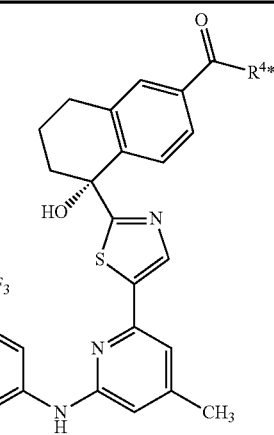

| Ex. | R4* | Name | [M + H]$^+$ Calc'd | [M + H]$^+$ Obs'd | Form(s) |
|---|---|---|---|---|---|
| 22A | ![sulfonyl cyclopropyl] | (R)-N-(cyclopropylsulfonyl)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide | 630 | 630 | TFA Salt |

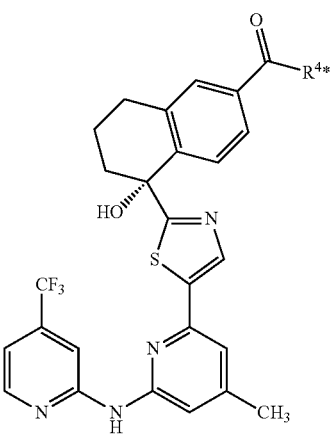

| Ex. | R⁴* | Name | [M + H]⁺ Calc'd | [M + H]⁺ Obs'd | Form(s) |
|---|---|---|---|---|---|
| 22B | | (R)-5-hydroxy-N-[(4-methylphenyl)sulfonyl]-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide | 680 | 680 | TFA Salt |
| 22C | | (R)-N-cyano-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide | 551 | 551 | TFA Salt |
| 22D | | (R)-5-hydroxy-5-[5-(4-methyl-6-{[4-(trifluoromethyl)pyridin-2-yl]amino}pyridin-2-yl)-1,3-thiazol-2-yl]-N-[(trifluoromethyl)sulfonyl]-5,6,7,8-tetrahydronaphthalene-2-carboxamide | 658 | 658 | TFA Salt |
| 22E | | (R)-5-hydroxy-5-[5-(4-methyl-6-{[4-(trifluoromethyl)pyridin-2-yl]amino}pyridin-2-yl)-1,3-thiazol-2-yl]-N-1H-tetrazol-5-yl-5,6,7,8-tetrahydronaphthalene-2-carboxamide | 594 | 594 | TFA Salt |
| 22F | | (R)-5-hydroxy-N-methoxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide | 556 | 556 | TFA Salt |

Example 23

(R)-diethyl (5-hydroxy-5-(5-(4-methyl-6-((4-(trifluoromethyl)pyridin-2-yl)amino)pyridin-2-yl)thiazol-2-yl)-5,6,7,8-tetrahydronaphthalen-2-yl)phosphonate (23)

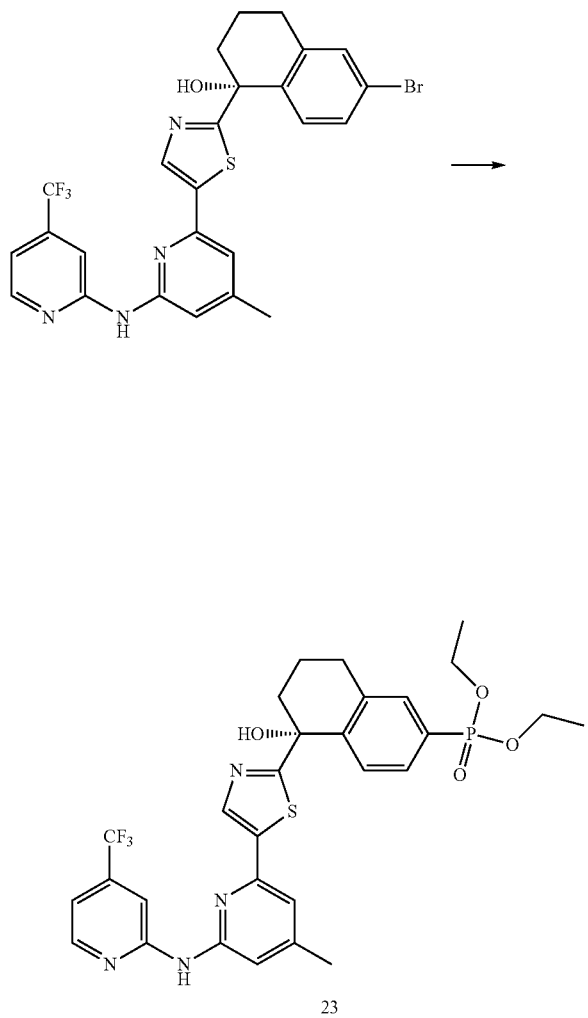

23

To a microwave vial was added (R)-6-bromo-1-(5-(4-methyl-6-((4-(trifluoromethyl)pyridin-2-yl)amino)pyridin-2-yl)thiazol-2-yl)-1,2,3,4-tetrahydronaphthalen-1-ol (20 mg, 0.036 mmol), tetrakis(triphenylphosphine)palladium (2.058 mg, 1.781 umol), EtOH (0.5 mL), diethyl phosphite (4.60 µl, 0.036 mmol), and Et$_3$N (7.45 µl, 0.053 mmol) The vial was sealed and heated to 100° C. under microwave radiation for 1 h. The reaction mixture was filtered and then purified by reverse phase HPLC using a C18 column and a solvent system of MeCN and water modified with 0.1% TFA. The product-containing fractions were collected and lyophilized to give the trifluoroacetate salt of (R)-diethyl (5-hydroxy-5-(5-(4-methyl-6-((4-(trifluoromethyl)pyridin-2-yl)amino)pyridin-2-yl)thiazol-2-yl)-5,6,7,8-tetrahydronaphthalen-2-yl)phosphonate (21.6 mg, 83%) as light yellow solid. MS ESI calcd for C$_{29}$H$_{30}$F$_3$N$_4$O$_4$PS [M+H]$^+$ 619, found 619. $^1$H NMR (500 MHz, dmso) δ 10.21 (s, 1H), 8.65 (s, 1H), 8.49 (d, J=5.1, 1H), 8.22 (s, 1H), 7.48 (d, J=14.0, 1H), 7.45-7.38 (m, 1H), 7.38- 7.31 (m, 2H), 7.21 (d, J=6.0, 1H), 7.11 (s, 1H), 4.06-3.88 (m, 4H), 2.90-2.86 (m, 2H), 2.35-2.32 (m, 1H), 2.31 (s, 3H), 2.14-2.10 (m, 1H), 2.02-1.98 (m, 2H), 1.20 (td, J=7.0, 1.7, 6H).

Example 24

(R)-(5-hydroxy-5-(5-(4-methyl-6-((4-(trifluoromethyl)pyridin-2-yl)amino)pyridin-2-yl)thiazol-2-yl)-5,6,7,8-tetrahydronaphthalen-2-yl)phosphonic acid (24)

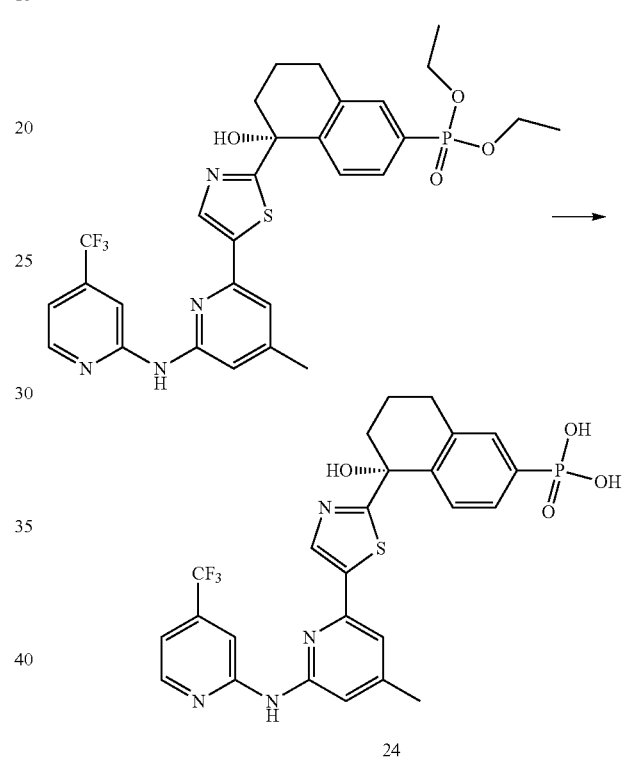

24

To a solution of the trifluoroacetate salt of (R)-diethyl (5-hydroxy-5-(5-(4-methyl-6-((4-(trifluoromethyl)pyridin-2-yl)amino)pyridin-2-yl)thiazol-2-yl)-5,6,7,8-tetrahydronaphthalen-2-yl)phosphonate (19 mg, 0.031 mmol) in EtOH (1 mL) was added 2 M aqueous NaOH (0.031 mL, 0.061 mmol) and the mixture was heated to 70° C. and stirred at that temperature for 1 h. Then the organic solvent was removed under reduced pressure and the residue was acidified with 2N HCl (31 ul), diluted with DMSO (1 mL) and filtered. The filtrate was purified by reverse phase HPLC using a C18 column and a solvent system of MeCN and water modified with 0.1% TFA. The product-containing fractions were collected and lyophilized to give the trifluoroacetate salt of (R)-(5-hydroxy-5-(5-(4-methyl-6-((4-(trifluoromethyl)pyridin-2-yl)amino)pyridin-2-yl)thiazol-2-yl)-5,6,7,8-tetrahydronaphthalen-2-yl)phosphonic acid (6.5 mg, 31%) as light yellow solid. MS ESI calcd for C$_{25}$H$_{22}$F$_3$N$_4$O$_4$PS [M+H]$^+$ 563, found 563. $^1$H NMR (500 MHz, dmso) δ 10.21 (s, 1H), 8.64 (s, 1H), 8.49 (d, J=5.2, 1H), 8.20 (s, 1H), 7.43 (d, J=13.3, 1H), 7.38 (dd, J=12.2, 8.0, 1H), 7.35 (s, 1H), 7.26 (dd, J=8.0, 3.8, 1H), 7.21 (d, J=5.1, 1H), 7.12 (s, 1H), 2.86-2.82

(m, 2H), 2.37-2.33 (m, 1H), 2.30 (s, 3H), 2.16-2.08 (m, 1H), 2.02-1.98 (m, 1H), 1.96-1.92 (m, 1H)

Example 25

(R)-(5-hydroxy-5-(5-(4-methyl-6-((4-(trifluoromethyl)pyridin-2-yl)amino)pyridin-2-yl)thiazol-2-yl)-5,6,7,8-tetrahydronaphthalen-2-yl)boronic acid (25)

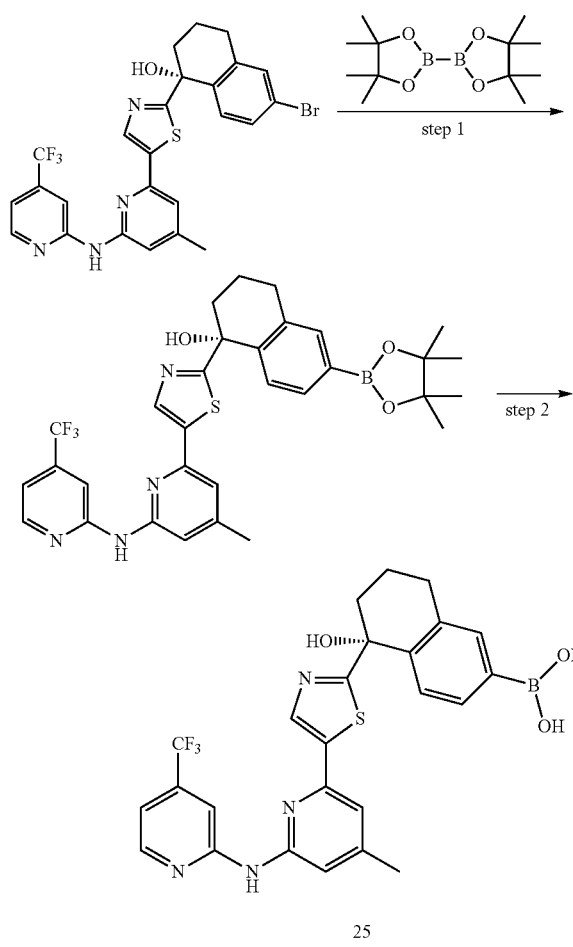

Step 1:
To a microwave vial added (R)-6-bromo-1-(5-(4-methyl-6-((4-(trifluoromethyl)pyridin-2-yl)amino)pyridin-2-yl)thiazol-2-yl)-1,2,3,4-tetrahydronaphthalen-1-ol (30 mg, 0.053 mmol) and bis(pinacolato)diboron (27.1 mg, 0.107 mmol), dioxane (1 mL), PdCl$_2$(dppf)-CH$_2$Cl$_2$ adduct (4.36 mg, 5.34 µmol) and potassium acetate (15.73 mg, 0.160 mmol). The vial was sealed and heated to 90° C. for 16 h. After cooling to rt, the mixture was filtered and the solvent was removed under reduced pressure. This material was used as such without further purification.

Step 2:
To this crude material was added EtOH (2 mL) and 2 M aqueous NaOH (1 mL, 2.000 mmol) and the reaction mixture was heated to 70° C. for 1 h. The solvent was removed under reduced pressure, and then the residue was made acidic with 2N HCl (1 mL) and then concentrated. The residue was dissolved in DMSO (2 mL) and filtered. The mixture was then purified by reverse phase HPLC using a C18 column and a solvent system of MeCN and water modified with 0.1% TFA. The product-containing fractions were collected and lyophilized to give the trifluoroacetate salt of (R)-(5-hydroxy-5-(5-(4-methyl-6-((4-(trifluoromethyl)pyridin-2-yl)amino)pyridin-2-yl)thiazol-2-yl)-5,6,7,8-tetrahydronaphthalen-2-yl)boronic acid (1.4 mg, 4.4%) as yellow solid. MS ESI calcd for C$_{25}$H$_{22}$BF$_3$N$_4$O$_3$S [M+H]$^+$ 527, found 527. $^1$H NMR (500 MHz, dmso) δ 10.24-10.17 (m, 1H), 8.67-8.60 (m, 1H), 8.55-8.45 (m, 1H), 8.25-8.17 (m, 1H), 7.58-7.50 (m, 1H), 7.51-7.45 (m, 1H), 7.38-7.31 (m, 1H), 7.24-7.19 (m, 1H), 7.18-7.13 (m, 1H), 7.13-7.08 (m, 1H), 2.85-2.75 (m, 2H), 2.40-2.32 (m, 1H), 2.30 (s, 3H), 2.13-2.04 (m, 1H), 2.02-1.87 (m, 2H).

Example 26

Methyl 5-fluoro-5-(5-(4-methyl-6-((4-(trifluoromethyl)pyridin-2-yl)amino)pyridin-2-yl)thiazol-2-yl)-5,6,7,8-tetrahydronaphthalene-2-carboxylate (26A)

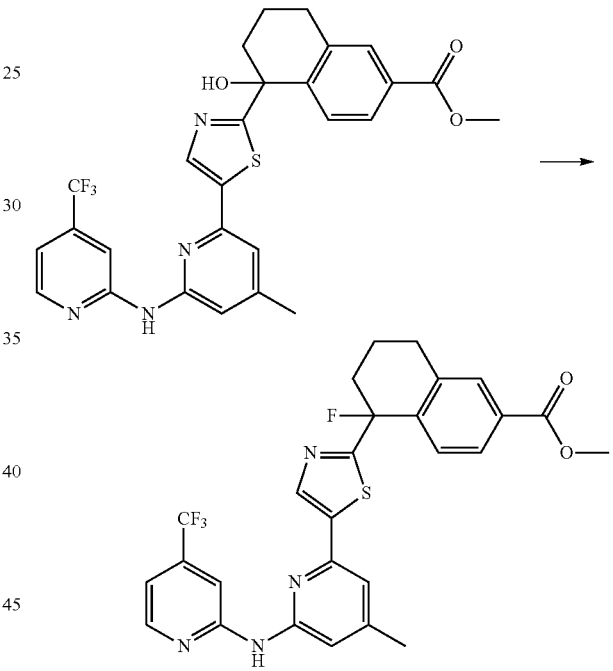

To a solution of methyl (S)-5-hydroxy-5-(5-(4-methyl-6-((4-(trifluoromethyl)pyridin-2-yl)amino)pyridin-2-yl)thiazol-2-yl)-5,6,7,8-tetrahydronaphthalene-2-carboxylate (250 mg, 0.462 mmol) in DCM (2.3 mL) was added deoxofluor (107 µl, 0.578 mmol), and the resulting mixture was sealed and stirred at rt for 2 hours. The reaction was quenched with saturated aqueous NaHCO$_3$ (20 mL), and the mixture was extracted with DCM (3×20 mL). The combined organic phases were dried (MgSO$_4$), filtered and concentrated. Purification by silica gel chromatography using a gradient solvent system of 0-100% EtOAc/hexanes furnished methyl 5-fluoro-5-(5-(4-methyl-6-((4-(trifluoromethyl)pyridin-2-yl)amino)pyridin-2-yl)thiazol-2-yl)-5,6,7,8-tetrahydronaphthalene-2-carboxylate (166 mg, 66%) as a white solid. MS ESI calcd for C$_{27}$H$_{22}$F$_4$N$_4$O$_2$S [M+H]$^+$ 543, found 543. $^1$H NMR (600 MHz, dmso) δ 10.22 (s, 1H), 8.59 (s, 1H), 8.46 (d, J=5.1, 1H), 8.41 (d, J=2.5, 1H), 7.83 (s, 1H), 7.77 (d, J=8.2, 1H), 7.43 (s, 1H), 7.40 (d, J=8.2, 1H), 7.18 (d, J=5.1, 1H), 7.07 (s, 1H), 3.82 (s, 3H), 3.03-2.93 (m, 1H), 2.92-2.86 (m, 1H), 2.65-2.52 (m, 1H), 2.43-2.33 (m, 1H), 2.29 (s, 3H), 1.98-1.79 (m, 2H) ppm.

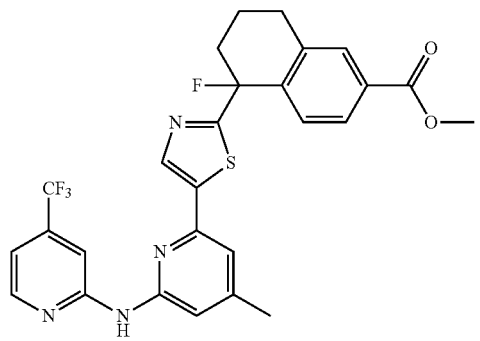

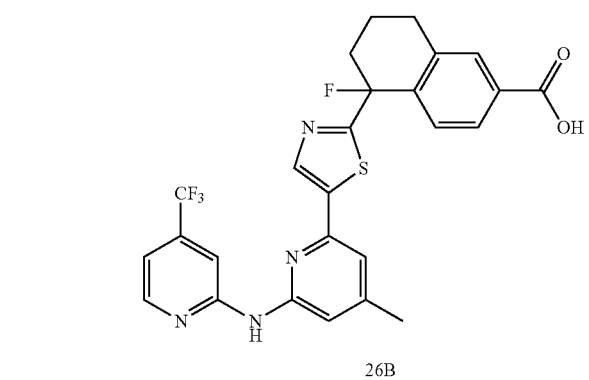

26B

Hydrolysis of 26 was performed using a method analogous to that described in Example 7.

26B:

5-fluoro-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid. MS ESI calcd for $C_{26}H_{20}F_4N_4O_2S$ [M+H]$^+$ 529, found 529.

Example 27

5-Amino-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid (27)

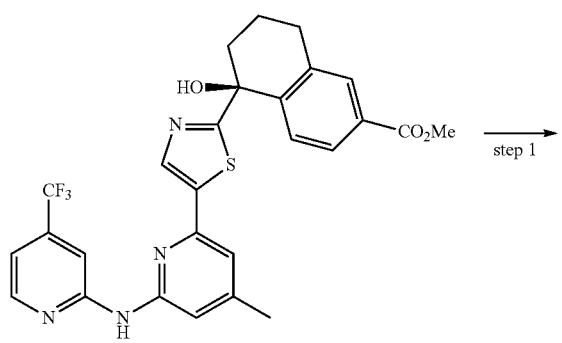

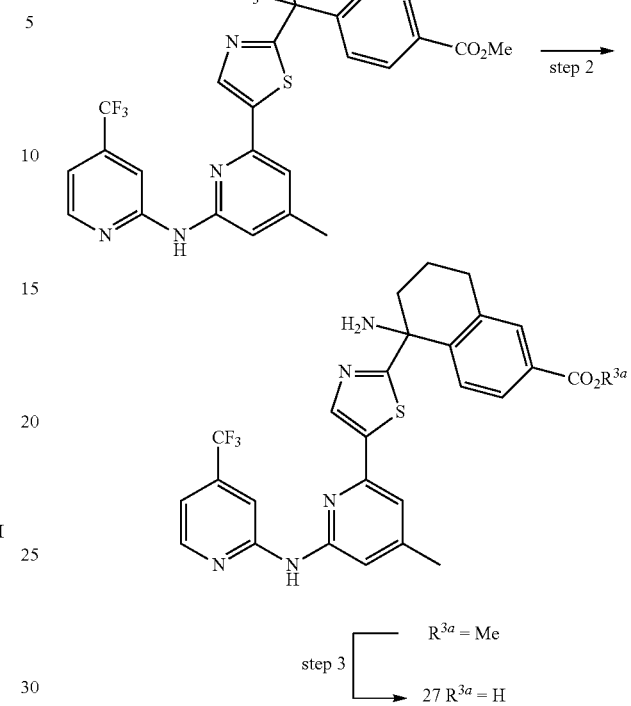

Step 1:

To a mixture of (S)-methyl 5-hydroxy-5-(5-(4-methyl-6-((4-(trifluoromethyl)pyridin-2-yl)amino)pyridin-2-yl)thiazol-2-yl)-5,6,7,8-tetrahydronaphthalene-2-carboxylate (100 mg, 0.185 mmol) and sodium azide (36.1 mg, 0.555 mmol) in DCM (2 mL) at rt was added TFA (0.016 mL, 0.203 mmol) dropwise and the mixture was stirred at rt for 16 h, after which time the reaction was heated to 40° C. for 5 days. The mixture was filtered, and the filtrate was concentrated under reduced pressure to give crude methyl 5-azido-5-(5-(4-methyl-6-((4-(trifluoromethyl)pyridin-2-yl)amino)pyridin-2-yl)thiazol-2-yl)-5,6,7,8-tetrahydronaphthalene-2-carboxylate as a brown oil, which was used as such for the following transformation. MS ESI calcd for $C_{27}H_{22}F_3N_7O_2S$ [M+H]$^+$ 566, found 566.

Step 2:

To a solution of crude methyl 5-azido-5-(5-(4-methyl-6-((4-(trifluoromethyl)pyridine-2-yl)amino)pyridine-2-yl)thiazol-2-yl)-5,6,7,8-tetrahydronaphthalene-2-carboxylate (50 mg, 0.088 mmol) in THF (1 mL) and water (0.1 mL) at rt was added trimethylphosphine (1M in THF) (0.133 mL, 0.133 mmol) and the mixture was stirred at rt for 16 h. The solvent was removed under reduced pressure, and the residue was redissolved in MeCN:DMSO (1:1) and filtered. The filtrate was purified by reverse phase chromatography using a C18 column with a mobile phase of MeCN and water modified with 0.1% TFA. The product containing fractions were combined and lyophilized to give the trifluoroacetate salt of methyl 5-amino-5-(5-(4-methyl-6-((4-(trifluoromethyl)pyridine-2-yl)amino)pyridine-2-yl)thiazol-2-yl)-5,6,7,8-tetrahydronaphthalene-2-carboxylate as white solid (30 mg, 63% yield). MS ESI calcd for $C_{27}H_{24}F_3N_5O_2S$ [M+H]$^+$ 540, found 540.

Step 3:

To a solution of the trifluoroacetate salt of methyl 5-amino-5-(5-(4-methyl-6-((4-(trifluoromethyl)pyridin-2-yl)amino)

pyridin-2-yl)thiazol-2-yl)-5,6,7,8-tetrahydronaphthalene-2-carboxylate (30 mg, 0.056 mmol) in EtOH (2 mL) was added sodium hydroxide (1 mL, 2.000 mmol) and the mixture was stirred at 70° C. for 45 min. The organic solvent was then removed under reduced pressure, and the residue was diluted with water, neutralized with 2N HCl (~1 mL), then extracted with EtOAc, dried over Na$_2$SO$_4$, and filtered. The filtrate was concentrated under reduced pressure, then purified by reverse phase chromatography using a C18 column with a mobile phase of MeCN and water modified with 0.1% TFA. The product containing fractions were combined and lyophilized the trifluoroacetate salt of 5-amino-5-(5-(4-methyl-6-((4-(trifluoromethyl)pyridine-2-yl)amino)pyridine-2-yl)thiazol-2-yl)-5,6,7,8-tetrahydronaphthalene-2-carboxylic acid as white solid (8.9 mg, 25% yield). MS ESI calcd for C$_{26}$H$_{22}$F$_3$N$_5$O$_2$S [M+H]$^+$ 526, found 526. $^1$H NMR (600 MHz, cd3od) δ 8.47 (s, 1H), 8.40 (s, 1H), 8.34 (d, J=5.2, 1H), 8.02 (s, 1H), 7.94 (d, J=8.2, 1H), 7.55 (d, J=8.3, 1H), 7.32 (s, 1H), 7.03 (d, J=5.1, 1H), 6.90 (s, 1H), 3.06 (t, J=6.1, 2H), 2.72-2.59 (m, 1H), 2.46-2.38 (m, 1H), 2.34 (s, 3H), 2.07 (s, 1H), 2.01-1.90 (m, 1H).

The enantiomers of 27 were prepared as described below.

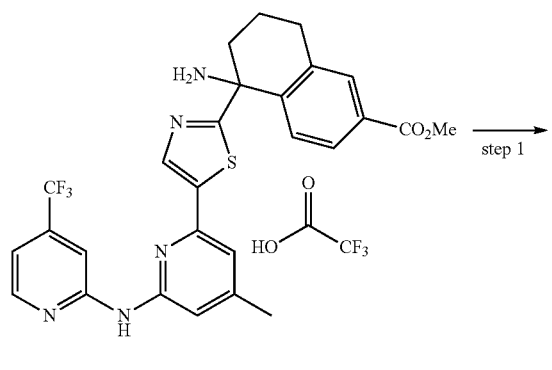

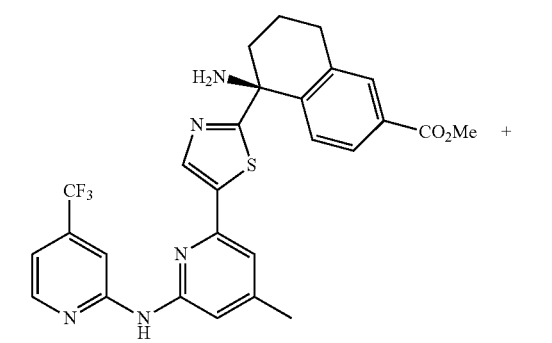

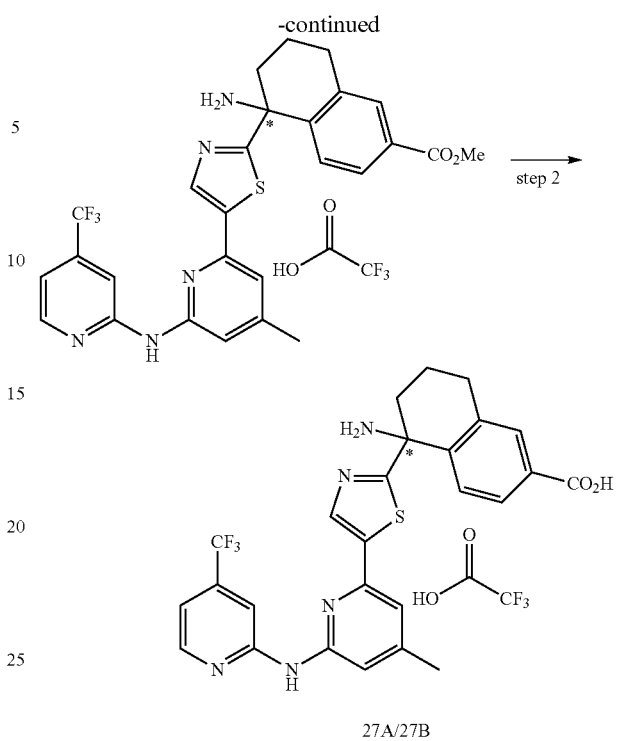

27A/27B

Step 1:

Racemic 5-amino-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid (250 mg, 0.46 mmol) was resolved by supercritical fluid chromatography using a Chiral Technology AS-H 2.1×25 cm, 5 mm column using a mobile phase of 25-75% MeOH modified with 0.25% Et$_2$NMe in CO$_2$. Under these conditions, the two enantiomers of methyl 5-amino-5-(5-(4-methyl-6-((4-(trifluoromethyl)pyridin-2-yl)amino)pyridin-2-yl)thiazol-2-yl)-5,6,7,8-tetrahydronaphthalene-2-carboxylate eluted at 6.06 min and 7.93 min. The product containing fractions were collected and concentrated under reduced pressure.

Faster eluting enantiomer: 92 mg, off-white solid. MS ESI calcd for C$_{27}$H$_{24}$F$_3$N$_5$O$_2$S [M+H]$^+$ 540, found 540.

Slower eluting enantiomer: 146 mg, off-white solid. MS ESI calcd for C$_{27}$H$_{24}$F$_3$N$_5$O$_2$S [M+H]$^+$ 540, found 540.

Step 2:

To a solution of (R or S)-methyl 5-amino-5-(5-(4-methyl-6-((4-(trifluoromethyl)pyridin-2-yl)amino)pyridin-2-yl)thiazol-2-yl)-5,6,7,8-tetrahydronaphthalene-2-carboxylate (faster eluting enantiomer) (80 mg, 0.15 mmol) in EtOH (2 mL) was added 1M aqueous NaOH (1 mL). The mixture was heated to 70° C. and stirred at that temperature for 1 h, at which time the organic solvent was removed under reduced pressure. The residue was made acidic by addition of HCl (1M, 1 mL), and the resulting mixture was concentrated under reduced pressure. The residue was purified by reverse phase HPLC using a C18 column and a solvent system of MeCN and water modified with 0.1% TFA. The product containing fractions were lyopholyzed to give the trifluoroacetate salt of (R or S)-5-amino-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid as a yellow solid 27A. MS ESI calcd for C$_{26}$H$_{22}$F$_3$N$_5$O$_2$S [M+H]$^+$ 526, found 526. $^1$H NMR (500 MHz, dmso) δ 10.21 (s, 1H), 9.33 (s, 2H), 8.65 (s, 1H), 8.44 (d, J=5.2, 1H), 8.37 (s, 1H), 7.91 (s, 1H), 7.87 (d, J=8.0, 1H), 7.67 (d, J=8.2, 1H), 7.49 (s, 1H), 7.14 (d, J=5.0, 1H), 7.05 (s, 1H), 2.98-2.94 (m, 2H), 2.54-2.50 (m, 2H), 2.31 (s, 3H), 2.01-1.97 (m, 1H), 1.75-1.63 (m, 1H).

27B:

A similar procedure was used to generate the enantiomer, the trifluoroacetate salt of (R or S)-5-amino-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid as a yellow solid. MS ESI calcd for $C_{26}H_{22}F_3N_5O_2S$ [M+H]$^+$ 526, found 526. $^1$H NMR (500 MHz, dmso) δ 10.21 (s, 1H), 9.33 (s, 2H), 8.65 (s, 1H), 8.44 (d, J=5.1, 1H), 8.37 (s, 1H), 7.91 (s, 1H), 7.87 (d, J=8.3, 1H), 7.67 (d, J=8.3, 1H), 7.49 (s, 1H), 7.14 (d, J=5.1, 1H), 7.05 (s, 1H), 2.98-2.94 (m, 2H), 2.54-2.50 (m, 2H), 2.31 (s, 3H), 2.04-1.95 (m, 1H), 1.75-1.62 (m, 1H).

Example 28

(Rac)-5-acetamido-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid, trifluoroacetate salt (28)

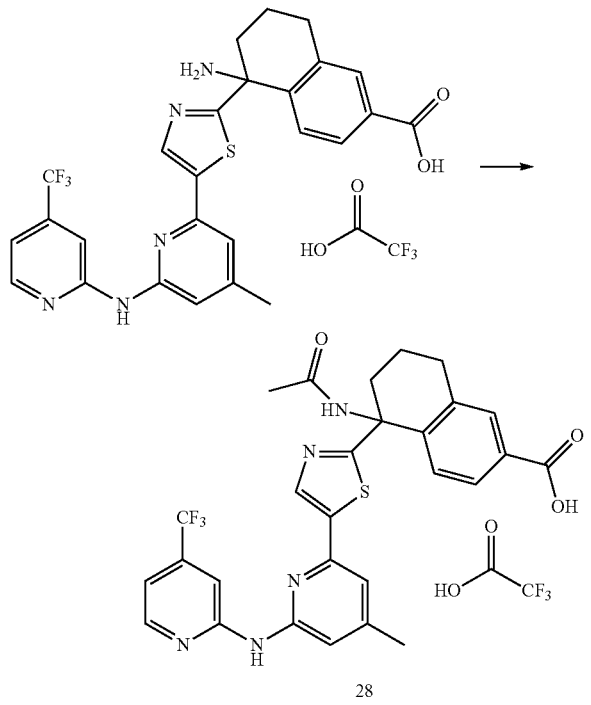

To a solution of 5-amino-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid, trifluoroacetate salt (5 mg, 0.0078 mmol) in DCM (1 mL) and Et$_3$N (2.2 mL) was added acetic anhydride (1.1 mL, 0.012 mmol) and the mixture was stirred at rt for 1 h, after which time the solvent was removed under reduced pressure. The resulting residue was dissolved in MeOH (1 mL) and treated with 2M NaOH (1 mL) at rt for 10 min, after which time the organic solvent was removed under reduced pressure. The resulting mixture was made acidic with 2N HCl, then purified by reverse phase HPLC using a C18 column and a mixture of MeCN and water modified with 0.1% TFA. The product-containing fractions were lyopholyzed to give the trifluoroacetate salt of 5-acetamido-5-(5-(4-methyl-6-((4-(trifluoromethyl)pyridin-2-yl)amino)pyridin-2-yl)thiazol-2-yl)-5,6,7,8-tetrahydronaphthalene-2-carboxylic acid (3.7 mg, 69%) as a yellow solid. MS ESI calcd for $C_{28}H_{24}F_3N_5O_3S$ [M+H]$^+$ 568, found 568. $^1$H NMR (600 MHz, CD$_3$OD) δ 8.37 (d, J=5.4, 1H), 8.31 (s, 1H), 8.26 (s, 1H), 7.86 (s, 1H), 7.79 (d, J=8.3, 1H), 7.51 (d, J=8.3, 1H), 7.35 (s, 1H), 7.18 (d, J=5.1, 1H), 6.95 (s, 1H), 3.09-2.89 (m, 3H), 2.49 (dd, J=11.7, 6.4, 1H), 2.38 (s, 3H), 2.01 (s, 3H), 1.96-1.92 (m, 1H), 1.89-1.79 (m, 1H) ppm.

Example 29

(R or S)-5-Hydroxy-5-(5-(6-((4-methoxypyridin-2-yl)amino)-4-methylpyridin-2-yl)thiazol-2-yl)-5,6,7,8-tetrahydronaphthalene-2-carboxylic acid (29A and 29B)

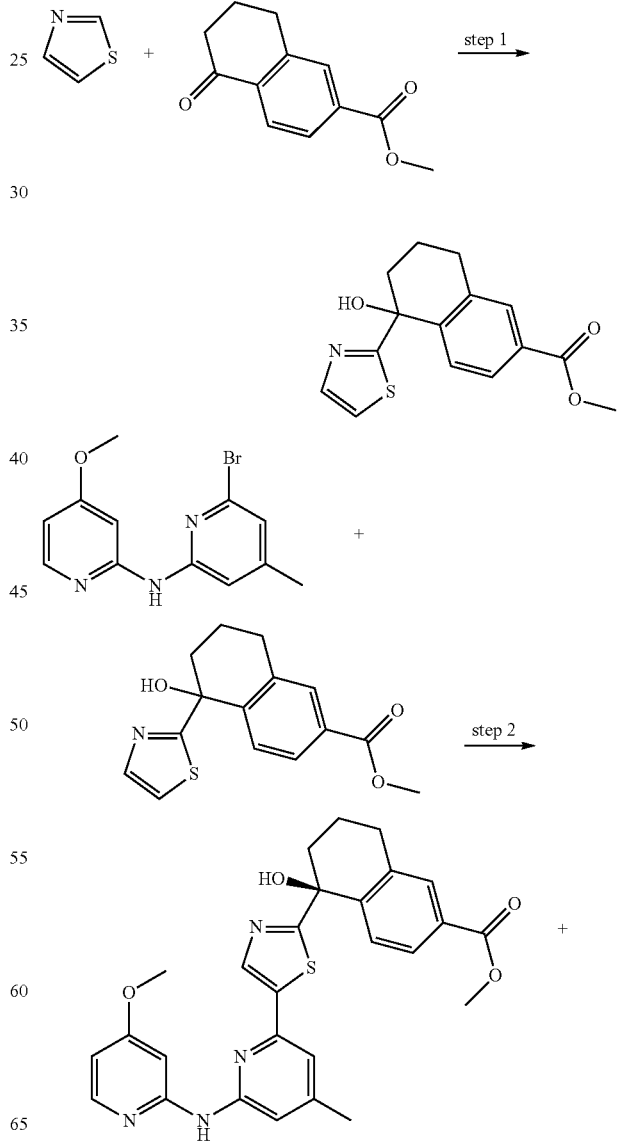

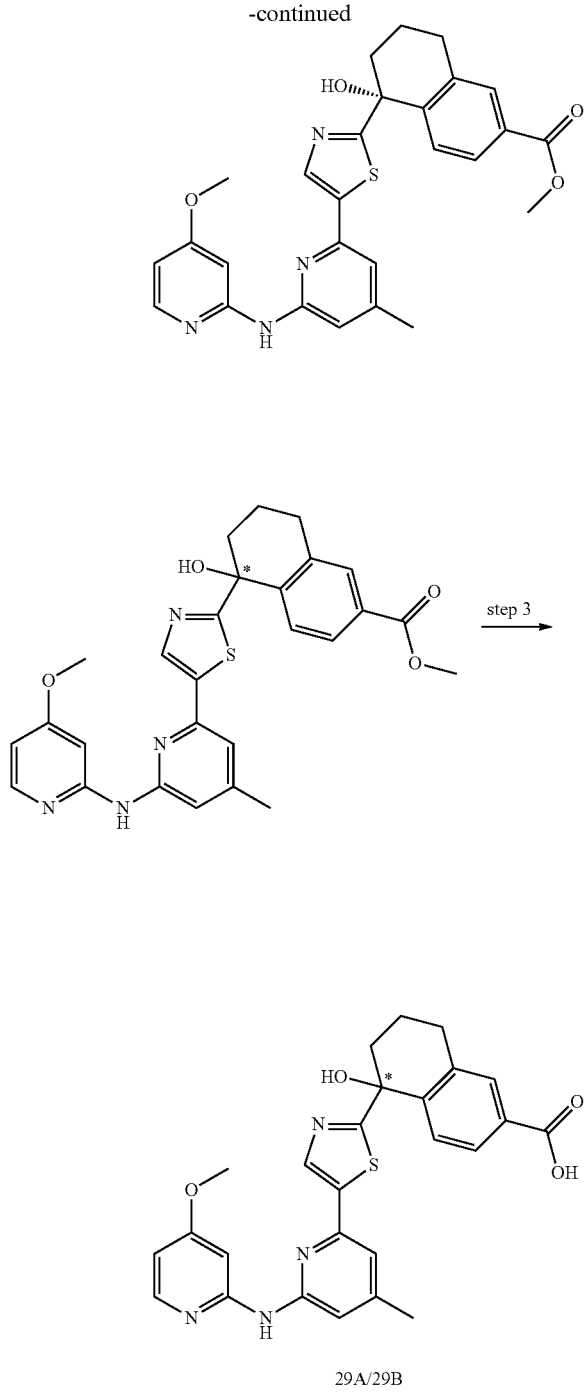

29A/29B

Step 1:

Thiazole (14.6 g, 172 mmol) was slowly added to a solution of isopropylmagnesium chloride lithium chloride complex (142 mL, 1.3 M in THF, 185 mmol) maintaining a temperature between 0 and 5° C. The resulting slurry was stirred for 1 h and then cooled to −20° C. A solution of methyl 5-oxo-5,6,7,8-tetrahydronapthalene (27.0 g, 132 mmol) in THF (50 mL) was added, maintaining the temperature between 0 to 5° C. and the solution stirred for 2 h. The resulting slurry was quenched with methanol (7.5 mL) and then water (50 mL) and isopropyl acetate (200 mL) were added, followed by 2 M aqueous HCl (50 mL). The resulting aqueous layer was extracted with isopropyl acetate (100 mL) and the organic layer was washed with saturated aqueous sodium bicarbonate (100 mL) and brine (100 mL). The resulting material was purified on silica gel to afford methyl 5-hydroxy-5-(1,3-thiazol-2-yl)-5,6,7,8-tetrahydronaphathlene-2-carboxylate (38.3 g, 57%). MS ESI calcd for $C_{15}H_{15}NO_3S$ [M+H]+ 290. found 290.

Step 2:

To a solution of Pd(OAc)$_2$ (45 mg, 0.2 mmol) in 1,4-dioxane (20 mL) was added butyldi-1-adamantylphosphine (143 mg, 0.4 mmol) and the mixture was stirred at under nitrogen for 10 minutes, during which time a yellow slurry developed. Then 6-bromo-N-(4-methoxypyridin-2-yl)-4-methylpyridin-2-amine (410 mg, 1.4 mmol), methyl 5-hydroxy-5-(thiazol-2-yl)-5,6,7,8-tetrahydronaphthalene-2-carboxylate (289 mg, 1 mmol), CsF (456 mg, 3 mmol), pivalic acid (153 mg, 1.5 mmol) and 1,4-dioxane (10 mL) were added. The reaction mixture was vacuum-purged with N$_2$ and then heated to reflux under N$_2$ for 20 hours. After cooling to rt, the reaction was filtered through Celite®, and the organic layer was washed with water and brine, dried over Na$_2$SO$_4$ and concentrated under reduced pressure. The residue was purified by silica gel chromatography using a solvent system of 2:1 petroleum ether/EtOAc to afford racemic methyl 5-hydroxy-5-(5-(6-((4-methoxypyridin-2-yl)amino)-4-methylpyridin-2-yl)thiazol-2-yl)-5,6,7,8-tetrahydronaphthalene-2-carboxylate (160 mg, 52% total), which was resolved by supercritical fluid chromatography using a Chiralpak AS-H 150*4.6 mm I.D., 5 um column and a mobile phase of 5 to 40% MeOH (0.05% diethylamine) in CO$_2$ with a flow rate 3 mL/min at a wavelength 220 nm to give two enantiomers. MS ESI calcd for $C_{27}H_{26}N4O_4S$ [M+H]+ 503. found 503.

Step 3:

To a solution of methyl (R or S)-5-hydroxy-5-(5-(6-((4-methoxypyridin-2-yl)amino)-4-methylpyridin-2-yl)thiazol-2-yl)-5,6,7,8-tetrahydronaphthalene-2-carboxylate (fast or slow enantiomer from step 2, 101 mg, 0.2 mmol) in MeOH (6 mL) was added a solution of sodium hydroxide (2 mL, 0.3 M, 0.6 mmol) and the mixture was heated to reflux for 1 hour. Methanol was removed under reduced pressure and the residue was diluted with 10 mL of water. The pH was adjusted to 6 with 1 M HCl, during which time a precipitate developed. The white precipitate was collected by filtration and washed with water and dried to afford (R or S)-5-hydroxy-5-(5-(6-((4-methoxypyridin-2-yl)amino)-4-methylpyridin-2-yl)thiazol-2-yl)-5,6,7,8-tetrahydronaphthalene-2-carboxylic acid.

29A (Faster moving enantiomer): MS ESI calcd for $C_{26}H_{24}N_4O_4S$ [M+H]$^+$ 489, found 489. $^1$H-NMR (400 MHz, MDSO) δ ppm 9.63 (s, 1H), 8.19 (s, 1H), 8.00 (d, J=6 Hz, 1H), 7.63-7.78 (m, 3H), 7.26 (d, J=8.4 Hz, 2H), 7.10 (s, 1H), 6.61 (s, 1H), 6.48 (d, J=3.6 Hz, 1H), 3.87 (s, 3H), 2.85 (s, 2H), 2.25-2.32 (m, 4H), 2.06-2.11 (m, 1H), 1.92-1.97 (m, 2H).

29B (Slower moving enantiomer): MS ESI calcd for $C_{26}H_{24}N_4O_4S$ [M+H]$^+$ 489, found 489. $^1$H-NMR (400 MHz, MeOD) δ ppm 8.22 (d, J=7.2 Hz, 1H), 7.84 (s, 1H), 7.74 (d, J=7.6 Hz, 1H), 7.54, (s, 1H), 7.29 (d, J=8 Hz, 1H), 6.89-6.92 (m, 3H), 2.96-2.97 (m, 2H), 2.42-2.48 (m, 4H), 2.22-2.33 (m, 1H), 2.00-2.09 (m, 2H).

The following pair of enantiomers was also prepared using a similar method to that described above in Example 29.

TABLE 2

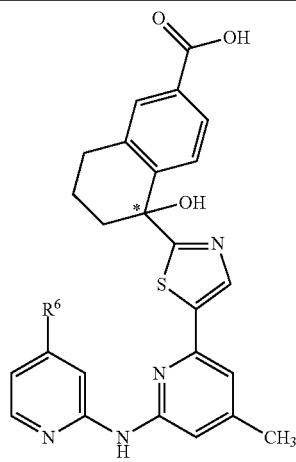

| Ex. | R⁶ | * | Name | [M + H]⁺ Calc'd | [M + H]⁺ Obs'd | Form |
|---|---|---|---|---|---|---|
| 29C | —OCH$_2$CH$_2$CH$_3$ | R or S | 5-hydroxy-5-(5-{4-methyl-6-[(4-propoxypyridin-2-yl)amino]pyridin-2-yl}-1,3-thiazol-2-yl)-5,6,7,8-tetrahydronaphthalene-2-carboxylic acid | 517 | 517 | Free base |
| 29D | —OCH$_2$CH$_2$CH$_3$ | R or S | 5-hydroxy-5-(5-{4-methyl-6-[(4-propoxypyridin-2-yl)amino]pyridin-2-yl}-1,3-thiazol-2-yl)-5,6,7,8-tetrahydronaphthalene-2-carboxylic acid | 517 | 517 | Free base |

Biological Assay
Homogeneous Time-Resolved Fluorescence (HTRF) Assay for the Recombinant Human Syk Enzyme A recombinant GST-hSyk fusion protein was used to measure potency of compounds to inhibit human Syk activity. The recombinant human GST-Syk (Cama Biosciences #08-176) (5 pM final concentration) was incubated with various concentrations of the inhibitor diluted in DMSO (0.1% final concentration) for 10 minutes at rt in 15 mM Tris-HCl (pH 7.5), 0.01% tween 20, 2 mM DTT in 384 well plate format. To initiate the reaction the biotinylated substrate peptide (250 nM final concentration) that contains the phosphorylation site for Syk was added with magnesium (5 mM final concentration) and ATP (25 μM final concentration). Final volume of the reaction was 10 μL. Phosphorylation of the peptide was allowed to proceed for 45' at rt. To quench the reaction and detect the phosphorylated product, 2 nM of a Europium-anti-phosphotyrosine antibody (Perkin Elmer #AD0161) and 70 nM SA-APC (Perkin-Elmer #CR130-100) were added together in 15 mM Tris pH 7.5, 40 mM EDTA, 0.01% tween 20. Final volume of the quenching solution was 10 μL. The resulting HTRF signal was measured after 30 minutes on a EnVision (Perkin-Elmer) reader using a time-resolved fluorescence protocol. IC$_{50}$ was determined following 10-dose titration (10 μM to 0.508 nM) and four parameter logistic curve fitting using an assay data analyzer. Compounds having IC$_{50}$ values below the lowest test concentration are indicated as "<0.50" for their IC$_{50}$ values.

TABLE A

| Example No. | IC$_{50}$ (nM) |
|---|---|
| 1 | <0.50 |
| 1A | <0.50 |
| 1B | 0.94 |

TABLE A-continued

| Example No. | IC$_{50}$ (nM) |
|---|---|
| 1C | <0.50 |
| 1D | <0.50 |
| 1E | <0.50 |
| 1F | <0.50 |
| 1G | 0.73 |
| 1H | <0.50 |
| 1i | 1.02 |
| 1J | <0.50 |
| 1K | <0.50 |
| 1L | unavailable |
| 1M | <0.50 |
| 1N | <0.50 |
| 1o | 0.67 |
| 1P | <0.50 |
| 1Q | 1.75 |
| 1R | <0.50 |
| 1S | <0.50 |
| 1T | <0.50 |
| 1U | <0.50 |
| 1V | <0.50 |
| 1W | 0.56 |
| 2 | <0.50 |
| 3 | 12.87 |
| 4 | <0.50 |
| 4A | <0.50 |
| 4B | 2.36 |
| 5 | 3.33 |
| 6 | 8.70 |
| 7 | <0.50 |
| 8 | 2.75 |
| 9 | 1.08 |
| 10 | 1.62 |
| 11 | <0.50 |
| 12A | <0.50 |
| 12B | 1.99 |
| 12C | 5.69 |
| 13A | 0.83 |

TABLE A-continued

| Example No. | IC$_{50}$ (nM) |
|---|---|
| 13B | <0.50 |
| 14A | 5.78 |
| 14B | 3.54 |
| 14C | <0.50 |
| 14D | <0.50 |
| 15A | 1.26 |
| 15B | <0.50 |
| 15C | 0.95 |
| 15D | 11.74 |
| 15E | <0.5 |
| 15F | 2.07 |
| 15G | <0.50 |
| 15H | <0.50 |
| 15i | 3.45 |
| 15J | <0.5 |
| 16A | 0.52 |
| 16B | 0.50 |
| 16C | 15.86 |
| 17 | <0.50 |
| 17A | 26.95 |
| 18 | <0.50 |
| 19 | <0.50 |
| 20A | 6.80 |
| 20B | 3.37 |
| 21 | 0.68 |
| 22 | <0.50 |
| 22A | <0.50 |
| 22B | 1.18 |
| 22C | 0.74 |
| 22D | 4.50 |
| 22E | <0.50 |
| 22F | 0.74 |
| 23 | 15.16 |
| 24 | <0.50 |
| 25 | 4.04 |
| 26A | 75.21 |
| 26B | 0.78 |
| 27 | 0.55 |
| 27A | <0.50 |
| 27B | 2.44 |
| 28 | 1.01 |
| 29A | 4.75 |
| 29B | 0.60 |
| 29C | <0.50 |
| 29D | 2.39 |

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:
1. A compound of the Formula (I)

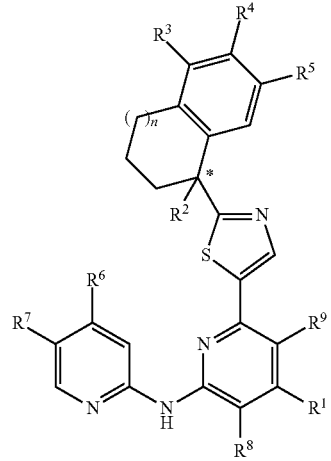

or a pharmaceutically acceptable salt thereof, wherein
$R^1$ is selected from the group consisting of:
(i) —$C_1$-$C_3$ alkyl;
(ii) fluoroalkyl;
(iii) —$CH_2OR^{1a}$,
wherein $R^{1a}$ is selected from the group consisting of H and $C_1$-$C_6$ alkyl;
(iv) —$N(R^{1b})_2$,
wherein each occurrence of $R^{1b}$ is selected from the group consisting of H and $C_1$-$C_3$ alkyl, or two $R^{1b}$ together with the N atom to which they are attached form a group of the formula

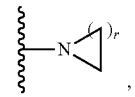

wherein r is 1, 2, 3, or 4;
(v) —O—($C_1$-$C_3$ alkyl);
(vi) —N(H)C(O)—($C_1$-$C_3$ alkyl);
(vii) halo;
(viii) H; and
(ix) morpholinyl;
$R^2$ is —OH, —O—($C_1$-$C_3$ alkyl), —$N(R^{2a})_2$, —$N(R^{2a})C(O)$—$R^{2b}$; or —F;
wherein each occurrence of $R^{2a}$ is selected from the group consisting of H and $C_1$-$C_3$ alkyl; and
$R^{2b}$ is $C_1$-$C_6$ alkyl;
$R^3$ is —$CO_2R^{3a}$, —$CH_2CO_2R^{3a}$, —$CH_2CH_2CO_2R^{3a}$, tetrazole, —$C(O)N(R^{3b})_2$, —$CH_2OH$, H, halo, —OH $C_1$-$C_6$ alkyl, —O—($C_1$-$C_3$ alkyl), —$N(R^{3b})_2$, —CN, —$C(O)N(H)S(O)_2R^{3c}$, —$C(O)$—$N(H)(R^{3d})$, —$C(O)N(H)C(O)R^{3a}$, —$P(O)(OR^{3b})_2$, or —$B(OH)_2$;
wherein $R^{3a}$ is selected from the group consisting of H and $C_1$-$C_6$ alkyl;
wherein each $R^{3b}$ is independently selected from the group consisting of H and $C_1$-$C_3$ alkyl;
wherein $R^{3c}$ is selected from the group consisting of $C_1$-$C_3$ alkyl, $C_1$-$C_3$ fluoroalkyl, $C_3$-$C_6$ cycloalkyl, and phenyl, wherein said phenyl is unsubstituted or substituted with one or two $C_1$-$C_3$ alkyl;

wherein $R^{3d}$ is selected from the group consisting of —CN, —O—($C_1$-$C_3$ alkyl), and tetrazole;

$R^4$ is —$CO_2R^{4a}$, —$CH_2CO_2R^{4a}$, —$CH_2CH_2CO_2R^{4a}$, tetrazole, —C(O)N($R^{4b}$)$_2$, —$CH_2OH$, H, halo, —OH, $C_1$-$C_6$ alkyl, —O—($C_1$-$C_3$ alkyl), —N($R^{4b}$)$_2$, —CN, —C(O)N(H)S(O)$_2R^{4c}$, —C(O)—N(H)($R^{4d}$), —C(O)N(H)C(O)$R^{4a}$, —P(O)(O$R^{4b}$)$_2$, or —B(OH)$_2$;

wherein $R^{4a}$ is selected from the group consisting of H and $C_1$-$C_6$ alkyl;

wherein each $R^{4b}$ is independently selected from the group consisting of H and $C_1$-$C_3$ alkyl;

wherein $R^{4c}$ is selected from the group consisting of $C_1$-$C_3$ alkyl, $C_1$-$C_3$ fluoroalkyl, $C_3$-$C_6$ cycloalkyl, and phenyl, wherein said phenyl is unsubstituted or substituted with one or two $C_1$-$C_3$ alkyl;

wherein $R^{4d}$ is selected from the group consisting of —CN, —O—($C_1$-$C_3$ alkyl), and tetrazole;

$R^5$ is —$CO_2R^{5a}$, —$CH_2CO_2R^{5a}$, —$CH_2CH_2CO_2R^{5a}$, tetrazole, —C(O)N($R^{5b}$)$_2$, —$CH_2OH$, H, halo, —OH, $C_1$-$C_6$ alkyl, —O—($C_1$-$C_3$ alkyl), —N($R^{5b}$)$_2$, —CN, —C(O)N(H)S(O)$_2R^{5c}$, —C(O)—N(H)($R^{5d}$), —C(O)N(H)C(O)$R^{5a}$, —P(O)(O$R^{5b}$)$_2$, or —B(OH)$_2$;

wherein $R^{5a}$ is selected from the group consisting of H and $C_1$-$C_6$ alkyl;

wherein each $R^{5b}$ is independently selected from the group consisting of H and $C_1$-$C_3$ alkyl;

wherein $R^{5c}$ is selected from the group consisting of $C_1$-$C_3$ alkyl, $C_1$-$C_3$ fluoroalkyl, $C_3$-$C_6$ cycloalkyl, and phenyl, wherein said phenyl is unsubstituted or substituted with one or two $C_1$-$C_3$ alkyl;

wherein $R^{5d}$ is selected from the group consisting of —CN, —O—($C_1$-$C_3$ alkyl), and tetrazole;

$R^6$ is selected from the group consisting of:
(i) $C_1$-$C_6$ alkyl;
(ii) $C_1$-$C_3$ fluoroalkyl;
(iii) —O—($C_1$-$C_6$ alkyl);
(iv) —O—($C_1$-$C_3$ fluoroalkyl);
(v) —$R^{6a}$, wherein $R^{6a}$ is selected from the group consisting of:
 (a) $C_3$-$C_6$ cycloalkyl;
 (b) a group of the formula

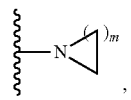

wherein m is 1, 2, 3, or 4;
 (c) a group of the formula

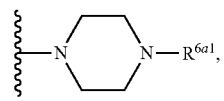

where $R^{6a1}$ is H, $C_1$-$C_3$ alkyl, or —$CH_2CH_2NH_2$; and
 (d) a 5- to 6-membered heteroaryl containing 1 to 3 heteroatoms selected from the group consisting of N, O, and S;
wherein $R^{6a}$ is unsubstituted or substituted with 1 to 3 $R^{6a2}$ moieties selected from the group consisting of halo and $C_1$-$C_3$ alkyl;

(vi) —O—$R^{6b}$,
 wherein $R^{6b}$ is selected from the group consisting of:
 (a) $C_3$-$C_6$ cycloalkyl; and
 (b) a group of the formula

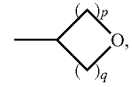

wherein p is 0, 1, or 2, and q is 1, 2, or 3;
 wherein $R^{6b}$ is unsubstituted or substituted with 1 to 2 $R^{6b1}$ moieties selected from the group consisting of fluoro and $C_1$-$C_3$ alkyl;
(vii) —N($R^{6c}$)$_2$, wherein each occurrence of $R^{6c}$ is selected from the group consisting of H and $C_1$-$C_3$ alkyl;
(viii) —N(H)C(O)—($C_1$-$C_3$ alkyl);
(ix) —N(H)C(O)O—($C_1$-$C_3$ alkyl);
(x) —NHC(O)—N($R^{6d}$)$_2$, wherein each $R^{6d}$ is H or $C_1$-$C_3$ alkyl;
(xi) halo; and
(xii) H;

$R^7$ is H or halo;
$R^8$ is H or halo;
$R^9$ is H or halo; and
n is 0, 1, or 2.

2. The compound of claim 1 or a pharmaceutically acceptable salt thereof, wherein:
$R^2$ is —OH, —O—($C_1$-$C_3$ alkyl), or —N($R^{2a}$)$_2$;
$R^3$ is —$CO_2R^{3a}$, —$CH_2CO_2R^{3a}$, —$CH_2CH_2CO_2R^{3a}$, tetrazole, —C(O)N($R^{3b}$)$_2$, —$CH_2OH$, H, halo, $C_1$-$C_6$ alkyl, —O—($C_1$-$C_3$ alkyl), or —N($R^{3b}$)$_2$;
$R^4$ is —$CO_2R^{4a}$, —$CH_2CO_2R^{4a}$, —$CH_2CH_2CO_2R^{4a}$, tetrazole, —C(O)N($R^{4b}$)$_2$, —$CH_2OH$, H, halo, $C_1$-$C_6$ alkyl, —O—($C_1$-$C_3$ alkyl), or —N($R^{4b}$)$_2$;
$R^5$ is —$CO_2R^{5a}$, —$CH_2CO_2R^{5a}$, —$CH_2CH_2CO_2R^{5a}$, tetrazole, —C(O)N($R^{5b}$)$_2$, —$CH_2OH$, H, halo, $C_1$-$C_6$ alkyl, —O—($C_1$-$C_3$ alkyl), and —N($R^{5b}$)$_2$;
$R^6$ is selected from the group consisting of:
(i) $C_1$-$C_6$ alkyl;
(ii) $C_1$-$C_3$ fluoroalkyl;
(iii) —O—($C_1$-$C_6$ alkyl);
(iv) —O—($C_1$-$C_3$ fluoroalkyl);
(v) —$R^{6a}$, wherein $R^{6a}$ is selected from the group consisting of:
 (a) $C_3$-$C_6$ cycloalkyl;
 (b) a group of the formula

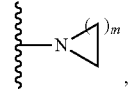

wherein m is 1, 2, 3, or 4;
 (c) a group of the formula

where $R^{6a1}$ is H, $C_1$-$C_3$ alkyl, or —$CH_2CH_2NH_2$; and (d) a 5- to 6-membered heteroaryl containing 1 to 3 heteroatoms selected from the group consisting of N, O, and S;
wherein $R^{6a}$ is unsubstituted or substituted with 1 to 3 $R^{6a2}$ moieties selected from the group consisting of halo and $C_1$-$C_3$ alkyl;

(vi) —O—$R^{6b}$,
wherein $R^{6b}$ is selected from the group consisting of:
(a) $C_3$-$C_6$ cycloalkyl; and
(b) a group of the formula

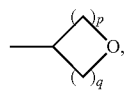

wherein p is 0, 1, or 2, and q is 1, 2, or 3;
wherein $R^{6b}$ is unsubstituted or substituted with 1 to 2 $R^{6b1}$ moieties selected from the group consisting of fluoro and $C_1$-$C_3$ alkyl;

(vii) —N($R^{6c}$)$_2$, wherein each occurrence of $R^{6c}$ is selected from the group consisting of H and $C_1$-$C_3$ alkyl;
(viii) —N(H)C(O)—($C_1$-$C_3$ alkyl);
(xi) halo; and
(xii) H.

3. The compound of claim 1 or a pharmaceutically acceptable salt thereof, wherein
when $R^3$ is —CO$_2$R$^{3a}$, —CH$_2$CO$_2$R$^{3a}$, —CH$_2$CH$_2$CO$_2$R$^{3a}$, tetrazole, —C(O)N(R$^{3b}$)$_2$, or —CH$_2$OH; then $R^4$ is H, halo, $C_1$-$C_6$ alkyl, —O—($C_1$-$C_3$ alkyl), or —N(R$^{4b}$)$_2$, and $R^5$ is H or halo; and
when $R^4$ is —CO$_2$R$^{4a}$, —CH$_2$CO$_2$R$^{4a}$, —CH$_2$CH$_2$CO$_2$R$^{4a}$, tetrazole, —C(O)N(R$^{4b}$)$_2$, or —CH$_2$OH; then $R^3$ is H, halo, $C_1$-$C_6$ alkyl, —O—($C_1$-$C_3$ alkyl), or —N(R$^{3b}$)$_2$, and $R^5$ is H or halo.

4. The compound of claim 1 or a pharmaceutically acceptable salt thereof, wherein $R^2$ is OH.

5. The compound of claim 1 or a pharmaceutically acceptable salt thereof, wherein n is 1.

6. A compound of the Formula IA or a pharmaceutically acceptable salt thereof

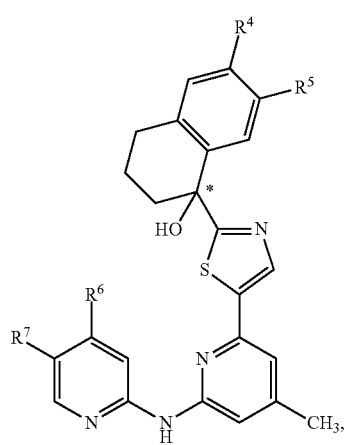

(IA)

wherein
$R^4$ is —CO$_2$R$^{4a}$, —C(O)NH$_2$, or —CH$_2$OH;
wherein $R^{4a}$ is selected from the group consisting of H and CH$_3$;
$R^5$ is H or fluoro;
$R^6$ is selected from the group consisting of:
(i) $C_1$-$C_4$ alkyl;
(ii) $C_1$-$C_3$ fluoroalkyl;
(iii) —O—($C_1$-$C_6$ alkyl);
(iv) —$R^{6a}$, wherein $R^{6a}$ is selected from the group consisting of:
(a) $C_3$-$C_6$ cycloalkyl,
(b) a group of the formula

where $R^{6a1}$ is H or —CH$_2$CH$_2$NH$_2$; and
(c) a 5-membered heteroaryl containing 1 to 3 heteroatoms selected from the group consisting of N, O, and S;
wherein $R^{6a}$ is unsubstituted or substituted with 1 to 3 $R^{6a2}$ moieties selected from the group consisting of halo and $C_1$-$C_3$ alkyl;
(v) —O—$R^{6b}$; and
wherein $R^{6b}$ is selected from the group consisting of:
(a) $C_3$-$C_6$ cycloalkyl; and
(b) a group of the formula

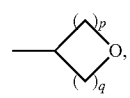

wherein p is 1 or 2, and q is 1 or 2;
wherein $R^{6b}$ is unsubstituted; and
$R^7$ is H or halo.

7. The compound of claim 6 or a pharmaceutically acceptable salt thereof, wherein $R^4$ is —CO$_2$R$^{4a}$, wherein $R^{4a}$ is selected from the group consisting of H and CH$_3$.

8. The compound of claim 6 or a pharmaceutically acceptable salt thereof, wherein $R^6$ is selected from the group consisting of
$C_1$-$C_4$ alkyl, —CF$_3$, —C(H)F$_2$, —O—($C_1$-$C_3$ alkyl), —OCF$_3$, $C_3$-$C_6$ cycloalkyl,

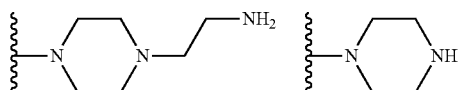

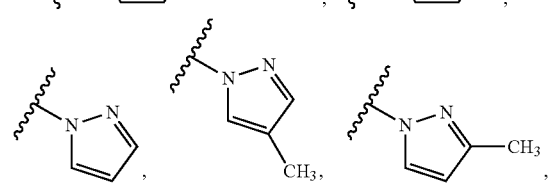

-continued

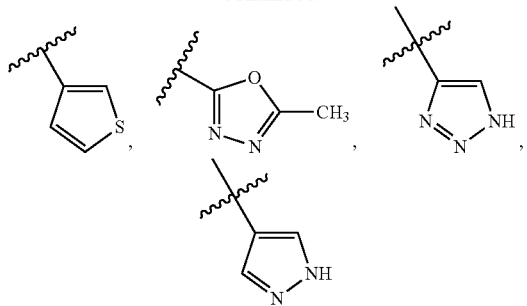

and —O—($C_4$-$C_6$ cycloalkyl).

9. The compound of claim 6 or a pharmaceutically acceptable salt thereof, wherein $R^7$ is H or chloro.

10. The compound of claim 6 or a pharmaceutically acceptable salt thereof, wherein
$R^4$ is —$CO_2R^{4a}$, —C(O)$NH_2$, or —$CH_2OH$;
wherein $R^{4a}$ is selected from the group consisting of H and $CH_3$;
$R^5$ is H or fluoro;
$R^6$ is selected from the group consisting of $C_1$-$C_4$ alkyl, —$CF_3$, —C(H)$F_2$, —O—($C_1$-$C_3$ alkyl), —$OCF_3$, $C_3$-$C_6$ cycloalkyl,

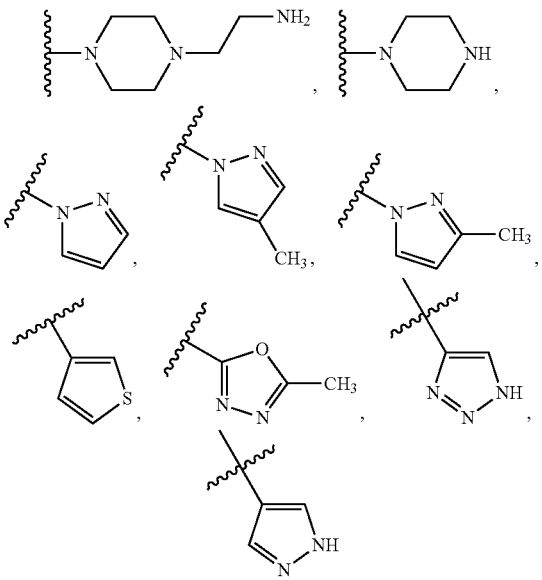

and —O—($C_4$-$C_6$ cycloalkyl); and
$R^7$ is H or chloro.

11. The compound of claim 1, selected from the group consisting of:
5-(5-{6-[(4-tert-butoxypyridin-2-yl)amino]-4-methylpyridin-2-yl}-1,3-thiazol-2-yl)-5-hydroxy-5,6,7,8-tetrahydronaphthalene-2-carboxylic acid;
5-[5-(6-{[4-(difluoromethyl)pyridin-2-yl]amino}-4-methylpyridin-2-yl)-1,3-thiazol-2-yl]-5-hydroxy-5,6,7,8-tetrahydronaphthalene-2-carboxylic acid;
5-[5-(6-{[5-chloro-4-(trifluoromethyl)pyridin-2-yl]amino}-4-methylpyridin-2-yl)-1,3-thiazol-2-yl]-5-hydroxy-5,6,7,8-tetrahydronaphthalene-2-carboxylic acid;
5-{5-[6-({4-[4-(2-aminoethyl)piperazin-1-yl]pyridin-2-yl}amino)-4-methylpyridin-2-yl]-1,3-thiazol-2-yl}-5-hydroxy-5,6,7,8-tetrahydronaphthalene-2-carboxylic acid;
5-hydroxy-5-[5-(4-methyl-6-{[4-(piperazin-1-yl)pyridin-2-yl]amino}pyridin-2-yl)-1,3-thiazol-2-yl]-5,6,7,8-tetrahydronaphthalene-2-carboxylic acid;
5-hydroxy-5-[5-(4-methyl-6-{[4-(4-methyl-1H-pyrazol-1-yl)pyridin-2-yl]amino}pyridin-2-yl)-1,3-thiazol-2-yl]-5,6,7,8-tetrahydronaphthalene-2-carboxylic acid;
5-hydroxy-5-[5-(4-methyl-6-{[4-(1H-pyrazol-1-yl)pyridin-2-yl]amino}pyridin-2-yl)-1,3-thiazol-2-yl]-5,6,7,8-tetrahydronaphthalene-2-carboxylic acid;
5-hydroxy-5-[5-(4-methyl-6-{[4-(thiophen-3-yl)pyridin-2-yl]amino}pyridin-2-yl)-1,3-thiazol-2-yl]-5,6,7,8-tetrahydronaphthalene-2-carboxylic acid;
5-hydroxy-5-(5-{4-methyl-6-[(4-methylpyridin-2-yl)amino]pyridin-2-yl}-1,3-thiazol-2-yl)-5,6,7,8-tetrahydronaphthalene-2-carboxylic acid;
5-[5-(6-{[4-(cyclohexyloxy)pyridin-2-yl]amino}-4-methylpyridin-2-yl)-1,3-thiazol-2-yl]-5-hydroxy-5,6,7,8-tetrahydronaphthalene-2-carboxylic acid;
5-hydroxy-5-[5-(4-methyl-6-{[4-(3-methyl-1H-pyrazol-1-yl)pyridin-2-yl]amino}pyridin-2-yl)-1,3-thiazol-2-yl]-5,6,7,8-tetrahydronaphthalene-2-carboxylic acid;
5-(5-{6-[(4-cyclobutylpyridin-2-yl)amino]-4-methylpyridin-2-yl}-1,3-thiazol-2-yl)-5-hydroxy-5,6,7,8-tetrahydronaphthalene-2-carboxylic acid;
5-[5-(6-{[4-(cyclobutyloxy)pyridin-2-yl]amino}-4-methylpyridin-2-yl)-1,3-thiazol-2-yl]-5-hydroxy-5,6,7,8-tetrahydronaphthalene-2-carboxylic acid;
5-hydroxy-5-(5-{4-methyl-6-[(4-propylpyridin-2-yl)amino]pyridin-2-yl}-1,3-thiazol-2-yl)-5,6,7,8-tetrahydronaphthalene-2-carboxylic acid;
5-(5-{6-[(4-ethoxypyridin-2-yl)amino]-4-methylpyridin-2-yl}-1,3-thiazol-2-yl)-5-hydroxy-5,6,7,8-tetrahydronaphthalene-2-carboxylic acid;
5-[5-(6-{[4-(cyclopentyloxy)pyridin-2-yl]amino}-4-methylpyridin-2-yl)-1,3-thiazol-2-yl]-5-hydroxy-5,6,7,8-tetrahydronaphthalene-2-carboxylic acid;
5-(5-{6-[(4-ethylpyridin-2-yl)amino]-4-methylpyridin-2-yl}-1,3-thiazol-2-yl)-5-hydroxy-5,6,7,8-tetrahydronaphthalene-2-carboxylic acid;
5-(5-{6-[(4-cyclohexylpyridin-2-yl)amino]-4-methylpyridin-2-yl}-1,3-thiazol-2-yl)-5-hydroxy-5,6,7,8-tetrahydronaphthalene-2-carboxylic acid;
5-hydroxy-5-[5-(4-methyl-6-{[4-(propan-2-yloxy)pyridin-2-yl]amino}pyridin-2-yl)-1,3-thiazol-2-yl]-5,6,7,8-tetrahydronaphthalene-2-carboxylic acid;
5-hydroxy-5-[5-(4-methyl-6-{[4-(5-methyl-1,3,4-oxadiazol-2-yl)pyridin-2-yl]amino}pyridin-2-yl)-1,3-thiazol-2-yl]-5,6,7,8-tetrahydronaphthalene-2-carboxylic acid;
5-hydroxy-5-[5-(4-methyl-6-{[4-(tetrahydrofuran-3-yloxy)pyridin-2-yl]amino}pyridin-2-yl)-1,3-thiazol-2-yl]-5,6,7,8-tetrahydronaphthalene-2-carboxylic acid;
5-(5-{6-[(4-cyclopropylpyridin-2-yl)amino]-4-methylpyridin-2-yl}-1,3-thiazol-2-yl)-5-hydroxy-5,6,7,8-tetrahydronaphthalene-2-carboxylic acid;
5-hydroxy-5-[5-(4-methyl-6-{[4-(1-methylethyl)pyridin-2-yl]amino}pyridin-2-yl)-1,3-thiazol-2-yl]-5,6,7,8-tetrahydronaphthalene-2-carboxylic acid;
5-(5-{6-[(4-tert-butylpyridin-2-yl)amino]-4-methylpyridin-2-yl}-1,3-thiazol-2-yl)-5-hydroxy-5,6,7,8-tetrahydronaphthalene-2-carboxylic acid;
5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

methyl 5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

methyl 3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

7-fluoro-6-(hydroxymethyl)-1-[5-(4-methyl-6-{[4-(trifluoromethyl)pyridin-2-yl]amino}pyridin-2-yl)-1,3-thiazol-2-yl]-1,2,3,4-tetrahydronaphthalen-1-ol;

5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

methyl 5-hydroxy-5-[5-(4-methyl-6-{[4-(1H-1,2,3-triazol-4-yl)pyridin-2-yl]amino}pyridin-2-yl)-1,3-thiazol-2-yl]-5,6,7,8-tetrahydronaphthalene-2-carboxylate;

5-hydroxy-5-[5-(4-methyl-6-{[4-(1H-1,2,3-triazol-4-yl)pyridin-2-yl]amino}pyridin-2-yl)-1,3-thiazol-2-yl]-5,6,7,8-tetrahydronaphthalene-2-carboxylic acid;

5-[5-(3-bromo-4-methyl-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

5-[5-(5-bromo-4-methyl-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

5-[5-(3,5-dibromo-4-methyl-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

5-{5-[4-(acetylamino)-6-{[4-(trifluoromethyl)pyridin-2-yl]amino}pyridin-2-yl]-1,3-thiazol-2-yl}-5-hydroxy-5,6,7,8-tetrahydronaphthalene-2-carboxylic acid;

5-[5-(4-amino-6-{[4-(trifluoromethyl)pyridin-2-yl]amino}pyridin-2-yl)-1,3-thiazol-2-yl]-5-hydroxy-5,6,7,8-tetrahydronaphthalene-2-carboxylic acid;

methyl 5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-1-carboxylate;

5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-1-carboxylic acid;

1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-4-carboxylic acid;

9-hydroxy-9-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-2-carboxylic acid;

5-hydroxy-5-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-2-carboxylic acid;

5-hydroxy-5-[5-(4-methyl-6-{[4-(trifluoromethyl)pyridin-2-yl]amino}pyridin-2-yl)-1,3-thiazol-2-yl]-6,7,8,9-tetrahydro-5H-benzo[7]annulene-1-carboxylic acid;

3-hydroxy-3-[5-(4-methyl-6-{[4-(trifluoromethyl)pyridin-2-yl]amino}pyridin-2-yl)-1,3-thiazol-2-yl]-2,3-dihydro-1H-indene-5-carboxylic acid;

methyl 1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-5-carboxylate;

1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-5-carboxylic acid;

methyl 1-bromo-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

1-bromo-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

1-cyano-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

5-hydroxy-1-methoxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

6-bromo-1-[5-(4-methyl-6-{[4-(trifluoromethyl)pyridin-2-yl]amino}pyridin-2-yl)-1,3-thiazol-2-yl]-1,2,3,4-tetrahydronaphthalen-1-ol;

5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carbonitrile;

1-[5-(4-methyl-6-{[4-(trifluoromethyl)pyridin-2-yl]amino}pyridin-2-yl)-1,3-thiazol-2-yl]-6-(2H-tetrazol-5-yl)-1,2,3,4-tetrahydronaphthalen-1-ol;

5-hydroxy-N-(methylsulfonyl)-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

N-(cyclopropylsulfonyl)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

5-hydroxy-N-[(4-methylphenyl)sulfonyl]-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

N-cyano-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

5-hydroxy-5-[5-(4-methyl-6-{[4-(trifluoromethyl)pyridin-2-yl]amino}pyridin-2-yl)-1,3-thiazol-2-yl]-N-[(trifluoromethyl)sulfonyl]-5,6,7,8-tetrahydronaphthalene-2-carboxamide;

5-hydroxy-5-[5-(4-methyl-6-{[4-(trifluoromethyl)pyridin-2-yl]amino}pyridin-2-yl)-1,3-thiazol-2-yl]-N-1H-tetrazol-5-yl-5,6,7,8-tetrahydronaphthalene-2-carboxamide;

5-hydroxy-N-methoxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxamide;

diethyl {5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalen-2-yl}phosphonate;

{5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalen-2-yl}phosphonic acid;

{5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalen-2-yl}boronic acid;

methyl 5-fluoro-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylate;

5-fluoro-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

5-amino-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid;

5-(acetylamino)-5-[5-(4-methyl-6-{[4-(trifluoromethyl) pyridin-2-yl]amino}pyridin-2-yl)-1,3-thiazol-2-yl]-5,6,7,8-tetrahydronaphthalene-2-carboxylic acid;

5-hydroxy-5-(5-{6-[(4-methoxypyridin-2-yl)amino]-4-methylpyridin-2-yl}-1,3-thiazol-2-yl)-5,6,7,8-tetrahydronaphthalene-2-carboxylic acid; and 5-hydroxy-5-(5-{4-methyl-6-[(4-propoxypyridin-2-yl)amino]pyridin-2-yl}-1,3-thiazol-2-yl)-5,6,7,8-tetrahydronaphthalene-2-carboxylic acid;

or a pharmaceutically acceptable salt thereof.

12. A pharmaceutical composition comprising the compound of claim 1 or a pharmaceutically acceptable salt thereof and a pharmaceutically acceptable carrier.

13. A method of treating asthma comprising administering a therapeutically effective amount of the compound of claim 1 or a pharmaceutically acceptable salt thereof to a patient in need thereof.

14. A method of treating chronic obstructive pulmonary disease, comprising administering a therapeutically effective amount of the compound of claim 1 or a pharmaceutically acceptable salt thereof to a patient in need thereof.

15. The compound of claim 1 which is 5-hydroxy-5-[5-(4-methyl-6-{[4-(piperazin-1-yl)pyridin-2-yl]amino}pyridin-2-yl)-1,3-thiazol-2-yl]-5,6,7,8-tetrahydronaphthalene-2-carboxylic acid or a pharmaceutically acceptable salt thereof.

16. The compound of claim 1 which is 5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid or a pharmaceutically acceptable salt thereof.

17. The compound of claim 1 which is 3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid or a pharmaceutically acceptable salt thereof.

18. The compound of claim 1 which is 5-{5-[4-(acetylamino)-6-{[4-(trifluoromethyl)pyridin-2-yl]amino}pyridin-2-yl]-1,3-thiazol-2-yl}-5-hydroxy-5,6,7,8-tetrahydronaphthalene-2-carboxylic acid or a pharmaceutically acceptable salt thereof.

19. The compound of claim 1 which is 1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-4-carboxylic acid or a pharmaceutically acceptable salt thereof.

20. The compound of claim 1 which is 5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carbonitrile or a pharmaceutically acceptable salt thereof.

21. A compound which is (5R)-5-hydroxy-5-[5-(4-methyl-6-{[4-(piperazin-1-yl)pyridin-2-yl]amino}pyridin-2-yl)-1,3-thiazol-2-yl]-5,6,7,8-tetrahydronaphthalene-2-carboxylic acid or a pharmaceutically acceptable salt thereof.

22. A compound which is (5R)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid or a pharmaceutically acceptable salt thereof.

23. A compound which is (5R)-3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid or a pharmaceutically acceptable salt thereof.

24. A compound which is (5R)-5-{5-[4-(acetylamino)-6-{[4-(trifluoromethyl)pyridin-2-yl]amino}pyridin-2-yl]-1,3-thiazol-2-yl}-5-hydroxy-5,6,7,8-tetrahydronaphthalene-2-carboxylic acid or a pharmaceutically acceptable salt thereof.

25. A compound which is (1R)-1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-4-carboxylic acid or a pharmaceutically acceptable salt thereof.

26. A compound which is (5R)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carbonitrile or a pharmaceutically acceptable salt thereof.

27. A compound which is (5R)-5-hydroxy-5-[5-(4-methyl-6-{[4-(piperazin-1-yl)pyridin-2-yl]amino}pyridin-2-yl)-1,3-thiazol-2-yl]-5,6,7,8-tetrahydronaphthalene-2-carboxylic acid.

28. A compound which is (5R)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid.

29. A compound which is (5R)-3-fluoro-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carboxylic acid.

30. A compound which is (5R)-5-{5-[4-(acetylamino)-6-{[4-(trifluoromethyl)pyridin-2-yl]amino}pyridin-2-yl]-1,3-thiazol-2-yl}-5-hydroxy-5,6,7,8-tetrahydronaphthalene-2-carboxylic acid.

31. A compound which is (1R)-1-hydroxy-1-[5-(4-methyl-6-{[4-(trifluoromethyl)pyridin-2-yl]amino}pyridin-2-yl)-1,3-thiazol-2-yl]-2,3-dihydro-1H-indene-4-carboxylic acid.

32. A compound which is (5R)-5-hydroxy-5-[5-(4-methyl-6-{[4-(trifluoromethyl)pyridin-2-yl]amino}pyridin-2-yl)-1,3-thiazol-2-yl]-5,6,7,8-tetrahydronaphthalene-2-carbonitrile.

33. A method of treating asthma comprising administering a therapeutically effective amount of the compound of claim 21 or a pharmaceutically acceptable salt thereof to a patient in need thereof.

34. A method of treating asthma comprising administering a therapeutically effective amount of the compound of claim 22 or a pharmaceutically acceptable salt thereof to a patient in need thereof.

35. A method of treating asthma comprising administering a therapeutically effective amount of the compound of claim 23 or a pharmaceutically acceptable salt thereof to a patient in need thereof.

36. A method of treating asthma comprising administering a therapeutically effective amount of the compound of claim 24 or a pharmaceutically acceptable salt thereof to a patient in need thereof.

37. A method of treating asthma comprising administering a therapeutically effective amount of the compound of claim 25 or a pharmaceutically acceptable salt thereof to a patient in need thereof.

38. A method of treating asthma comprising administering a therapeutically effective amount of the compound of claim 26 or a pharmaceutically acceptable salt thereof to a patient in need thereof.

* * * * *